US012544350B2

(12) United States Patent
Plante et al.

(10) Patent No.: US 12,544,350 B2
(45) Date of Patent: Feb. 10, 2026

(54) COMBINATORIAL ANTITUMOR TREATMENT METHODS AND RELATED COMPOSITIONS, KITS, AND SYSTEMS

(71) Applicant: Klotho Therapeutics, Inc., Las Vegas, NV (US)

(72) Inventors: James Plante, Las Vegas, NV (US); William Ramage, Del Mar, CA (US); Michael Joseph Bishop, San Diego, CA (US); Noriyuki Kasahara, Belvedere Tiburon, CA (US); Yanina Tsenkina, Las Vegas, NV (US); Amanda Crunk, Las Vegas, NV (US)

(73) Assignee: Klotho Therapeutics, Inc., Las Vegas, NV (US)

( * ) Notice: Subject to any disclaimer, the term of this patent is extended or adjusted under 35 U.S.C. 154(b) by 0 days.

(21) Appl. No.: 18/577,214

(22) PCT Filed: Jul. 8, 2022

(86) PCT No.: PCT/US2022/073572
§ 371 (c)(1),
(2) Date: Jan. 5, 2024

(87) PCT Pub. No.: WO2023/283648
PCT Pub. Date: Jan. 12, 2023

(65) Prior Publication Data
US 2024/0277650 A1 Aug. 22, 2024

Related U.S. Application Data

(60) Provisional application No. 63/219,815, filed on Jul. 8, 2021.

(51) Int. Cl.
*A61K 31/216* (2006.01)
*A61K 31/198* (2006.01)
(Continued)

(52) U.S. Cl.
CPC .......... *A61K 31/216* (2013.01); *A61K 31/198* (2013.01); *A61K 31/282* (2013.01);
(Continued)

(58) Field of Classification Search
CPC .. A61K 31/216; A61K 31/198; A61K 31/282; A61K 31/397; A61K 31/40;
(Continued)

(56) References Cited

U.S. PATENT DOCUMENTS

2017/0320898 A1 11/2017 Hukriede et al.
2019/0216755 A1 7/2019 Lichenstein et al.

FOREIGN PATENT DOCUMENTS

CN 107158390 A 9/2017
WO 2022011174 A1 1/2022

OTHER PUBLICATIONS

International Search Report and Written Opinion, mailed Oct. 5, 2022, from PCT/US2022/073572, 12 pages.

(Continued)

*Primary Examiner* — Deborah D Carr
(74) *Attorney, Agent, or Firm* — Workman Nydegger

(57) ABSTRACT

Novel, antitumor treatment methods and related products, in particular, novel, combinatorial antitumor treatment methods and related compositions including (1) cisplatin, or other platinum-based drug, and (2) 4-(phenylthio)butanoic acid (PTBA) or a prodrug of 4-(phenylthio)butanoic acid (PTBA), and kits, systems, or treatment protocols comprising the same, and methods of manufacturing and using the same, particularly for use in cancer or tumor treatment, and specifically, co-administration of (1) cisplatin, or other platinum-based drug, and (2) 4-(phenylthio)butanoic acid (PTBA) or a prodrug of 4-(phenylthio)butanoic acid (PTBA), to cancer patients.

13 Claims, 17 Drawing Sheets

(51) Int. Cl.

| | |
|---|---|
| ***A61K 31/282*** | (2006.01) |
| ***A61K 31/397*** | (2006.01) |
| ***A61K 31/40*** | (2006.01) |
| ***A61K 31/445*** | (2006.01) |
| ***A61K 31/495*** | (2006.01) |
| ***A61K 31/555*** | (2006.01) |
| ***A61K 33/243*** | (2019.01) |
| ***A61P 35/00*** | (2006.01) |

(52) U.S. Cl.
CPC ............ *A61K 31/397* (2013.01); *A61K 31/40* (2013.01); *A61K 31/445* (2013.01); *A61K 31/495* (2013.01); *A61K 31/555* (2013.01); *A61K 33/243* (2019.01); *A61P 35/00* (2018.01)

(58) Field of Classification Search
CPC .. A61K 31/445; A61K 31/495; A61K 31/555; A61K 33/243; A61P 35/00
See application file for complete search history.

(56) References Cited

OTHER PUBLICATIONS

National Library of Medicine / National Center for Biotechnology Information, "Pubchem Cid 75433538" 1-10, Web. Jul. 12, 2014, p. 2.
National Library of Medicine / National Center for Biotechnology Information, "Pubchem Cid 215570" 1-12, Web. Aug. 9, 2005, p. 2.

| Compound | Structure | MW | Molecular Formula | Kinetic Solubility PBS pH=7.4 (uM) | SMILES |
|---|---|---|---|---|---|
| 1 |  | 307.5 | C17H25NO2S. C2HO2F3 | >400 | CCN1CCC(CC1)OC(=O)CCCSC=2C=CC=CC2.OC(=O)C(F)(F)F |
| 2 |  | 307.5 | C17H25NO2S. C2HO2F3 | >400 | CN1CCC(C)(CC1)OC(=O)CCCSC=2C=CC=CC2.OC(=O)C(F)(F)F |
| 3 |  | 267.4 | C14H21NO2S. C2HO2F3 | 381 | CN(C)CCOC(=O)CCCSC=1C=CC=CC1.OC(=O)C(F)(F)F |
| 4 |  | 293.4 | C16H23NO2S. C2HO2F3 | 387 | CN1CCC(CC1)OC(=O)CCCSC=2C=CC=CC2.OC(=O)C(F)(F)F |
| 5 |  | 325.4 | C15H19NO5S | 396 | OC(=O)CC[C@@H](NC(=O)CCCSC=1C=CC=CC1)C(=O)O |

| | | | | | |
|---|---|---|---|---|---|
| 6 |  | 270.3 | C13H18O4S | >400 | OCC(O)COC(=O)CCCSC=1C=CC=CC1 |
| 7 |  | 284.4 | C14H20O4S | 385 | OCCOCCOC(=O)CCCSC=1C=CC=CC1 |
| 8 |  | 310.4 | HCl.C15H22N2O3S | 383 | Cl.NCCC[C@@H](NC(=O)CCCSC=1C=CC=CC1)C(=O)O |
| 9 |  | 425.5 | C19H27N3O6S.C2HO2F3 | 383 | NCCC[C@@H](NC(=O)CCCSC=1C=CC=CC1)C(=O)N[C@H](CC(=O)O)C(=O)O.OC(=O)C(F)(F)F |
| 10 |  | 425.5 | C19H27N3O6S.C2HO2F3 | 379 | NCCC[C@@H](NC(=O)[C@@H](CC(=O)O)NC(=O)CCCSC=1C=CC=CC1)C(=O)O.OC(=O)C(F)(F)F |

| | | | | | |
|---|---|---|---|---|---|
| 11 |  | 439.5 | C20H29N3O6S.C2HO2F3 | 391 | NCCC[C@@H](NC(=O)CCCSC=1C=CC=CC1)C(=O)N[C@H](CCC(=O)O)C(=O)O.OC(=O)C(F)(F)F |
| 12 |  | 439.5 | C20H29N3O6S.C2HO2F3 | >400 | NCCC[C@@H](NC(=O)[C@@H](CCC(=O)O)NC(=O)CCCSC=1C=CC=CC1)C(=O)O.OC(=O)C(F)(F)F |
| 13 |  | 322.5 | C17H26N2O2S.C2HO2F3 | >400 | CN1CCN(CCOC(=O)CCCSC=2C=CC=CC2)CC1.OC(=O)C(F)(F)F |
| 14 |  | 311.4 | C14H17NO5S | 387 | OC(=O)C[C@@H](NC(=O)CCCSC=1C=CC=CC1)C(=O)O |
| 15 |  | 305.4 | C17H23NO2S | ≥400 | CN1CC2(CC(C2)OC(=O)CCCSC=3C=CC=CC3)C1 |

| | | | | | |
|---|---|---|---|---|---|
| 16 |  | 283.4 | C14H21NO3S | >400 | OCCNCCOC(=O)CCCSC=1C=CC=CC1 |
| 17 |  | 265.4 | C14H19NO2S. C2HO2F3 | >400 | OC(=O)C(F)(F)F.O=C(CCCSC=1C=CC=CC1)O[C@@H]2CCNC2 |
| 18 |  | 281.4 | C15H23NO2S. C2HO2F3 | 362 | C[C@H](CN(C)C)OC(=O)CCCSC=1C=CC=CC1.OC(=O)C(F)(F)F |
| 19 |  | 312.3 | C14H16O6S | >400 | OC(=O)C[C@H](OC(=O)CCCSC=1C=CC=CC1)C(=O)O |
| 20 |  | 412.5 | C18H24N2O7S | >400 | OC[C@H](NC(=O)CCCSC=1C=CC=CC1)C(=O)N[C@@H](CCC(=O)O)C(=O)O |

| | | | | | |
|---|---|---|---|---|---|
| 21 |  | 412.5 | C18H24N2O7S.C2HO2F3 | >400 | N[C@@H](COC(=O)CCCSC=1C=CC=CC1)C(=O)N[C@@H](CCC(=O)O)C(=O)O.OC(=O)C(F)(F)F |
| 22 |  | 282.4 | Cl.C15H24NO2S | 398 | [Cl-].C[N+](C)(C)CCOC(=O)CCCSC=1C=CC=CC1 |
| 23 |  | 367.5 | C18H29N3O3S.C2HO2F3.C2HO2F3 | 399 | NCCCC[C@@H](N)C(=O)NCCOC(=O)CCCSC=1C=CC=CC1.OC(=O)C(F)(F)F.OC(=O)C(F)(F)F |
| 24 |  | 352.5 | C18H28N2O3S | 390 | CC(C)[C@H](N)C(=O)NCCCOC(=O)CCCSC=1C=CC=CC1 |

% Compound 22 remaining in Rat Plasma vs. Time:

% Compound 22 remaining in Dog Plasma vs. Time

% Compound 22 remaining in Human Plasma vs. Time

COMBINATORIAL ANTITUMOR TREATMENT METHODS AND RELATED COMPOSITIONS, KITS, AND SYSTEMS

CROSS-REFERENCE TO RELATED APPLICATIONS

This application is a nationalization of PCT/US22/73572, filed Jul. 8, 2022, which claims the benefit of and priority to U.S. Provisional Application No. 63/219,815, filed Jul. 8, 2021, the entirety of each of which is incorporated herein by reference.

BACKGROUND

1. Technical Field

The present disclosure relates to novel, antitumor treatment methods and related products. In particular, the present disclosure relates to novel, combinatorial antitumor treatment methods and related compositions including (1) cisplatin, or other platinum-based drug, and (2) 4-(phenylthio) butanoic acid (PTBA) or a prodrug of 4-(phenylthio) butanoic acid (PTBA), and to kits, systems, or treatment protocols comprising the same, and to methods of manufacturing and using the same, particularly for use in cancer or tumor treatment. Specifically, the present disclosure relates to co-administration of (1) cisplatin, or other platinum-based drug, and (2) 4-(phenylthio)butanoic acid (PTBA) or a prodrug of 4-(phenylthio)butanoic acid (PTBA), to cancer patients.

2. Related Technology

Platinum anticancer agents (or "platins") are among the most widely used chemotherapeutic drugs and are administered in about 50% of all chemotherapeutic regimens. cisplatin, in particular, has emerged as an effective chemotherapeutic in the treatment of testicular cancer, ovarian cancer, cervical cancer, breast cancer, bladder cancer, head and neck cancer, esophageal cancer, lung cancer, mesothelioma, brain tumors and neuroblastoma, and other cancers. Cisplatin is particularly effective against testicular cancer; its adoption has increased the cure rate from 10% to 85%. Other platins, such as oxaliplatin, carboplatin, etc. have also been effective in cancer treatment.

Cisplatin interferes with DNA replication, which kills the fastest proliferating cells, which in theory are cancerous. Specifically, cisplatin crosslinks DNA in several different ways, interfering with cell division by mitosis. The damaged DNA elicits DNA repair mechanisms, which in turn activate apoptosis when repair proves impossible. In 2008, for example, researchers were able to show that the apoptosis induced by cisplatin on human colon cancer cells depends on the mitochondrial serine-protease Omi/Htra2. Most notable among the changes in DNA are the 1,2-intrastrand cross-links with purine bases. These include 1,2-intrastrand d(GpG) adducts which form nearly 90% of the adducts and the less common 1,2-intrastrand d(ApG) adducts. 1,3-intrastrand d(GpXpG) adducts occur but are readily excised by the nucleotide excision repair (NER). Other adducts include inter-strand crosslinks and nonfunctional adducts that have been postulated to contribute to cisplatin's activity. Interaction with cellular proteins, particularly HMG domain proteins, has also been suggested as a mechanism of interfering with mitosis.

Cisplatin does, however, have a number of side effects that can limit its use. Nephrotoxicity (kidney damage), for example, is a major concern. Nephrotoxicity is a dose-limiting side effect; the dose of cisplatin may need to be reduced when the person's kidney function is impaired. Neurotoxicity (nerve damage) and other neurological side effects of cisplatin include visual perception and hearing disorder, which can occur soon after treatment begins. Nausea and vomiting are also common in cisplatin patients. Cisplatin is one of the most emetogenic chemotherapy agents. Ototoxicity (hearing loss) can occur in cisplatin patients. Cisplatin can also cause electrolyte disturbance, such as hypomagnesaemia, hypokalaemia, hypocalcaemia, and hemolytic anemia, which can be developed after several courses of cisplatin.

Accordingly, there are a number of short-comings in the art related to platin-based chemotherapeutic drugs, drug systems, and treatment protocols.

Severe acute kidney injury (AKI) is remarkably common and has an unacceptably high mortality that has been unchanged for the last twenty-plus years. AKI therapies that have been developed in experimental models when administered prior to the onset of injury have failed to show therapeutic benefit in humans. AKI is a multi-factorial disorder that occurs in approximately 7% of in-patients hospital admissions. It is an independent predictor of in-hospital mortality. Severe AKI requiring renal replacement therapy occurs in 4% of critically ill patients and has 50% in-patient mortality. Long term follow up studies in survivors of severe AKI indicate that approximately 12.5% become dialysis-dependent. Despite these sobering statistics, renal replacement is the only approved therapy for AKI, and there are no established therapies that have been proven to prevent renal injury or accelerate the rate of renal recovery following induction of AKI in man. Without being bound to any particular theory, chronic kidney disease (CKD) is similarly plagued with a lack of available therapies and may involve similar pathways of renal injury. Therefore, there is an urgent need to develop effective therapies that will accelerate the rate of recovery following induction of renal injury. WO 2012109527, the entirety of which is incorporated herein by reference, provides examples of certain useful therapies.

Notwithstanding the foregoing, the kidney does have an innate capacity to undergo epithelial regeneration following injury, suggesting that drugs that enhance this regenerative capacity are more likely to be of benefit when given after the onset of injury. Guo et al. published the *Epigenetic regulation in AKI and kidney repair: mechanisms and therapeutic implications* (Nature Reviews Nephrology volume 15, pages 220-239(2019)), reviewing the emerging role of epigenetic regulation in the process of AKI and kidney repair (e.g., involving remarkable changes in histone modifications, DNA methylation and the expression of various non-coding RNAs). In summary, increases in levels of histone acetylation seem to protect kidneys from AKI and promote kidney repair. AKI is also associated with changes in genome-wide and gene-specific DNA methylation; however, the role and regulation of DNA methylation in kidney injury and repair remains largely elusive. In 2010, de Groh et al. published *Inhibition of histone deacetylase expands the renal progenitor cell population* (J Am Soc Nephrol 21: 794-802, 2010), in which the group identified a new histone deacetylase inhibitor (HDACi), 4-(phenylthio)butanoic acid (PTBA), that seemed to expand the pool of renal progenitor cells in zebrafish embryos in a proliferation-dependent manner, thereby enhancing renal recovery, increasing renal tubular endothelial cell (RTEC) proliferation, and reducing renal fibrosis. Without being bound to any theory, PTBA was shown to increase renal tubular cell proliferation, increase survival, and increase renal functional recovery in zebrafish and various models of acute kidney injury. Immunohistological analyses suggested increased cell proliferation to be accompanied by increased epithelial-to-mesenchymal transition in the RTECs. Later, Cosentino et al. published *Histone Deacetylase Inhibitor Enhances Recovery after AKI* (Journal of the American Society of Nephrology, Vol. 24, Issue 6, June 2013), Skrypnyk et al. published *Delayed treatment with PTBA analogs reduces postinjury renal fibrosis after kidney injury* (Am J Physiol Renal Physiol. 2016 Apr. 15; 310(8): F705-F716; Published online 2015 Dec. 9), and Skvarca et al. published *Enhancing regeneration after acute kidney injury by promoting cellular dedifferentiation in zebrafish* (Dis Model Mech. 2019 Apr. 1; 12(4): dmm037390; Published online 2019 Apr. 5). WO2012109527 and corresponding US20150246939 further disclose that a *Class of HDAC Inhibitors Expands the Renal Progenitor Cells Population and improves the Rate of Recovery from acute Kidney Injury*. Each of the foregoing references is incorporated by herein by reference, in its entirety.

However, there remains a need for improved and/or optimized compounds that serve as non-toxic, water soluble prodrugs of PTBA and that are suitable for (U.S. Food and Drug Administration (FDA)-approved) administration, particularly for use in inhibiting HDAC activity and/or for enhancing renal recovery (e.g., following AKI or for treating chronic kidney disease CKD)), preferably through HDAC inhibition, and methods of manufacturing and using the same. The use of water soluble prodrugs has been studied and reported (see e.g., Jornada et al., *The Prodrug Approach: A Successful Tool for Improving Drug Solubility* (Molecules 2016, 21, 42), the entirety of which is incorporated herein by specific reference. However, the art of small molecule optimization, particularly the combination of water solubility of prodrugs, remains unpredictable, requiring time-consuming, detail-oriented experimentation, as opposed to mere routine optimization.

As the so-called "baby boomers" generation continues to advance in age, the population of aging individuals (e.g., age 60-65) is rapidly increasing globally. This aging population increasingly suffers from AKI and CKD. The increased demand for health care for this aging population places significant financial burden on any healthcare system. Molecular compounds (or so-called "small molecules") provide promising therapeutic agents to counter age-related health conditions. Developing strategies and health intervention methods based on the production and purification of compounds that inhibit HDAC (activity), and the administration of such compounds to subjects may help to ameliorate this situation and the problems associated therewith. Developing strategies and health intervention methods based on the administration of small molecule prodrugs of PTBA (that inhibit HDAC activity and, thereby, improve renal recovery and/or function), especially humans and/or within an increasing aging population, may help to ameliorate this situation.

Currently, there is not a commercial, small molecule product (e.g., a (highly) water-soluble PTBA prodrug or pharmaceutically-acceptable salt thereof and/or composition comprising the same) or treatment method for improving renal recovery and/or function (e.g., following AKI or in response to CKD), particularly through inhibition of HDAC activity, especially products and methods approved by the U.S. Food and Drug Administration (FDA). To date, all relevant data is connected to pre-clinical, research trials in animal models. Accordingly, there are a number of shortcomings in the art that can be addressed by the development, production, manufacture, and administration of new, water soluble prodrugs of PTBA and compositions comprising the same, particularly for use in inhibiting HDAC activity and/or for enhancing renal recovery following AKI or treating chronic kidney disease, preferably through HDAC inhibition.

Accordingly, there is a need for treatment compositions, methods, kits/systems, etc. that address cancer and drug-induced nephrotoxicity or AKI, particularly, nephrotoxin-induced AKI.

BRIEF SUMMARY

Embodiments of the present disclosure solve one or more of the foregoing or other problems in the art with novel, antitumor treatment compositions, kits/systems, treatment protocols, and methods. In particular, embodiments of the present disclosure relate to novel, combinatorial antitumor treatment compositions, kits/systems, treatment protocols, and methods including (1) cisplatin, or other platinum-based drug (e.g., oxaliplatin, carboplatin, nedaplatin, phenanthriplatin, picoplatin, etc.), and (2) 4-(phenylthio)butanoic acid (PTBA) or a (novel) prodrug of 4-(phenylthio)butanoic acid (PTBA), and to methods of manufacturing and using the same, particularly for use in cancer treatment. Specifically, embodiments of the present disclosure relate to co-administration of (1) cisplatin, or other platinum-based drug, and (2) 4-(phenylthio)butanoic acid (PTBA) or a prodrug of 4-(phenylthio)butanoic acid (PTBA), to cancer patients.

In embodiments of the present disclosure, the cisplatin, or other platinum-based drug (e.g., oxaliplatin, carboplatin, nedaplatin, phenanthriplatin, picoplatin, etc.), can be administered as known in the art to treat the particular cancer or tumor with which the patient is diagnosed. Such administration can, therefore, be or comprise a therapeutic administration or administration of a therapeutically-effective amount of a platinum-based drug (e.g., cisplatin, oxaliplatin, carboplatin, nedaplatin, phenanthriplatin, picoplatin, etc.), or in an amount effective to treat the cancer or tumor. As used herein, "treating" cancer or tumor, and similar terms, may refer to eradicating, killing, destroying, or reducing the number of cancer cells or reducing the size of a tumor.

In embodiments of the present disclosure, the platinum-based drug can be co-administered with a novel compound (e.g., a so-called small molecule), illustratively comprising a (water soluble and/or non-toxic) prodrug of PTBA. As used herein, "co-administered" and similar terms, refers to the coordinated, concomitant, or contemporaneous administration of (1) the platinum-based drug, and (2) the novel compound. In some embodiments, co-administration can comprise simultaneous administration. It is understood that co-administration, or simultaneous administration, can comprise separate administrations, e.g., in separate pharmaceutical preparations. For example, co-administration, or simultaneous administration, can comprise administration of one pharmaceutical preparation comprising cisplatin, or other platinum-based drug, and another pharmaceutical preparation comprising the novel compound. It is also understood that co-administration, or simultaneous administration, can comprise one pharmaceutical preparation comprising both (1) cisplatin, or other platinum-based drug, and (2) the novel compound. The platinum-based drug, and the novel compound can also be co-administered separately from each other—e.g., in separate dosages of the co-administration. When the platinum-based drug and the novel compound are co-administered separately, at least one dose of the novel compound is preferably co-administered within about 48 hours (2 days) of each other, preferably within about 24 hours (1 day) of each other, more preferably within about 18 hours of each other, still more preferably within about 12 hours of each other, still more preferably within about 8 hours of each other, still more preferably within about 6 hours of each other, still more preferably within about 2 hours of each other, still more preferably within about 1 hour of each other, still more preferably within about 30 minutes of each other, still more preferably within about 15 minutes of each other, still more preferably within about 10 minutes of each other, still more preferably within about 5 minutes of each other.

In some embodiments, co-administration of the platinum-based drug and the novel compound can involve following an established dosage regime for the platinum-based drug and co-administering the novel compound (e.g., once daily or twice daily). In some embodiments, one or more pre-platin dose(s) of the novel compound can be administered (e.g., once daily or twice daily) within the 1-14 days prior to administration of the platinum-based drug. For instance, the novel compound can be administered (e.g., once daily or twice daily) 7 days before, 6 days before, 5 days before, 4 days, before, 3 days before, 2 days before, and/or 1 day before administration of the platinum-based drug. Moreover, at least one dose of the novel compound can also (or alternatively) be administered within 48 hours or less of (e.g., simultaneously with) the/each dose of platinum-based drug, and one or more additional dose(s) of the novel compound can be subsequently (e.g., once daily or twice daily) administered for an additional co-administration treatment period (e.g., within the 1-14 days following the/each dose of platinum-based drug). For instance, the novel compound can be administered (e.g., once daily or twice daily) 1 day after, 2 days after, 3 days after, 4 days after, 5 days after, 6 days after, 7 days after, 8 days after, 9 days after, 10 days after, 11 days after, 12 days after, 13 days after, and/or 14 days after the/each administration of the platinum-based drug.

In some embodiments, each dose of the novel compound—whether before, during, or after administration of the/each dose of the platinum-based drug—can have the same concentration. For example, each dose of the novel compound can be administered in an amount sufficient to provide about 100 mg/kg (mg of compound per kg of subject body mass/weight), 90 mg/kg, 80 mg/kg, 75 mg/kg, 70 mg/kg, 60 mg/kg, 50 mg/kg, 40 mg/kg, 30 mg/kg, 25 mg/kg, 20 mg/kg, 15 mg/kg, 10 mg/kg, 5 mg/kg, 2.5 mg/kg, or 1 mg/kg, or between about 1-100 mg/kg, 2.5-90 mg/kg, 5-80 mg/kg, 10-75 mg/kg, 15-70 mg/kg, 20-60 mg/kg, 25-50 mg/kg, or any range therebetween. Alternatively, certain doses of the novel compound may have a different concentration than other doses. For example, one or more doses of the novel compound (e.g., dose(s) administered within 5 days, 4 days, 3 days, 2 days/48 hours, 1 day/24 hours, or less of the/each dose of the platinum-based drug) can have a first concentration of the novel compound, and one or more additional doses of the novel compound (e.g., dose(s) administered more than 5 days, 4 days, 3 days, 2 days/48 hours, or 1 day/24 hours before or after the/each dose of the platinum-based drug) can have a second concentration of the novel compound. In some embodiments, the second concentration can be less than the first concentration. In other embodiments, the second concentration can be more than the first concentration.

In embodiments of the present disclosure, the novel compounds (e.g., so-called small molecules) serve as (water soluble and/or non-toxic) prodrugs of PTBA, preferably for use in inhibiting HDAC activity and/or for enhancing renal recovery following AKI, particular nephrotoxin-induced AKI, preferably through HDAC inhibition, and methods of manufacturing and using the same. Illustratively, the novel compounds are, or function as, therapeutic agents that accelerate recovery from AKI by enhancing the innate regenerative capacity of the kidney, illustratively through HDAC inhibition. Accordingly, the present disclosure provides a number of compounds with direct application in human (and other mammal) AKI and, optionally, for CKD. Embodiments of the present disclosure include compounds, compositions comprising said compounds, medicaments comprising said compounds or compositions, methods of manufacturing said medicaments, compounds, and compositions, and uses of said medicaments, compounds, and compositions, or methods of using said medicaments, compounds, and compositions.

Some embodiments include a method of treating kidney injury or disease or improving kidney function in patients, particularly following AKI—e.g., nephrotoxin-induced AKI—or prophylactically treating (preventing, attenuating, reducing, etc.) kidney injury, such as AKI—e.g., nephrotoxin-induced AKI. In some embodiments, the nephrotoxin can be or comprise a chemotherapeutic agent, such as a platinum-based drug. Illustrative treatment methods comprise administering to a patient an amount of a novel compound, composition, or medicament as described herein, and co-administering a platinum-based drug. In various embodiments, the administered amount is effective to treat, prevent, attenuate, or reduce kidney injury or disease or to improve kidney function in a patient, preferably following AKI—e.g., nephrotoxin-induced AKI. For example, the compound or pharmaceutically acceptable salt thereof can be administered in an amount and in a dosage regimen effective to improve kidney function in a patient, to inhibit a histone deacetylase (activity) in a cell (e.g., renal cell) or systemically, to expand renal progenitor cells, and/or to stimulate kidney repair in cells (in vitro, ex vivo or in vivo). The manufacture and/or use of any compound, composition, and/or medicament described herein also is provided, preferably for treating kidney injury or disease or improving kidney function in a patient.

Illustratively, novel compounds of the present disclosure are designed to be effective for use as prodrugs of 4-(phenylthio)butanoic acid (PTBA) and/or for use in inhibiting histone deacetylase (HDAC) activity. Inhibition of HDAC activity has been shown to have several downstream and/or therapeutic effects. Those skilled in the art will appreciate that any disease or condition that is caused, worsened, or exacerbated, in whole or in part, by (or associated with) high or excessive HDAC activity, may be addressed and/or treated (post-diagnosis or prophylactically) by administration of the novel compound(s), or composition(s) comprising the same, disclosed herein.

Embodiments of the present disclosure include a pharmaceutical treatment system (or kit) for co-administration to a cancer patient, the treatment system comprising: a platinum-based chemotherapeutic drug in an amount sufficient to reduce the number of cancer cells in the patient; and a prodrug of 4-(phenylthio)butanoic acid (PTBA) in an amount sufficient to attenuate kidney injury induced by the platinum-based chemotherapeutic drug in the patient and/or improve kidney function in the patient.

In some embodiments, the platinum-based chemotherapeutic drug and the prodrug are each disposed in a pharmaceutically-acceptable carrier or excipient. In some embodiments, the platinum-based chemotherapeutic drug and the prodrug are co-formulated in a pharmaceutically-acceptable carrier or excipient. In other embodiments, the platinum-based chemotherapeutic drug and the prodrug are each disposed in separate and/or different pharmaceutically-acceptable carriers or excipients.

In various embodiments, the prodrug of PTBA can be or comprise a compound according to Formula I:

Formula I

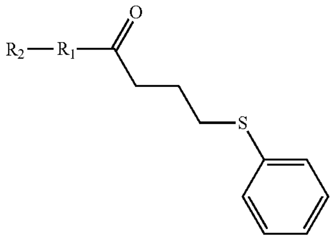

or a stereoisomer, tautomer or pharmaceutically acceptable salt thereof.

In various embodiments, $R_1$ is O or NH. In some embodiments, $R_1$ is O. In some embodiments, $R_1$ is NH.

In some embodiments, $R_2$ is not H. In some embodiments, $R_2$ is not $CH_3$. In some embodiments, $R_2$ is not, one or more of, alkyl, ethyl, propyl, isopropyl, or butyl. In some embodiments, $R_2$ is not aryl, phenyl or benzyl. In some embodiments, $R_2$ is not carboxyl (COOH). In some embodiments, $R_2$ is not, one or more of, methanol, ethanol, propanol, or isopropanol. In some embodiments, when $R_1$ is O, then $R_2$ is not H. In some embodiments, when $R_1$ is O, then $R_2$ is not $CH_3$. In some embodiments, when $R_1$ is O, then $R_2$ is not, one or more of, alkyl, ethyl, propyl, isopropyl, or butyl. In some embodiments, when $R_1$ is O, then $R_2$ is not aryl, phenyl or benzyl. In some embodiments, when $R_1$ is O, then $R_2$ is not carboxyl (COOH). In some embodiments, when $R_1$ is NH, then $R_2$ is not H. In some embodiments, when $R_1$ is NH, then $R_2$ is not $CH_3$. In some embodiments, when $R_1$ is NH, then $R_2$ is not, one or more of, alkyl, ethyl, propyl, isopropyl, or butyl. In some embodiments, when $R_1$ is NH, then $R_2$ is not aryl, phenyl or benzyl. In some embodiments, when $R_1$ is NH, then $R_2$ is not carboxyl (COOH).

In various embodiments, $R_2$ is one of:

substituted or unsubstituted amine, preferably substituted or unsubstituted tertiary amine or quaternary amine (trisubstituted ammonium or quaternary ammonium), more preferably 1-(N,N-dimethyl)ethanamine, 1-(1-methyl-N,N-dimethyl)ethanamine, or 1-(N,N,N-trimethyl)ethanamine, substituted or unsubstituted heterocyclic amine or azaspiroalkyl (or hetero-dualcycloalkyl), preferably 5-7 member heterocyclic amine or azaspiroalkyl, optionally substituted at one or more ring positions with C1-C2 alkyl, or 4-7 member substituted or unsubstituted heterocycloalkyl or hetero-dualcycloalkyl (a.k.a. azaspiroalkyl), optionally substituted at 1-4 (ring) positions and each (ring) substituent is one of branched or unbranched C1-C3 substituted or unsubstituted alkyl or cycloalkyl, more preferably substituted or unsubstituted pyrrolidine, piperidine, or piperazine, still more preferably, substituted or unsubstituted 3-N-pyrrolidine, 4-N-piperidine, or 4-N-piperazine, still more preferably, 4-N-piperidine or 4-N-piperazine substituted at C-1, N-4, or C-1 and N-4, still more preferably, 4-N-methylpiperidine, 4-N-ethylpiperidine, 4-N-1,4-methylpiperidine, 4-N-methylpiperazine, or substituted or unsubstituted azaspiroheptyl, preferably 2-azaspiroheptyl or azaspiro[3.3]heptyl, still more preferably 2-azaspiro[3.3]heptyl, still more preferably 2-methyl-2-azaspiro[3.3]heptyl, alkanolamine, preferably ethanolamine, more preferably N-ethylethanolamine or 2-(ethylamino)ethanol, alkoxyalcohol, preferably alkoxy ethanol or ethoxy alcohol, more preferably 2-ethoxyethanol, polyol, preferably diol, more preferably propanediol, still more preferably 2,3-propanediol, carboxylic acid, preferably dicarboxylic acid, more preferably butanedioic acid, still more preferably, butanedioic acid, amide, preferably substituted amide, more preferably N-ethyl-N-amide, N-propyl-N-amide, or 2-amino-propanamide, still more preferably 2,6-diamino-N-ethyl-N-hexanamide, 2-amino-3-methyl-N-propyl-N-butanamide, or N-(1,3-dicarboyl)-2-amino-propanamide, or wherein the amide comprises:

—$R_3$—C(═O)NH—$R_4$, wherein $R_3$ is substituted alkyl, preferably substituted ethyl, more preferably amino ethyl, still more preferably 2-amino ethyl, and $R_4$ is carboxylic acid, preferably dicarboxylic acid, more preferably pentanedioic acid, still more preferably, pentanedioic acid or pentanedioic acid, or —$R_5$—NHC(═O)—$R_6$, wherein $R_5$ is substituted alkyl, ethyl or propyl, and $R_6$ is substituted alkyl, preferably 1-amino-2-methylpropane or 1,5-diaminopentane, branched or unbranched C2-C10 substituted or unsubstituted alkyl, amine, amide, acetyl, aldehyde, alkoxy (ether), ester, carbonyl, carboxyl, carbamate, diol, triol, trisubstituted ammonium, optionally substituted at 1-5 positions and each substituent is one of branched or unbranched C1-C5 substituted or unsubstituted alkyl, amine, amide, acetyl, aldehyde, alkoxy (ether), hydroxy, ester, carbonyl, carboxyl, carbamate, diol, triol, trisubstituted ammonium, —X—$R_7$, wherein X is C1-C3 branched or unbranched alkyl, and wherein $R_7$ is a 4-7 member substituted or unsubstituted heterocycloalkyl or hetero-dualcycloalkyl (a.k.a. azaspiroalkyl), optionally substituted at 1-4 (ring) positions and each (ring) substituent is one of branched or unbranched C1-C3 substituted or unsubstituted alkyl or cycloalkyl, preferably substituted or unsubstituted pyrrolidine, piperidine, or piperazine, more preferably, substituted or unsubstituted 3-N-pyrrolidine, 4-N-piperidine, or 4-N-piperazine, still more preferably, 4-N-piperidine or 4-N-piperazine substituted at C-1, N-4, or C-1 and N-4, still more preferably, 4-N-methylpiperidine, 4-N-ethylpiperidine, 4-N-1,4-methylpiperidine, 4-N-methylpiperazine, most preferably, 4-N-methylpiperazine, preferably when X is $(CH_2)_2$, or tertiary amine or quaternary amine (trisubstituted ammonium or quaternary ammonium), more preferably 1-(N,N-dimethyl)ethanamine, 1-(1-methyl-N,N-dimethyl)ethanamine, or 1-(N,N,N-trimethyl) ethanamine, branched or unbranched C2-C10 substituted or unsubstituted alkyl, amine, amide, acetyl, aldehyde, alkoxy (ether), ester, carbonyl, carboxyl, carbamate, diol, triol, trisubstituted ammonium, optionally substituted at 1-5 positions and each substituent is one of branched or unbranched C1-C5 substituted or unsubstituted alkyl, amine, amide, acetyl, aldehyde, alkoxy (ether), hydroxy, ester, carbonyl, carboxyl, carbamate, diol, triol, trisubstituted ammonium, —$(CR_8R_9)_Z$—$R_{10}$, wherein Z is an integer from 1-3, each $R_8$ is, independently, one of H or $CH_3$, each $R_9$ is, independently, selected from: H, hydroxyl (OH), carboxyl (COOH), amino ($NH_2$), or together with $R_{10}$, forms substituted or unsubstituted heterocyclic amine or azaspiroalkyl (or hetero-dualcycloalkyl), preferably 5-7 member heterocyclic amine or azaspiroalkyl, optionally substituted at one or more ring positions with C1-C2 alkyl, more preferably 5-6 member heterocyclic amine or 7 member azaspiroalkyl, optionally substituted at one or more ring positions with C1-C2 alkyl, substituted or unsubstituted pyrrolidine, piperidine, or piperazine, still more preferably, substituted or unsubstituted 3-N-pyrrolidine, 4-N-piperidine, or 4-N-piperazine, still more preferably unsubstituted 3-N-pyrrolidine or substituted 4-N-piperidine or 4-N-piperazine, substituted at C-1, N-4, or C-1 and N-4, still more preferably, 4-N-methylpiperidine, 4-N-ethylpiperidine, 4-N-1,4-methylpiperidine, or 4-N-methyl-1-piperazine, or substituted or unsubstituted azaspiroheptyl, preferably substituted or unsubstituted 2-azaspiroheptyl or azaspiro[3.3]heptyl, still more preferably substituted or unsubstituted 2-azaspiro[3.3]heptyl, still more preferably 2-methyl-2-azaspiro[3.3]heptyl, and each $R_{10}$ is, independently, one of:

amine, preferably tertiary amine or quaternary amine (trisubstituted ammonium or quaternary ammonium), more preferably 1-(N,N-dimethyl)amine, 1-(1-methyl-N,N-dimethyl)amine, or 1-(N,N,N-trimethyl)amine, optionally substituted heterocyclic amine, preferably 6 member heterocyclic amine, still more preferably 6 member heterocyclic amine, still more preferably piperazine, still more preferably, 4-N-piperazine, still more preferably 4-N-methylpiperazine or 4-N-methyl-1-piperazine, alkanolamine, preferably ethanolamine, N-ethanolamine or 1-aminoethanol, alkoxyalcohol, preferably alkoxy ethanol or ethoxy alcohol, polyol, preferably diol, more preferably ethanediol, carboxyl (COOH), amide, preferably substituted amide, more preferably substituted N-pentanamide, N-hexanamide, or 1-amide, more preferably 2,6-diamino-N-hexanamide, 2-amino-3-methyl-N-butanamide, or N-(1,3-dicarboyl)-2-amino-1-amide, or wherein the amide comprises:

—C(═O)NH—$R_1$, wherein $R_1$ is carboxylic acid, preferably dicarboxylic acid, more preferably pentanedioic acid, still more preferably, pentanedioic acid or pentanedioic acid, or —NHC(═O)—$R_{12}$, wherein $R_{12}$ is substituted alkyl, preferably 1-amino-2-methylpropane or 1,5-diaminopentane, together with $R_9$, forms substituted or unsubstituted heterocyclic amine or azaspiroalkyl (or hetero-dualcycloalkyl), preferably 5-7 member heterocyclic amine or azaspiroalkyl, optionally substituted at one or more ring positions with C1-C2 alkyl, more preferably 5-6 member heterocyclic amine or 7 member azaspiroalkyl, optionally substituted at one or more ring positions with C1-C2 alkyl, substituted or unsubstituted pyrrolidine, piperidine, or piperazine, still more preferably, substituted or unsubstituted 3-N-pyrrolidine, 4-N-piperidine, or 4-N-piperazine, still more preferably unsubstituted 3-N-pyrrolidine or substituted 4-N-piperidine or 4-N-piperazine, substituted at C-1, N-4, or C-1 and N-4, still more preferably, 4-N-methylpiperidine, 4-N-ethylpiperidine, 4-N-1,4-methylpiperidine, or 4-N-methyl-1-piperazine, or substituted or unsubstituted azaspiroheptyl, preferably substituted or unsubstituted 2-azaspiroheptyl or azaspiro[3.3]heptyl, still more preferably substituted or unsubstituted 2-azaspiro[3.3]heptyl, still more preferably 2-methyl-2-azaspiro[3.3]heptyl, or —$(CR_{13}R_{14})_Z$—$R_{15}$, wherein each $R_{13}$ is H, each $R_{14}$ is, independently, one of H, $CH_3$, carboxyl (COOH), ethanol ($CH_2OH$), preferably 2-ethanol, amine or alkylamine, preferably propylamine, carboxylic acid, preferably ethanoic acid or propanoic acid, Z is and integer from 1-3, and $R_{15}$ is carboxyl (—COOH), amino (—$NH_2$), or amide, preferably 1-amide, more preferably N-substituted-1-amide (or N-substituted carboxamide) (—CONH—$R_{16}$, where $R_{16}$ is substituted alkyl, preferably 1,3-dicarboxypropane, 1-(1-carboxy)butyric acid or butanedioic acid, 1-carboxy-2-pentanoic acid or pentanedioic acid, preferably 2-pentanedioic acid, or 2-(3-aminopropyl)ethanoic acid.

In some embodiments, when $R_1$ is O, then $R_2$ is one of:

substituted or unsubstituted amine, preferably substituted or unsubstituted tertiary amine or quaternary amine (trisubstituted ammonium or quaternary ammonium), more preferably 1-(N,N-dimethyl)ethanamine, 1-(1-methyl-N,N-dimethyl)ethanamine, or 1-(N,N,N-trimethyl)ethanamine, substituted or unsubstituted heterocyclic amine or azaspiroalkyl (or hetero-dualcycloalkyl), preferably 5-7 member heterocyclic amine or azaspiroalkyl, optionally substituted at one or more ring positions with C1-C2 alkyl, or 4-7 member substituted or unsubstituted heterocycloalkyl or hetero-dualcycloalkyl (a.k.a. azaspiroalkyl), optionally substituted at 1-4 (ring) positions and each (ring) substituent is one of branched or unbranched C1-C3 substituted or unsubstituted alkyl or cycloalkyl, more preferably substituted or unsubstituted pyrrolidine, piperidine, or piperazine, still more preferably, substituted or unsubstituted 3-N-pyrrolidine, 4-N-piperidine, or 4-N-piperazine, still more preferably, 4-N-piperidine or 4-N-piperazine substituted at C-1, N-4, or C-1 and N-4, still more preferably, 4-N-methylpiperidine, 4-N-ethylpiperidine, 4-N-1,4-methylpiperidine, 4-N-methylpiperazine, or substituted or unsubstituted azaspiroheptyl, preferably 2-azaspiroheptyl or azaspiro[3.3]heptyl, still more preferably 2-azaspiro[3.3]heptyl, still more preferably 2-methyl-2-azaspiro[3.3]heptyl, alkanolamine, preferably ethanolamine, more preferably N-ethylethanolamine or 2-(ethylamino)ethanol, alkoxyalcohol, preferably alkoxy ethanol or ethoxy alcohol, more preferably 2-ethoxyethanol, polyol, preferably diol, more preferably propanediol, still more preferably 2,3-propanediol, carboxylic acid, preferably dicarboxylic acid, more preferably butanedioic acid, still more preferably, butanedioic acid or butanedioic acid, amide, preferably substituted amide, more preferably N-ethyl-N-amide, N-propyl-N-amide, or 2-amino-propanamide, still more preferably 2,6-diamino-N-ethyl-N-hexanamide, 2-amino-3-methyl-N-propyl-N-butanamide, or N-(1,3-dicarboyl)-2-amino-propanamide, or wherein the amide comprises:

—$R_3$—C(═O)NH—$R_4$, wherein $R_3$ is substituted alkyl, preferably substituted ethyl, more preferably amino ethyl, still more preferably 2-amino ethyl, and $R_4$ is carboxylic acid, preferably dicarboxylic acid, more preferably pentanedioic acid, still more preferably, pentanedioic acid or pentanedioic acid, —$R_5$—NHC(═O)—$R_6$, wherein $R_5$ is substituted alkyl, ethyl or propyl, and $R_6$ is substituted alkyl, preferably 1-amino-2-methylpropane or 1,5-diaminopentane, branched or unbranched C2-C10 substituted or unsubstituted alkyl, amine, amide, acetyl, aldehyde, alkoxy (ether), ester, carbonyl, carboxyl, carbamate, diol, triol, trisubstituted ammonium, optionally substituted at 1-5 positions and each substituent is one of branched or unbranched C1-C5 substituted or unsubstituted alkyl, amine, amide, acetyl, aldehyde, alkoxy (ether), hydroxy, ester, carbonyl, carboxyl, carbamate, diol, triol, trisubstituted ammonium, or —X—$R_7$, wherein X is C1-C3 branched or unbranched alkyl, and wherein $R_7$ is a 4-7 member substituted or unsubstituted heterocycloalkyl or hetero-dualcycloalkyl (a.k.a. azaspiroalkyl), optionally substituted at 1-4 (ring) positions and each (ring) substituent is one of branched or unbranched C1-C3 substituted or unsubstituted alkyl or cycloalkyl, preferably substituted or unsubstituted pyrrolidine, piperidine, or piperazine, more preferably, substituted or unsubstituted 3-N-pyrrolidine, 4-N-piperidine, or 4-N-piperazine, still more preferably, 4-N-piperidine or 4-N-piperazine substituted at C-1, N-4, or C-1 and N-4, still more preferably, 4-N-methylpiperidine, 4-N-ethylpiperidine, 4-N-1,4-methylpiperidine, 4-N-methylpiperazine, most preferably, 4-N-methylpiperazine, preferably when X is $(CH_2)_2$, or tertiary amine or quaternary amine (trisubstituted ammonium or quaternary ammonium), more preferably 1-(N,N-dimethyl)ethanamine, 1-(1-methyl-N,N-dimethyl)ethanamine, or 1-(N,N,N-trimethyl) ethanamine, branched or unbranched C2-C10 substituted or unsubstituted alkyl, amine, amide, acetyl, aldehyde, alkoxy (ether), ester, carbonyl, carboxyl, carbamate, diol, triol, trisubstituted ammonium, optionally substituted at 1-5 positions and each substituent is one of branched or unbranched C1-C5 substituted or unsubstituted alkyl, amine, amide, acetyl, aldehyde, alkoxy (ether), hydroxy, ester, carbonyl, carboxyl, carbamate, diol, triol, trisubstituted ammonium.

In some embodiments, when $R_1$ is O, then $R_2$ is one of:

substituted or unsubstituted amine, preferably substituted or unsubstituted tertiary amine or quaternary amine (trisubstituted ammonium or quaternary ammonium), more preferably 1-(N,N-dimethyl)ethanamine, 1-(1-methyl-N,N-dimethyl)ethanamine, or 1-(N,N,N-trimethyl)ethanamine, substituted or unsubstituted heterocyclic amine or azaspiroalkyl, preferably 5-7 member heterocyclic amine or azaspiroalkyl, optionally substituted at one or more ring positions with C1-C2 alkyl, alkanolamine, preferably ethanolamine, more preferably N-ethylethanolamine or 2-(ethylamino)ethanol, alkoxyalcohol, preferably alkoxy ethanol or ethoxy alcohol, more preferably 2-ethoxyethanol, polyol, preferably diol, more preferably propanediol, still more preferably 2,3-propanediol, carboxylic acid, preferably dicarboxylic acid, more preferably butanedioic acid, still more preferably, butanedioic acid or butanedioic acid, amide, preferably substituted amide, more preferably N-ethyl-N-amide, N-propyl-N-amide, or 2-amino-propanamide, still more preferably 2,6-diamino-N-ethyl-N-hexanamide, 2-amino-3-methyl-N-propyl-N-butanamide, or N-(1,3-dicarboyl)-2-amino-propanamide, or wherein the amide comprises:

—$R_3$—C(═O)NH—$R_4$, wherein $R_3$ is substituted alkyl, preferably substituted ethyl, more preferably amino ethyl, still more preferably 2-amino ethyl, and $R_4$ is carboxylic acid, preferably dicarboxylic acid, more preferably pentanedioic acid, still more preferably, pentanedioic acid or pentanedioic acid, or —$R_5$—NHC(═O)—$R_6$, wherein $R_5$ is one of substituted alkyl, ethyl or propyl, and $R_6$ is substituted alkyl, preferably 1-amino-2-methylpropane or 1,5-diaminopentane.

In some embodiments, when $R_1$ is O, then $R_2$ is $(CR_8R_9)_z$—$R_{10}$, wherein:

Z is an integer from 1-3, each $R_8$ is, independently, H or $CH_3$, each $R_9$ is, independently, one of: H, hydroxyl (OH), carboxyl (COOH), amino ($NH_2$), or together with $R_{10}$, forms substituted or unsubstituted heterocyclic amine or azaspiroalkyl (or hetero-dualcycloalkyl), preferably 5-7 member heterocyclic amine or azaspiroalkyl, optionally substituted at one or more ring positions with C1-C2 alkyl, more preferably 5-6 member heterocyclic amine or 7 member azaspiroalkyl, optionally substituted at one or more ring positions with C1-C2 alkyl, substituted or unsubstituted pyrrolidine, piperidine, or piperazine, still more preferably, substituted or unsubstituted 3-N-pyrrolidine, 4-N-piperidine, or 4-N-piperazine, still more preferably unsubstituted 3-N-pyrrolidine or substituted 4-N-piperidine or 4-N-piperazine, substituted at C-1, N-4, or C-1 and N-4, still more preferably, 4-N-methylpiperidine, 4-N-ethylpiperidine, 4-N-1,4-methylpiperidine, or 4-N-methyl-1-piperazine, or substituted or unsubstituted azaspiroheptyl, preferably substituted or unsubstituted 2-azaspiroheptyl or azaspiro[3.3]heptyl, still more preferably substituted or unsubstituted 2-azaspiro[3.3]heptyl, still more preferably 2-methyl-2-azaspiro[3.3]heptyl, and each $R_{10}$ is, independently, one of:

amine, preferably tertiary amine or quaternary amine (trisubstituted ammonium or quaternary ammonium), more preferably 1-(N,N-dimethyl)amine, 1-(1-methyl-N,N-dimethyl)amine, or 1-(N,N,N-trimethyl)amine, optionally substituted heterocyclic amine, preferably 6 member heterocyclic amine, still more preferably 6 member heterocyclic amine, still more preferably piperazine, still more preferably, 4-N-piperazine, still more preferably 4-N-methylpiperazine or 4-N-methyl-1-piperazine, alkanolamine, preferably ethanolamine, N-ethanolamine or 1-aminoethanol, alkoxyalcohol, preferably alkoxy ethanol or ethoxy alcohol, polyol, preferably diol, more preferably ethanediol, carboxyl (COOH), amide, preferably substituted amide, more preferably substituted N-pentanamide, N-hexanamide, or 1-amide, more preferably 2,6-diamino-N-hexanamide, 2-amino-3-methyl-N-butanamide, or N-(1,3-dicarboyl)-2-amino-1-amide, or wherein the amide comprises:

C(═O)NH—$R_{11}$, wherein $R_4$ is carboxylic acid, preferably dicarboxylic acid, more preferably pentanedioic acid, still more preferably, pentanedioic acid or pentanedioic acid, or —NHC(═O)—$R_{12}$, wherein $R_{12}$ is substituted alkyl, preferably 1-amino-2-methylpropane or 1,5-diaminopentane, or together with $R_9$, forms substituted or unsubstituted heterocyclic amine or azaspiroalkyl (or hetero-dual-cycloalkyl), preferably 5-7 member heterocyclic amine or azaspiroalkyl, optionally substituted at one or more ring positions with C1-C2 alkyl, more preferably 5-6 member heterocyclic amine or 7 member azaspiroalkyl, optionally substituted at one or more ring positions with C1-C2 alkyl, substituted or unsubstituted pyrrolidine, piperidine, or piperazine, still more preferably, substituted or unsubstituted 3-N-pyrrolidine, 4-N-piperidine, or 4-N-piperazine, still more preferably unsubstituted 3-N-pyrrolidine or substituted 4-N-piperidine or 4-N-piperazine, substituted at C-1, N-4, or C-1 and N-4, still more preferably, 4-N-methylpiperidine, 4-N-ethylpiperidine, 4-N-1,4-methylpiperidine, or 4-N-methyl-1-piperazine, or substituted or unsubstituted azaspiroheptyl, preferably substituted or unsubstituted 2-azaspiroheplyl or azaspiro[3.3]heptyl, still more preferably substituted or unsubstituted 2-azaspiro[3.3]heptyl, still more preferably 2-methyl-2-azaspiro[3.3]heptyl, In some embodiments, when $R_1$ is O, then $R_2$ is one of Formulas Ia-Ip:

Formula Ia

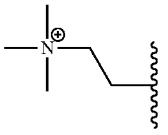

Formula Ib

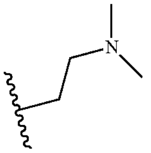

Formula Ic

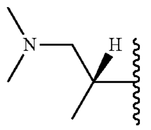

Formula Id

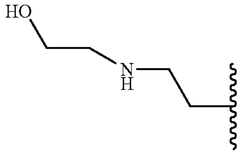

-continued

Formula Ie

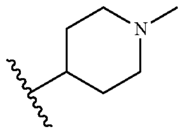

Formula If

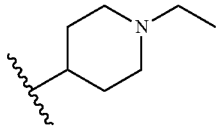

Formula Ig

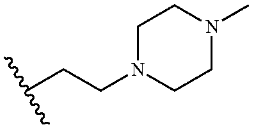

Formula Ih

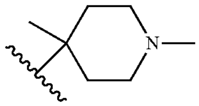

Formula Ii

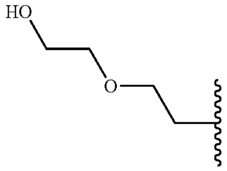

Formula Ij

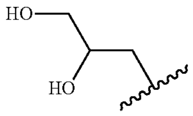

Formila Ik

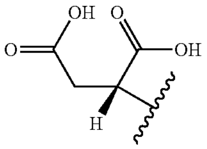

Formula Il

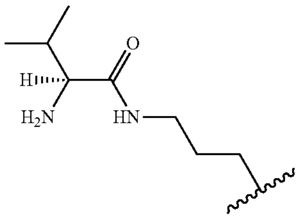

Formula Im

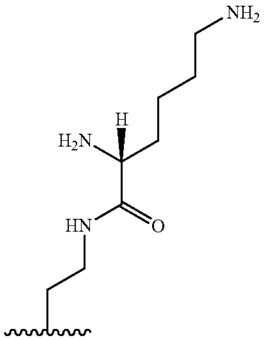

-continued

Formula In

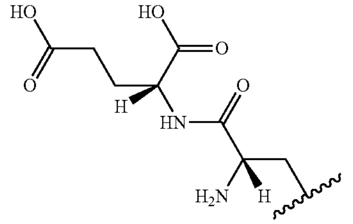

Formula Io

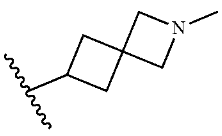

Formula Ip

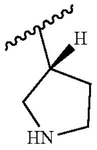

In some embodiments, when $R_1$ is O, then $R_2$ is $CR_{17}R_{18})_2$—$R_{19}$, wherein each $R_{17}$ is H and each $R_{18}$ is, independently, H or $CH_3$; and $R_{19}$ is $N(CH_3)_Y$, wherein Y is an integer from 2-3.

In some embodiments, when $R_1$ is O, then $R_2$ is $(CH_2)_2$—$R_{19}$, and $R_{19}$ is $^+N(CH_3)_3$, or, in other words, is:

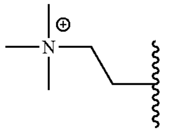 [SMILES: *CC[N+](C)(C)C]

In some embodiments, when $R_1$ is NH, then $R_2$ is one of:

branched or unbranched C2-C10 substituted or unsubstituted alkyl, amine, amide, acetyl, aldehyde, alkoxy (ether), ester, carbonyl, carboxyl, carbamate, diol, triol, trisubstituted ammonium, optionally substituted at 1-5 positions and each substituent is one of branched or unbranched C1-C5 substituted or unsubstituted alkyl, amine, amide, acetyl, aldehyde, alkoxy (ether), hydroxy, ester, carbonyl, carboxyl, carbamate, diol, triol, trisubstituted ammonium.

In some embodiments, when $R_1$ is NH, then $R_2$ is one of:

carboxylic acid or dicarboxylic acid, preferably pentanoic acid, butanedioic acid, or pentanedioic acid, still more preferably, 2-(6-amino)-pentanoic acid, 2-butanedioic acid or 2-butanedioic acid, or 2-pentanedioic acid or 2-pentanedioic acid, and amide, preferably substituted amide, more preferably substituted ethanamide, still more preferably substituted 2-ethanamide, still more preferably 2-(3-aminopropane)-N-2-butanedioic-2-ethanamide, 2-(3-aminopropane)-N-2-butanedioic-2-ethanamide, 2-(3-aminopropane)-N-2-pentanedioic-2-ethanamide, 2-(3-aminopropane)-N-2-pentanedioic-2-ethanamide, 2-(2-carboxyethyl)-N-(2-(3-aminopropane)-carboxymethyl)-2-ethanamide, 2-carboxymethyl-N-(2-(3-aminopropane)-carboxymethyl)-2-ethanamide, or 2-(hydroxymethyl)-N-2-pentanedioic-2-ethanamide.

In some embodiments, when $R_1$ is NH, then $R_2$ is one of:

2-butanedioic acid, 2-pentanedioic acid, or 2-(5-amino)-pentanoic acid, and 2-(3-aminopropane)-N-2-butanedioic-2-ethanamide, 2-(3-aminopropane)-N-2-butanedioic-2-ethanamide, 2-(3-aminopropane)-N-2-pentanedioic-2-ethanamide, 2-(3-aminopropane)-N-2-pentanedioic-2-ethanamide, 2-(2-carboxyethyl)-N-(2-(3-aminopropane)-carboxymethyl)-2-ethanamide, 2-carboxymethyl-N-(2-(3-aminopropane)-carboxymethyl)-2-ethanamide, or 2-(hydroxymethyl)-N-2-pentanedioic-2-ethanamide.

In some embodiments, when $R_1$ is NH, then $R_2$ is $(CR_{13}R_{14})_Z$—$R_{15}$, wherein each $R_{13}$ is H;

each $R_{14}$ is, independently, one of H, $CH_3$, carboxyl (COOH), ethanol ($CH_2OH$), preferably 2-ethanol, amine or alkylamine, preferably propylamine, carboxylic acid, preferably ethanoic acid or propanoic acid, Z is and integer from 1-3, and $R_{15}$ is one of carboxyl (—COOH), amino (—$NH_2$), or amide, preferably 1-amide, more preferably N-substituted-1-amide (or N-substituted carboxamide) (—CONH—$R_{16}$, where $R_{16}$ is substituted alkyl, preferably 1,3-dicarboxypropane, 1-(1-carboxy)butyric acid or butanedioic acid, 1-carboxy-2-pentanoic acid or pentanedioic acid, preferably 2-pentanedioic acid, or 2-(3-aminopropyl)ethanoic acid.

In some embodiments, when $R_1$ is NH, then $R_2$ is one of Formulas Iq-Ix:

Formula Iq

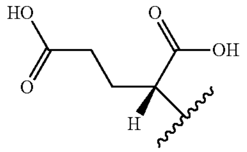

Formula Ir

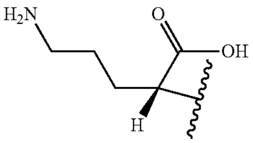

Formula Is

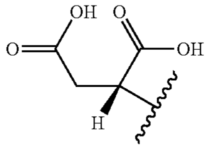

Formula It

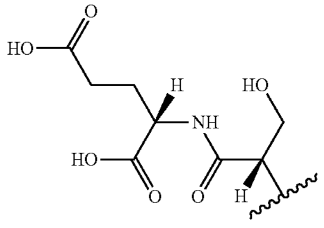

Formula Iu

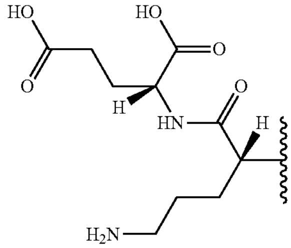

-continued
Formula Iv
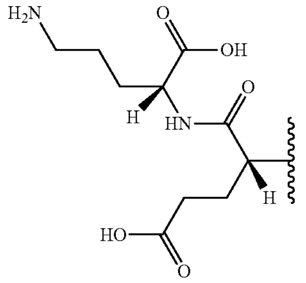
Formula Iw
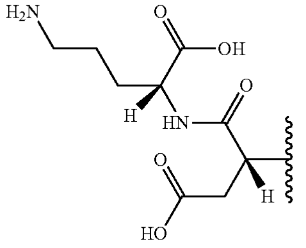
-continued
Formula Ix
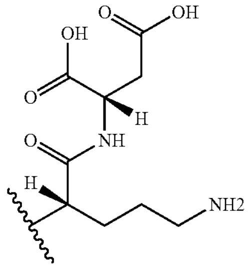
In some embodiments, the compound according to Formula I can be one of Compounds 1-24 of Table 1. Table 1. Nonlimiting examples of illustrative compounds:
TABLE 1
| Compound | Structure | MW | Molecular Formula |
|---|---|---|---|
| 1 | 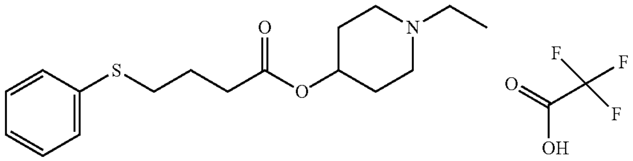 [SMILES: CCN1CCC(OC(=O)CCCSc2ccccc2)CC1 ; O=C(O)C(F)(F)F] | 307.5 | C17H25NO2S• C2HO2F3 |
| 2 | 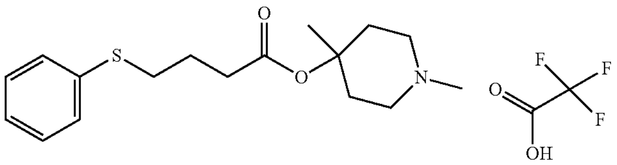 | 307.5 | C17H25NO2S• C2HO2F3 |
| 3 | 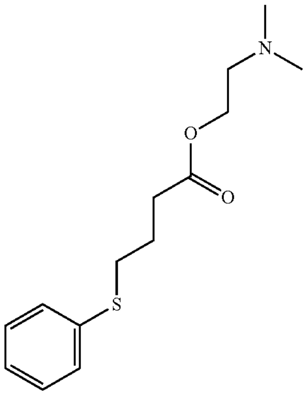 [SMILES: CN(C)CCOC(=O)CCCSc1ccccc1] | 267.4 | C14H21NO2S |
| 4 | 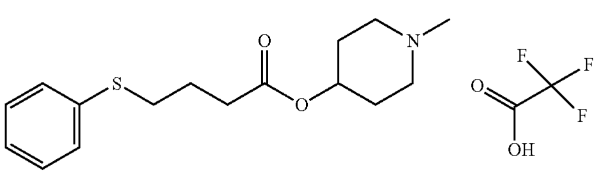 [SMILES: CN1CCC(OC(=O)CCCSc2ccccc2)CC1 ; O=C(O)C(F)(F)F] | 293.4 | C16H23NO2S• C2HO2F3 |

TABLE 1-continued
| Compound | Structure | MW | Molecular Formula |
|---|---|---|---|
| 5 | 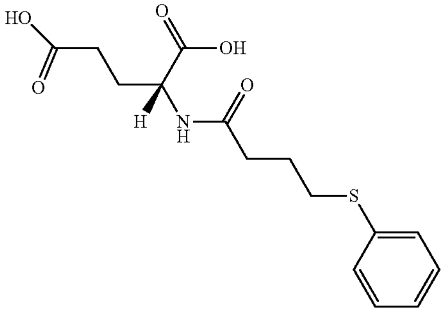 [SMILES: O=C(O)CC[C@@H](NC(=O)CCCSc1ccccc1)C(=O)O] | 325.4 | C15H19NO5S |
| 6 | 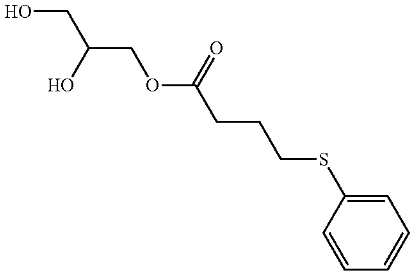 [SMILES: O=C(CCCSc1ccccc1)OCC(O)CO] | 270.3 | C13H18O4S |
| 7 | 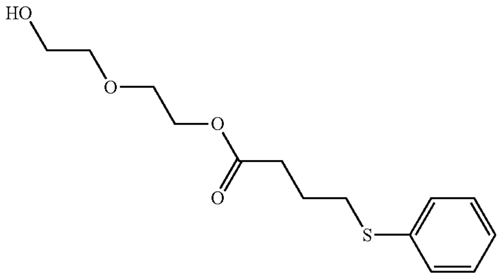 [SMILES: O=C(CCCSc1ccccc1)OCCOCCO] | 284.4 | C14H20O4S |
| 8 | 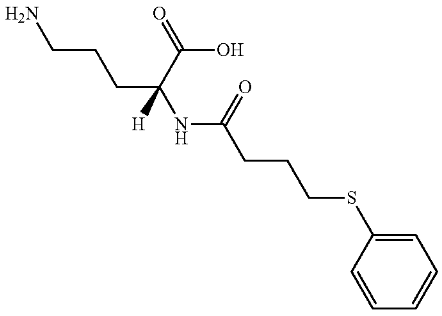 HCl | 310.4 | HCl• C15H22N2O3S |

TABLE 1-continued
| Compound | Structure | MW | Molecular Formula |
|---|---|---|---|
| 9 | 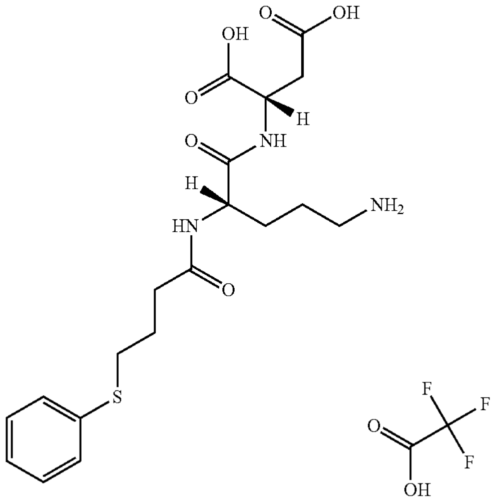 [SMILES: NCCC[C@H](NC(=O)CCCSc1ccccc1)C(=O)N[C@@H](CC(=O)O)C(=O)O ; O=C(O)C(F)(F)F] | 425.5 | C19H27N3O6S•C2HO2F3 |
| 10 | 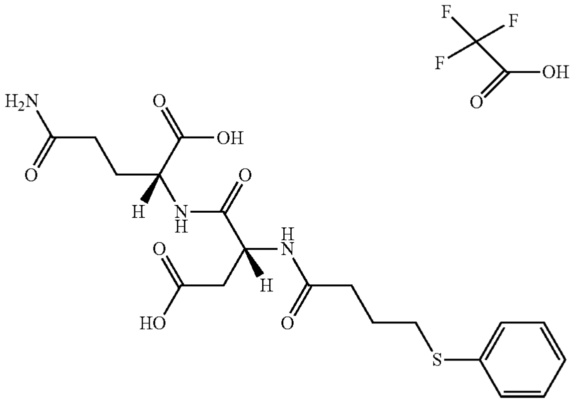 [SMILES: NC(=O)CC[C@@H](NC(=O)[C@@H](CC(=O)O)NC(=O)CCCSc1ccccc1)C(=O)O ; O=C(O)C(F)(F)F] | 425.5 | C19H27N3O6S•C2HO2F3 |
| 11 | 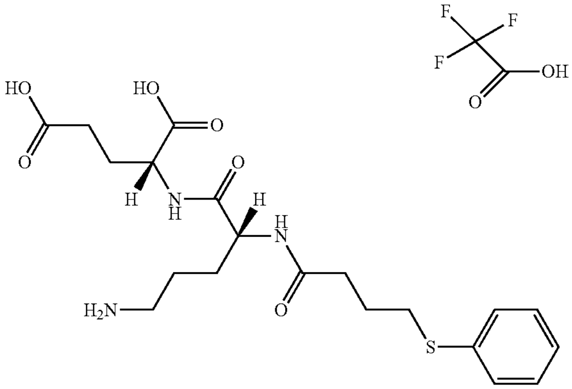 [SMILES: NCCC[C@@H](NC(=O)CCCSc1ccccc1)C(=O)N[C@H](CCC(=O)O)C(=O)O ; O=C(O)C(F)(F)F] | 439.5 | C20H29N3O6S•C2HO2F3 |

TABLE 1-continued
| Compound | Structure | MW | Molecular Formula |
|---|---|---|---|
| 12 | 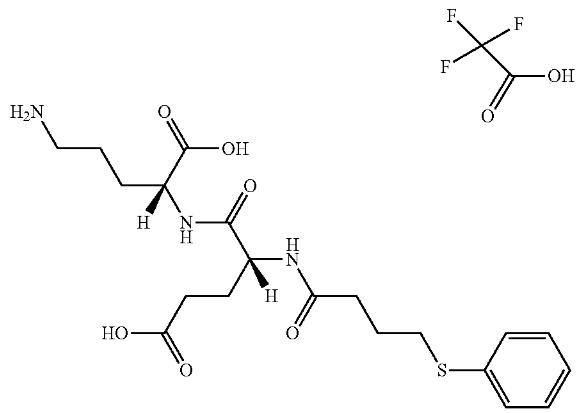 [SMILES: NCCC[C@@H](NC(=O)[C@@H](CCC(=O)O)NC(=O)CCCSc1ccccc1)C(=O)O ; O=C(O)C(F)(F)F] | 439.5 | C20H29N3O6S• C2HO2F3 |
| 13 | 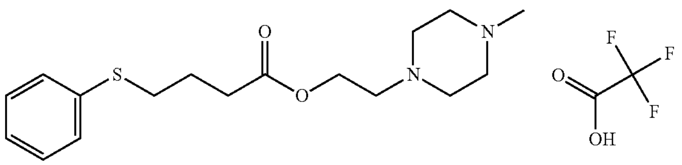 [SMILES: CN1CCN(CCOC(=O)CCCSc2ccccc2)CC1 ; O=C(O)C(F)(F)F] | 322.5 | C17H26N2O2S• C2HO2F3 |
| 14 | 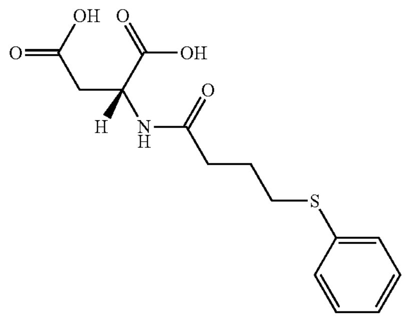 [SMILES: O=C(O)C[C@@H](NC(=O)CCCSc1ccccc1)C(=O)O] | 311.4 | C14H17NO5S |
| 15 | 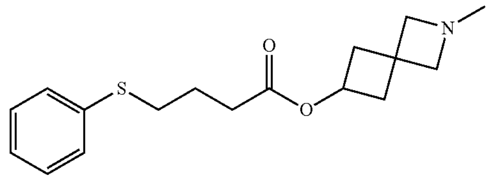 [SMILES: CN1CC2(CC(OC(=O)CCCSc3ccccc3)C2)C1] | 305.4 | C17H23NO2S |
| 16 | 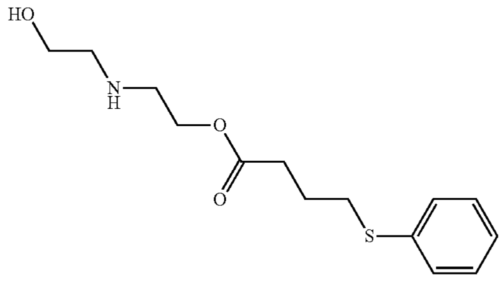 | 283.4 | C14H21NO3S |

TABLE 1-continued
| Compound | Structure | MW | Molecular Formula |
| --- | --- | --- | --- |
| 17 | 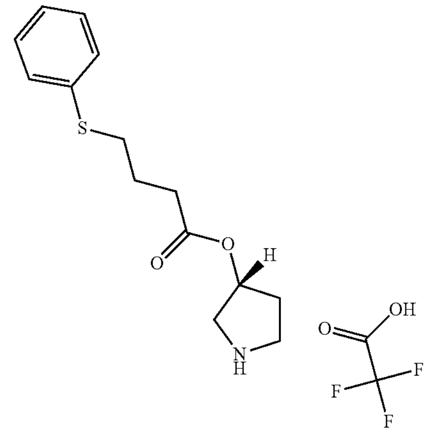 | 265.4 | $C_{14}H_{19}NO_2S \cdot C_2HO_2F_3$ |
| 18 | 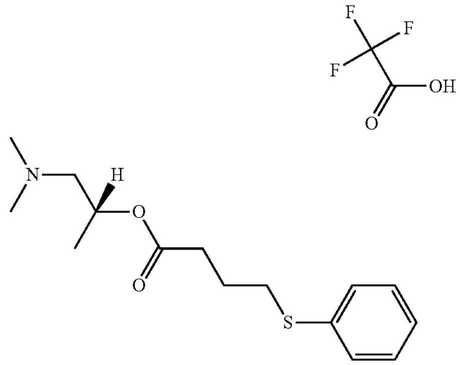 [SMILES: O=C(O)C(F)(F)F ; C[C@H](CN(C)C)OC(=O)CCCSc1ccccc1] | 281.4 | $C_{15}H_{23}NO_2S \cdot C_2HO_2F_3$ |
| 19 | 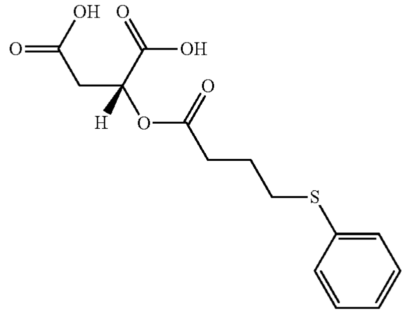 [SMILES: O=C(O)C[C@@H](OC(=O)CCCSc1ccccc1)C(=O)O] | 312.3 | $C_{14}H_{16}O_6S$ |
| 20 | 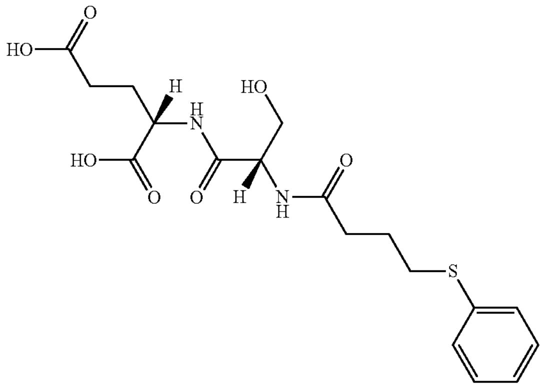 [SMILES: O=C(O)CC[C@H](NC(=O)[C@H](CO)NC(=O)CCCSc1ccccc1)C(=O)O] | 412.5 | $C_{18}H_{24}N_2O_7S$ |

TABLE 1-continued
| Compound | Structure | MW | Molecular Formula |
|---|---|---|---|
| 21 | 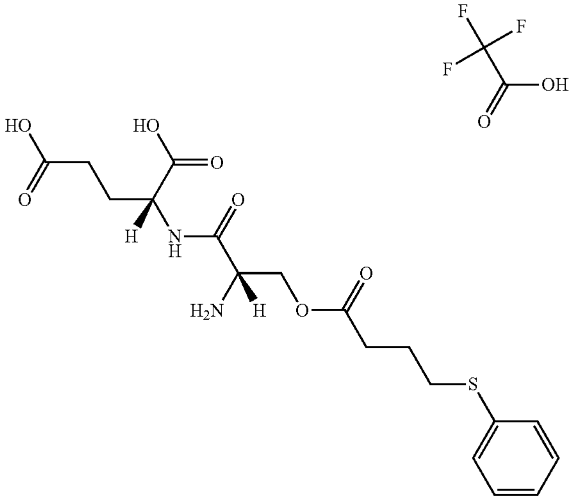 [SMILES: O=C(O)C(F)(F)F ; N[C@@H](COC(=O)CCCSc1ccccc1)C(=O)N[C@H](CCC(=O)O)C(=O)O] | 412.5 | C18H24N2O7S• C2HO2F3 |
| 22 | 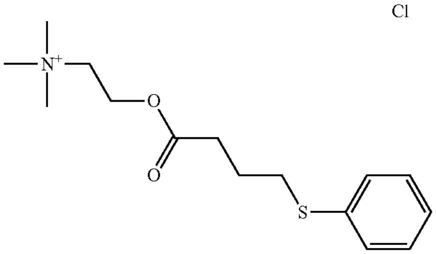 [SMILES: Cl ; C[N+](C)(C)CCOC(=O)CCCSc1ccccc1] | 282.4 | Cl• C15H24NO2S |
| 23 | 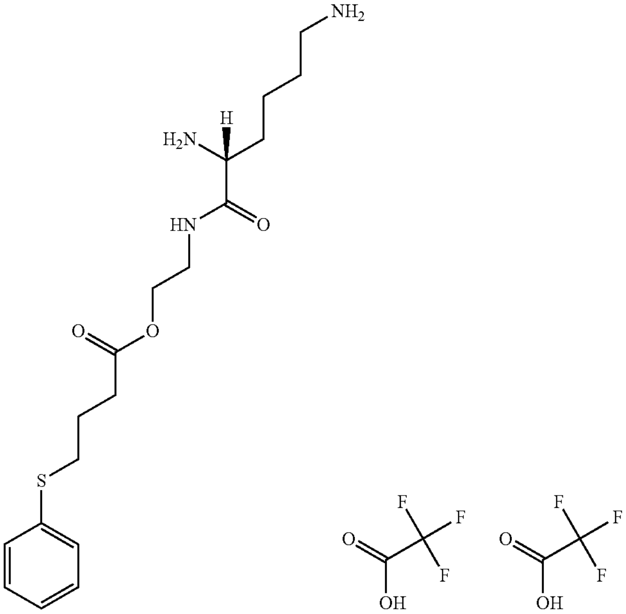 | 367.5 | C18H29N3O3S• C2HO2F3• C2HO2F3 |

TABLE 1-continued

| Compound | Structure | MW | Molecular Formula |
| --- | --- | --- | --- |
| 24 | 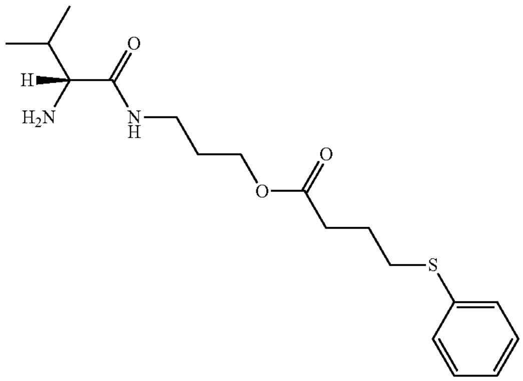 [SMILES: CC(C)[C@@H](N)C(=O)NCCCOC(=O)CCCSc1ccccc1] | 352.5 | C18H28N2O3S |

Furthermore, all compounds of the present disclosure which exist in free base or acid form can be converted to their pharmaceutically acceptable salts by treatment with the appropriate inorganic or organic base or acid by methods known to one skilled in the art. Salts of the compounds of the present disclosure can be converted to their free base or acid form by standard techniques.

Some embodiments include or involve co-administration of a platinum-based drug and a (pharmaceutical) composition comprising a pharmaceutically acceptable carrier or excipient and a compound of Formula I.

Some embodiments include or involve co-administration of a platinum-based drug and a (pharmaceutical) medicament comprising a pharmaceutically acceptable carrier or excipient and a compound of Formula I or composition comprising the same.

Some embodiments include or involve co-administration of a platinum-based drug and a composition or medicament including a compound of Formula I for use in (i) treating cancer, (ii) treating tumors, (iii) treating lung cancer, (iv) treatment of AKI, (v) treating Lewis Lung Carcinoma, and/or (vi) treating other related conditions or affecting other related molecular mechanisms, in a mammal or mammalian subject (in need thereof). In some embodiments, the mammal or mammalian subject is human.

Some embodiments are directed to use of a platinum-based drug and the compound of Formula I, a pharmaceutical compositions comprising the same, or a medicament comprising the same, for (i) treating cancer, (ii) treating tumors, (iii) treating lung cancer, (iv) treatment of AKI, (v) treating Lewis Lung Carcinoma, and/or (vi) treating other related conditions or affecting other related molecular mechanisms, in a mammal or mammalian subject (in need thereof). In some embodiments, the mammal or mammalian subject is human.

Some embodiments are directed to a method of (i) treating cancer, (ii) treating tumors, (iii) treating lung cancer, (iv) treatment of AKI, (v) treating Lewis Lung Carcinoma, and/or (vi) treating other related conditions or affecting other related molecular mechanisms, in a mammal or mammalian subject (in need thereof), the method comprising co-administering a platinum-based drug and a compound according to Formula I, a pharmaceutical compositions comprising the same, or a medicament comprising the same, to the mammal or mammalian subject (in need thereof). In some embodiments, the mammal or mammalian subject is human.

Some embodiments may include any of the features, options, and/or possibilities set out elsewhere in the present disclosure, including in other aspects or embodiments of the present disclosure. It is also noted that each of the foregoing, following, and/or other features described herein represent a distinct embodiment of the present disclosure. Moreover, combinations of any two or more of such features represent distinct embodiments of the present disclosure. Such features or embodiments can also be combined in any suitable combination and/or order without departing from the scope of this disclosure. Thus, each of the features described herein can be combinable with any one or more other features described herein in any suitable combination and/or order. Accordingly, the present disclosure is not limited to the specific combinations of exemplary embodiments described in detail herein.

Additional features and advantages of exemplary embodiments of the present disclosure will be set forth in the description that follows, and in part will be obvious from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other advantages and features of the present disclosure can be obtained, a more particular description of the embodiments briefly described above will be rendered by reference to specific embodiments thereof which are illustrated in the appended drawings. For better understanding, the like elements have been designated by like reference numbers throughout the figure(s). Understanding that these drawings depict only typical embodiments of the disclosure and are not therefore to be considered to be limiting of its scope, the disclosure will be described and explained with additional specificity and detail through the use of the accompanying drawing(s) in which.

DETAILED DESCRIPTION

Definitions and Disclaimers

Figure 1:
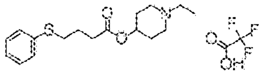
FIG. 1 depicts 24 illustrative compounds and information associated with the same.
Figure 1:
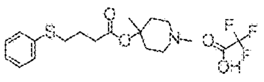
Figure 1:
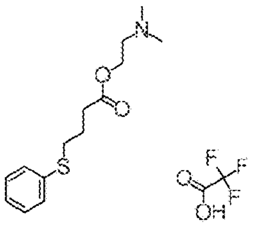
Figure 1:
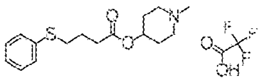
Figure 1:
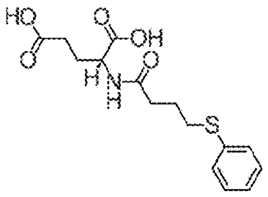
Figure 1:
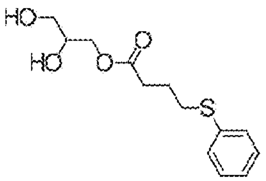
Figure 1:
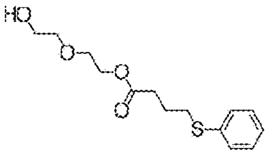
Figure 1:
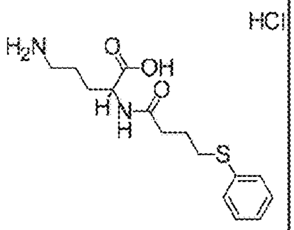
Figure 1:
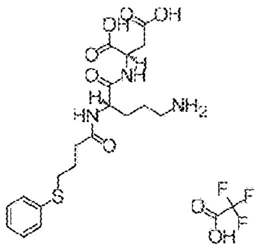
Figure 1:
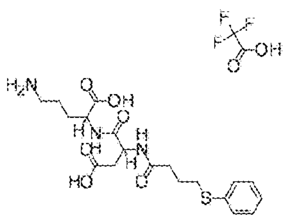
Figure 1:
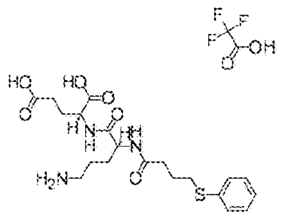
Figure 1:
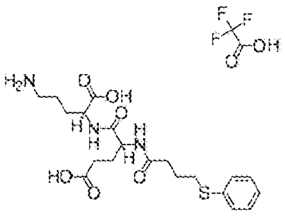
Figure 1:
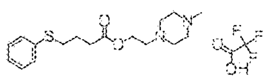
Figure 1:
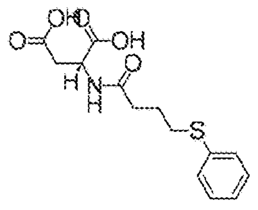
Figure 1:
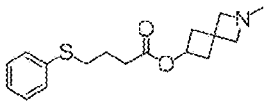
Figure 1:
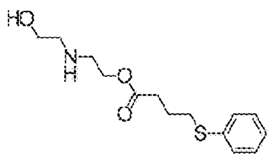
Figure 1:
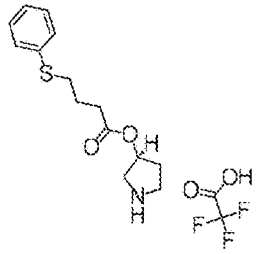
Figure 1:
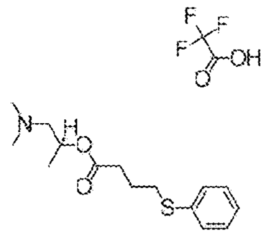
Figure 1:
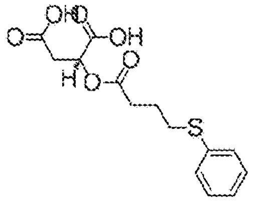
Figure 1:
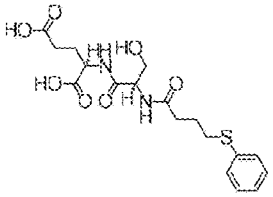
Figure 1:
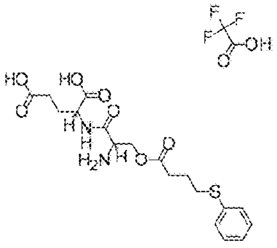
Figure 1:
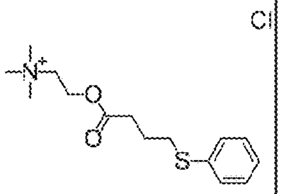
Figure 1:
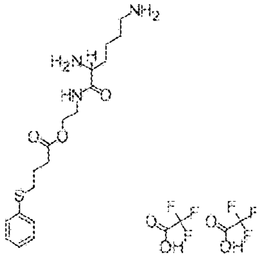
Figure 1:
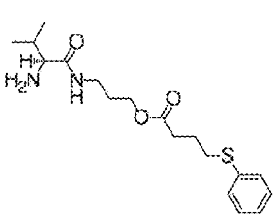

Before describing various embodiments of the present disclosure in detail, it is to be understood that this disclosure is not limited only to the specific parameters, verbiage, and description of the particularly exemplified systems, methods, and/or products that may vary from one embodiment to the next. Thus, while certain embodiments of the present disclosure will be described in detail, with reference to specific features (e.g., configurations, parameters, properties, steps, components, ingredients, members, elements, parts, and/or portions, etc.), the descriptions are illustrative and are not to be construed as limiting the scope of the present disclosure and/or the claimed invention. In addition, the terminology used herein is for the purpose of describing the embodiments, and is not necessarily intended to limit the scope of the present disclosure and/or the claimed invention.

Unless defined otherwise, all technical and scientific terms used herein have the same meaning as commonly understood by one of ordinary skill in the art to which the present disclosure pertains.

Various "aspects" of the present disclosure, including systems, methods, and/or products may be illustrated with reference to one or more "embodiments," which are exemplary in nature. As used herein, the terms "aspect" and "embodiment" may be used interchangeably. The term "embodiment" can also mean "serving as an example, instance, or illustration," and should not necessarily be construed as preferred or advantageous over other aspects disclosed herein. In addition, reference to an "embodiment" of the present disclosure or invention is intended to provide an illustrative example without limiting the scope of the invention, which is indicated by the appended claims.

As used in this specification and the appended claims, the singular forms "a," "an" and "the" each contemplate, include, and specifically disclose both the singular and plural referents, unless the context clearly dictates otherwise. For example, reference to a "protein" contemplates and specifically discloses one, as well as a plurality of (e.g., two or more, three or more, etc.) proteins. Similarly, use of a plural referent does not necessarily require a plurality of such referents, but contemplates, includes, specifically discloses, and/or provides support for a single, as well as a plurality of such referents, unless the context clearly dictates otherwise.

As used throughout this disclosure, the words "can" and "may" are used in a permissive sense (i.e., meaning having the potential to), rather than the mandatory sense (i.e., meaning must). Additionally, the terms "including," "having," "involving," "containing," "characterized by," variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

The term "condition" refers to any disorder, disease, injury, or illness, as understood by those skilled in the art, that is manifested or anticipated in a patient. Manifestation of such a condition can be an early, middle, or late stage manifestation, as known in the art, including pre-condition symptoms, signs, or markers. Anticipation of such a condition can be or include the predicted, expected, envisioned, presumed, supposed, and/or speculated occurrence of the same, whether founded in scientific or medical evidence, risk assessment, or mere apprehension or trepidation.

The term "patient," as used herein, is synonymous with the term "subject" and generally refers to any animal under the care of a medical professional, as that term is defined herein, with particular reference to (i) humans (under the care of a doctor, nurse, or medical assistant or volunteer) and (ii) non-human animals, such as non-human mammals (under the care of a veterinarian or other veterinary professional, assistant, or volunteer).

The term "prodrug" is meant to indicate a compound that may be converted under physiological conditions or by solvolysis to a biologically active compound described herein (e.g., compound according to Formula I). Thus, the term "prodrug" refers to a precursor of a biologically active compound that is pharmaceutically acceptable. In some aspects, a prodrug is or may be inactive/less-active when administered to a subject, but is converted in vivo to an active compound, for example, by hydrolysis. The prodrug compound often offers advantages of solubility, tissue compatibility or delayed release in a mammalian organism (see, e.g., Jornada et al., “The Prodrug Approach: A Successful Tool for Improving Drug Solubility,” Molecules 2016, 21, 42, the entirety of which is incorporated herein by specific reference). A discussion of prodrugs is provided in Higuchi, T., et al., “Pro-drugs as Novel Delivery Systems,” A.C.S. Symposium Series, Vol. 14, and in Laksitorini et al., “Pathways and progress in improving drug delivery through the intestinal mucosa and blood-brain barriers,” Ther. Deliv. (2014) 5(10), 1143-1163, the entirety of each of which is incorporated herein by specific reference.

Embodiments of the present disclosure are also meant to encompass all pharmaceutically acceptable compounds according to Formula I that are isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, C, $^{13}C$, C, $^{13}N$, $^{5}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds may be useful to help determine or measure the effectiveness of the compounds, by characterizing, for example, the site or mode of action, or binding affinity to pharmacologically important site of action. Certain isotopically-labelled compounds according to Formula I, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula I can generally be prepared by conventional techniques known to those skilled in the art or by processes analogous to those described in the Preparations and Examples as set out below using an appropriate isotopically-labeled reagent in place of the non-labeled reagent previously employed.

Embodiments of the present disclosure may also encompass the in vivo metabolic products of the disclosed compounds. Such products may result from, for example, the oxidation, reduction, hydrolysis, amidation, esterification, and the like of the administered compound, primarily due to enzymatic processes. Accordingly, embodiments of the present disclosure include compounds produced by a process comprising administering a compound of this present disclosure to a mammal for a period of time sufficient to yield a metabolic product thereof. Such products are typically identified by administering a radiolabeled compound of the present disclosure in a detectable dose to an animal, such as rat, mouse, guinea pig, monkey, or to human, allowing sufficient time for metabolism to occur, and isolating its conversion products from the urine, blood or other biological samples.

The term(s) “carrier, diluent and/or excipient,” as well as “pharmaceutically acceptable carrier, diluent and/or excipient” include, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The term “salt” or “pharmaceutically acceptable salt” includes both acid and base addition salts.

Salts may include “acid addition salt” or “pharmaceutically acceptable acid addition salt”, which refer to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

Salts may include “base addition salt” or “pharmaceutically acceptable base addition salt”, which refer to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the present disclosure. As used herein, the term “solvate” refers to an aggregate that comprises one or more molecules of a compound of the present disclosure with one or more molecules of solvent. The solvent may be water, in which case the solvate may be a hydrate. Alternatively, the solvent may be an organic solvent. Thus, embodiments of the compounds of the present disclosure may exist as a hydrate, including a monohydrate, dihydrate, hemihydrate, sesquihydrate, trihydrate, tetrahydrate and the like, as well as the corresponding solvated forms. Embodiments of the compound of the present disclosure may be true solvates, while in other cases, the compound of the present disclosure may merely retain adventitious water or be a mixture of water plus some adventitious solvent.

A "pharmaceutical composition" refers to a formulation of a compound of the present disclosure and a medium generally accepted in the art for the delivery of the biologically active compound to mammals, e.g., humans. Such a medium includes all pharmaceutically acceptable carriers, diluents or excipients therefor.

"Mammal" includes humans and both domestic animals such as laboratory animals and household pets (e.g., cats, dogs, swine, cattle, sheep, goats, horses, rabbits), and non-domestic animals such as wildlife and the like.

"Effective amount" or "therapeutically effective amount" refers to that amount of a compound of the present disclosure which, when administered to a mammal, preferably a human, is sufficient to effect treatment, as defined below, of a disease or condition (e.g., cancer or tumor cells, or AKI) in the mammal, preferably a human. The amount of a compound of the present disclosure which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

Compounds of the present disclosure, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. Embodiments of the present disclosure contemplate various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. Embodiments of the present disclosure include tautomers of any said compounds.

For the sake of brevity, the present disclosure may recite a list or range of numerical values. It will be appreciated, however, that where such a list or range of numerical values (e.g., greater than, less than, up to, at least, and/or about a certain value, and/or between two recited values) is disclosed or recited, any specific value or range of values falling within the disclosed values or list or range of values is likewise specifically disclosed and contemplated herein.

To facilitate understanding, like references (i.e., like naming of components and/or elements) have been used, where possible, to designate like elements common to different embodiments of the present disclosure. Similarly, like components, or components with like functions, will be provided with similar reference designations, where possible. Specific language will be used herein to describe the exemplary embodiments. Nevertheless it will be understood that no limitation of the scope of the disclosure is thereby intended. Rather, it is to be understood that the language used to describe the exemplary embodiments is illustrative only and is not to be construed as limiting the scope of the disclosure (unless such language is expressly described herein as essential).

While the detailed description is separated into sections, the section headers and contents within each section are for organizational purposes only and are not intended to be self-contained descriptions and embodiments or to limit the scope of the description or the claims. Rather, the contents of each section within the detailed description are intended to be read and understood as a collective whole, where elements of one section may pertain to and/or inform other sections. Accordingly, embodiments specifically disclosed within one section may also relate to and/or serve as additional and/or alternative embodiments in another section having the same and/or similar products, methods, and/or terminology.

Provided herein are compounds useful for improving kidney function, inhibiting a histone deacetylase in a cell, expanding renal progenitor cells and/or stimulating kidney repair in cells in vitro, ex vivo or in vivo (in a patient). Compositions and medicaments are also provided for delivery of the compounds to a patient. Also provided are methods for improving kidney function, inhibiting a histone deacetylase in a cell, expanding renal progenitor cells and/or stimulating kidney repair in cells in vitro, ex vivo or in vivo (in a patient) comprising contacting the cells with, or administering to a patient an amount of one or more of the compounds effective to improve kidney function in a patient, inhibit a histone deacetylase in a cell, expand renal progenitor cells and/or stimulate kidney repair in cells. Therefore provided are in vitro (including ex vivo) or in vivo (in a patient) methods. Efficacy of the compounds is demonstrated below.

Compounds

Embodiments of the present disclosure include prodrugs of PTBA. Illustrative embodiments of the present disclosure include a compound according to Formula I:

Formula I

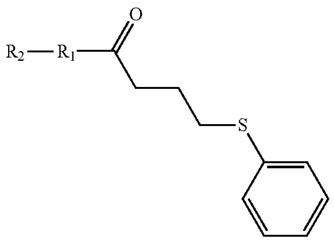

or a stereoisomer, tautomer or pharmaceutically acceptable salt thereof. In various embodiments, $R_1$ is O or NH. In some embodiments, $R_1$ is O. In some embodiments, $R_1$ is NH.

In some embodiments, $R_2$ is not H. In some embodiments, $R_2$ is not $CH_3$. In some embodiments, $R_2$ is not, one or more of, alkyl, ethyl, propyl, isopropyl, or butyl. In some embodiments, $R_2$ is not aryl, phenyl or benzyl. In some embodiments, $R_2$ is not carboxyl (COOH). In some embodiments, $R_2$ is not, one or more of, methanol, ethanol, propanol, or isopropanol.

In various embodiments, $R_2$ is one of:

substituted or unsubstituted amine, preferably substituted or unsubstituted tertiary amine or quaternary amine (trisubstituted ammonium or quaternary ammonium), more preferably 1-(N,N-dimethyl)ethanamine, 1-(1-methyl-N,N-dimethyl)ethanamine, or 1-(N,N,N-trimethyl)ethanamine, substituted or unsubstituted heterocyclic amine or azaspiroalkyl (or hetero-dualcycloalkyl), preferably 5-7 member heterocyclic amine or azaspiroalkyl, optionally substituted at one or more ring positions with C1-C2 alkyl, or 4-7 member substituted or unsubstituted heterocycloalkyl or hetero-dualcycloalkyl (a.k.a. azaspiroalkyl), optionally substituted at 1-4 (ring) positions and each (ring) substituent is one of branched or unbranched C1-C3 substituted or unsubstituted alkyl or cycloalkyl, more preferably substituted or unsubstituted pyrrolidine, piperidine, or piperazine, still more preferably, substituted or unsubstituted 3-N-pyrrolidine, 4-N-piperidine, or 4-N-piperazine, still more preferably, 4-N-piperidine or 4-N-piperazine substituted at C-1, N-4, or C-1 and N-4, still more preferably, 4-N-methylpiperidine, 4-N-ethylpiperidine, 4-N-1,4-methylpiperidine, 4-N-methylpiperazine, or substituted or unsubstituted azaspiroheptyl, preferably 2-azaspiroheptyl or azaspiro[3.3]heptyl, still more preferably 2-azaspiro[3.3]heptyl, still more preferably 2-methyl-2-azaspiro[3.3]heptyl, alkanolamine, preferably ethanolamine, more preferably N-ethylethanolamine or 2-(ethylamino)ethanol, alkoxyalcohol, preferably alkoxy ethanol or ethoxy alcohol, more preferably 2-ethoxyethanol, polyol, preferably diol, more preferably propanediol, still more preferably 2,3-propanediol, carboxylic acid, preferably dicarboxylic acid, more preferably butanedioic acid, still more preferably, butanedioic acid, amide, preferably substituted amide, more preferably N-ethyl-N-amide, N-propyl-N-amide, or 2-amino-propanamide, still more preferably 2,6-diamino-N-ethyl-N-hexanamide, 2-amino-3-methyl-N-propyl-N-butanamide, or N-(1,3-dicarboyl)-2-amino-propanamide, or wherein the amide comprises:

—$R_3$—C(═O)NH—$R_4$, wherein $R_3$ is substituted alkyl, preferably substituted ethyl, more preferably amino ethyl, still more preferably 2-amino ethyl, and $R_4$ is carboxylic acid, preferably dicarboxylic acid, more preferably pentanedioic acid, still more preferably, pentanedioic acid or pentanedioic acid, or —$R_5$—NHC(═O)—$R_6$, wherein $R_5$ is substituted alkyl, ethyl or propyl, and $R_6$ is substituted alkyl, preferably 1-amino-2-methylpropane or 1,5-diaminopentane, branched or unbranched C2-C10 substituted or unsubstituted alkyl, amine, amide, acetyl, aldehyde, alkoxy (ether), ester, carbonyl, carboxyl, carbamate, diol, triol, trisubstituted ammonium, optionally substituted at 1-5 positions and each substituent is one of branched or unbranched C1-C5 substituted or unsubstituted alkyl, amine, amide, acetyl, aldehyde, alkoxy (ether), hydroxy, ester, carbonyl, carboxyl, carbamate, diol, triol, trisubstituted ammonium, —X—$R_7$, wherein X is C1-C3 branched or unbranched alkyl, and wherein $R_7$ is a 4-7 member substituted or unsubstituted heterocycloalkyl or hetero-dualcycloalkyl (a.k.a. azaspiroalkyl), optionally substituted at 1-4 (ring) positions and each (ring) substituent is one of branched or unbranched C1-C3 substituted or unsubstituted alkyl or cycloalkyl, preferably substituted or unsubstituted pyrrolidine, piperidine, or piperazine, more preferably, substituted or unsubstituted 3-N-pyrrolidine, 4-N-piperidine, or 4-N-piperazine, still more preferably, 4-N-piperidine or 4-N-piperazine substituted at C-1, N-4, or C-1 and N-4, still more preferably, 4-N-methylpiperidine, 4-N-ethylpiperidine, 4-N-1,4-methylpiperidine, 4-N-methylpiperazine, most preferably, 4-N-methylpiperazine, preferably when X is $(CH_2)_2$, or tertiary amine or quaternary amine (trisubstituted ammonium or quaternary ammonium), more preferably 1-(N,N-dimethyl)ethanamine, 1-(1-methyl-N,N-dimethyl)ethanamine, or 1-(N,N,N-trimethyl) ethanamine, branched or unbranched C2-C10 substituted or unsubstituted alkyl, amine, amide, acetyl, aldehyde, alkoxy (ether), ester, carbonyl, carboxyl, carbamate, diol, triol, trisubstituted ammonium, optionally substituted at 1-5 positions and each substituent is one of branched or unbranched C1-C5 substituted or unsubstituted alkyl, amine, amide, acetyl, aldehyde, alkoxy (ether), hydroxy, ester, carbonyl, carboxyl, carbamate, diol, triol, trisubstituted ammonium, —$(CR_8R_9)_Z$—$R_{10}$, wherein Z is an integer from 1-3, each $R_8$ is, independently, one of H or $CH_3$, each $R_9$ is, independently, selected from: H, hydroxyl (OH), carboxyl (COOH), amino ($NH_2$), or together with $R_{10}$, forms substituted or unsubstituted heterocyclic amine or azaspiroalkyl (or hetero-dualcycloalkyl), preferably 5-7 member heterocyclic amine or azaspiroalkyl, optionally substituted at one or more ring positions with C1-C2 alkyl, more preferably 5-6 member heterocyclic amine or 7 member azaspiroalkyl, optionally substituted at one or more ring positions with C1-C2 alkyl, substituted or unsubstituted pyrrolidine, piperidine, or piperazine, still more preferably, substituted or unsubstituted 3-N-pyrrolidine, 4-N-piperidine, or 4-N-piperazine, still more preferably unsubstituted 3-N-pyrrolidine or substituted 4-N-piperidine or 4-N-piperazine, substituted at C-1, N-4, or C-1 and N-4, still more preferably, 4-N-methylpiperidine, 4-N-ethylpiperidine, 4-N-1,4-methylpiperidine, or 4-N-methyl-1-piperazine, or substituted or unsubstituted azaspiroheptyl, preferably substituted or unsubstituted 2-azaspiroheplyl or azaspiro[3.3]heptyl, still more preferably substituted or unsubstituted 2-azaspiro[3.3]heptyl, still more preferably 2-methyl-2-azaspiro[3.3]heptyl, and each $R_{10}$ is, independently, one of:

amine, preferably tertiary amine or quaternary amine (trisubstituted ammonium or quaternary ammonium), more preferably 1-(N,N-dimethyl)amine, 1-(1-methyl-N,N-dimethyl)amine, or 1-(N,N,N-trimethyl)amine, optionally substituted heterocyclic amine, preferably 6 member heterocyclic amine, still more preferably 6 member heterocyclic amine, still more preferably piperazine, still more preferably, 4-N-piperazine, still more preferably 4-N-methylpiperazine or 4-N-methyl-1-piperazine, alkanolamine, preferably ethanolamine, N-ethanolamine or 1-aminoethanol, alkoxyalcohol, preferably alkoxy ethanol or ethoxy alcohol, polyol, preferably diol, more preferably ethanediol, carboxyl (COOH), amide, preferably substituted amide, more preferably substituted N-pentanamide, N-hexanamide, or 1-amide, more preferably 2,6-diamino-N-hexanamide, 2-amino-3-methyl-N-butanamide, or N-(1,3-dicarboyl)-2-amino-1-amide, or wherein the amide comprises:

—C(=O)NH—Ru, wherein $R_4$ is carboxylic acid, preferably dicarboxylic acid, more preferably pentanedioic acid, still more preferably, pentanedioic acid or pentanedioic acid, or —NHC(=O)—$R_{12}$, wherein $R_{12}$ is substituted alkyl, preferably 1-amino-2-methylpropane or 1,5-diaminopentane, together with $R_9$, forms substituted or unsubstituted heterocyclic amine or azaspiroalkyl (or hetero-dualcycloalkyl), preferably 5-7 member heterocyclic amine or azaspiroalkyl, optionally substituted at one or more ring positions with C1-C2 alkyl, more preferably 5-6 member heterocyclic amine or 7 member azaspiroalkyl, optionally substituted at one or more ring positions with C1-C2 alkyl, substituted or unsubstituted pyrrolidine, piperidine, or piperazine, still more preferably, substituted or unsubstituted 3-N-pyrrolidine, 4-N-piperidine, or 4-N-piperazine, still more preferably unsubstituted 3-N-pyrrolidine or substituted 4-N-piperidine or 4-N-piperazine, substituted at C-1, N-4, or C-1 and N-4, still more preferably, 4-N-methylpiperidine, 4-N-ethylpiperidine, 4-N-1,4-methylpiperidine, or 4-N-methyl-1-piperazine, or substituted or unsubstituted azaspiroheptyl, preferably substituted or unsubstituted 2-azaspiroheplyl or azaspiro[3.3]heptyl, still more preferably substituted or unsubstituted 2-azaspiro[3.3]heptyl, still more preferably 2-methyl-2-azaspiro[3.3]heptyl, or —$(CR_{13}R_{14})_z$—$R_{15}$, wherein each $R_{13}$ is H, each $R_{14}$ is, independently, one of H, $CH_3$, carboxyl (COOH), ethanol ($CH_2OH$), preferably 2-ethanol, amine or alkylamine, preferably propylamine, carboxylic acid, preferably ethanoic acid or propanoic acid, Z is and integer from 1-3, and $R_{15}$ is carboxyl (—COOH), amino (—$NH_2$), or amide, preferably 1-amide, more preferably N-substituted-1-amide (or N-substituted carboxamide) (—CONH—$R_{16}$, where $R_{16}$ is substituted alkyl, preferably 1,3-dicarboxypropane, 1-(1-carboxy)butyric acid or butanedioic acid, 1-carboxy-2-pentanoic acid or pentanedioic acid, preferably 2-pentanedioic acid, or 2-(3-aminopropyl)ethanoic acid.

In some embodiments, when $R_1$ is O, then $R_2$ is one of:

substituted or unsubstituted amine, preferably substituted or unsubstituted tertiary amine or quaternary amine (trisubstituted ammonium or quaternary ammonium), more preferably 1-(N,N-dimethyl)ethanamine, 1-(1-methyl-N,N-dimethyl)ethanamine, or 1-(N,N,N-trimethyl)ethanamine, substituted or unsubstituted heterocyclic amine or azaspiroalkyl (or hetero-dualcycloalkyl), preferably 5-7 member heterocyclic amine or azaspiroalkyl, optionally substituted at one or more ring positions with C1-C2 alkyl, or 4-7 member substituted or unsubstituted heterocycloalkyl or hetero-dualcycloalkyl (a.k.a. azaspiroalkyl), optionally substituted at 1-4 (ring) positions and each (ring) substituent is one of branched or unbranched C1-C3 substituted or unsubstituted alkyl or cycloalkyl, more preferably substituted or unsubstituted pyrrolidine, piperidine, or piperazine, still more preferably, substituted or unsubstituted 3-N-pyrrolidine, 4-N-piperidine, or 4-N-piperazine, still more preferably, 4-N-piperidine or 4-N-piperazine substituted at C-1, N-4, or C-1 and N-4, still more preferably, 4-N-methylpiperidine, 4-N-ethylpiperidine, 4-N-1,4-methylpiperidine, 4-N-methylpiperazine, or substituted or unsubstituted azaspiroheptyl, preferably 2-azaspiroheptyl or azaspiro[3.3]heptyl, still more preferably 2-azaspiro[3.3]heptyl, still more preferably 2-methyl-2-azaspiro[3.3]heptyl, alkanolamine, preferably ethanolamine, more preferably N-ethylethanolamine or 2-(ethylamino)ethanol, alkoxyalcohol, preferably alkoxy ethanol or ethoxy alcohol, more preferably 2-ethoxyethanol, polyol, preferably diol, more preferably propanediol, still more preferably 2,3-propanediol, carboxylic acid, preferably dicarboxylic acid, more preferably butanedioic acid, still more preferably, butanedioic acid or butanedioic acid, amide, preferably substituted amide, more preferably N-ethyl-N-amide, N-propyl-N-amide, or 2-amino-propanamide, still more preferably 2,6-diamino-N-ethyl-N-hexanamide, 2-amino-3-methyl-N-propyl-N-butanamide, or N-(1,3-dicarboyl)-2-amino-propanamide, or wherein the amide comprises:

—$R_3$—C(=O)NH—$R_4$, wherein $R_3$ is substituted alkyl, preferably substituted ethyl, more preferably amino ethyl, still more preferably 2-amino ethyl, and $R_4$ is carboxylic acid, preferably dicarboxylic acid, more preferably pentanedioic acid, still more preferably, pentanedioic acid or pentanedioic acid, —$R_5$—NHC(=O)—$R_6$, wherein $R_8$ is substituted alkyl, ethyl or propyl, and $R_6$ is substituted alkyl, preferably 1-amino-2-methylpropane or 1,5-diaminopentane, branched or unbranched C2-C10 substituted or unsubstituted alkyl, amine, amide, acetyl, aldehyde, alkoxy (ether), ester, carbonyl, carboxyl, carbamate, diol, triol, trisubstituted ammonium, optionally substituted at 1-5 positions and each substituent is one of branched or unbranched C1-C5 substituted or unsubstituted alkyl, amine, amide, acetyl, aldehyde, alkoxy (ether), hydroxy, ester, carbonyl, carboxyl, carbamate, diol, triol, trisubstituted ammonium, or —X—$R_7$, wherein X is C1-C3 branched or unbranched alkyl, and wherein $R_7$ is a 4-7 member substituted or unsubstituted heterocycloalkyl or hetero-dualcycloalkyl (a.k.a. azaspiroalkyl), optionally substituted at 1-4 (ring) positions and each (ring) substituent is one of branched or unbranched C1-C3 substituted or unsubstituted alkyl or cycloalkyl, preferably substituted or unsubstituted pyrrolidine, piperidine, or piperazine, more preferably, substituted or unsubstituted 3-N-pyrrolidine, 4-N-piperidine, or 4-N-piperazine, still more preferably, 4-N-piperidine or 4-N-piperazine substituted at C-1, N-4, or C-1 and N-4, still more preferably, 4-N-methylpiperidine, 4-N-ethylpiperidine, 4-N-1,4-methylpiperidine, 4-N-methylpiperazine, most preferably, 4-N-methylpiperazine, preferably when X is $(CH_2)_2$, or tertiary amine or quaternary amine (trisubstituted ammonium or quaternary ammonium), more preferably 1-(N,N-dimethyl)ethanamine, 1-(1-methyl-N,N-dimethyl)ethanamine, or 1-(N,N,N-trimethyl)ethanamine, branched or unbranched C2-C10 substituted or unsubstituted alkyl, amine, amide, acetyl, aldehyde, alkoxy (ether), ester, carbonyl, carboxyl, carbamate, diol, triol, trisubstituted ammonium, optionally substituted at 1-5 positions and each substituent is one of branched or unbranched C1-C5 substituted or unsubstituted alkyl, amine, amide, acetyl, aldehyde, alkoxy (ether), hydroxy, ester, carbonyl, carboxyl, carbamate, diol, triol, trisubstituted ammonium.

In some embodiments, when $R_1$ is O, then $R_2$ is one of:

substituted or unsubstituted amine, preferably substituted or unsubstituted tertiary amine or quaternary amine (trisubstituted ammonium or quaternary ammonium), more preferably 1-(N,N-dimethyl)ethanamine, 1-(1-methyl-N,N-dimethyl)ethanamine, or 1-(N,N,N-trimethyl)ethanamine, substituted or unsubstituted heterocyclic amine or azaspiroalkyl, preferably 5-7 member heterocyclic amine or azaspiroalkyl, optionally substituted at one or more ring positions with C1-C2 alkyl, alkanolamine, preferably ethanolamine, more preferably N-ethylethanolamine or 2-(ethylamino)ethanol, alkoxyalcohol, preferably alkoxy ethanol or ethoxy alcohol, more preferably 2-ethoxyethanol, polyol, preferably diol, more preferably propanediol, still more preferably 2,3-propanediol, carboxylic acid, preferably dicarboxylic acid, more preferably butanedioic acid, still more preferably, butanedioic acid or butanedioic acid, amide, preferably substituted amide, more preferably N-ethyl-N-amide, N-propyl-N-amide, or 2-amino-propanamide, still more preferably 2,6-diamino-N-ethyl-N-hexanamide, 2-amino-3-methyl-N-propyl-N-butanamide, or N-(1,3-dicarboyl)-2-amino-propanamide, or wherein the amide comprises:

—$R_3$—C(═O)NH—$R_4$, wherein $R_3$ is substituted alkyl, preferably substituted ethyl, more preferably amino ethyl, still more preferably 2-amino ethyl, and $R_4$ is carboxylic acid, preferably dicarboxylic acid, more preferably pentanedioic acid, still more preferably, pentanedioic acid or pentanedioic acid, or —$R_5$—NHC(═O)—$R_6$, wherein $R_5$ is one of substituted alkyl, ethyl or propyl, and $R_6$ is substituted alkyl, preferably 1-amino-2-methylpropane or 1,5-diaminopentane.

In some embodiments, when $R_1$ is O, then $R_2$ is $(CR_8R_9)_z$—$R_{10}$, wherein:

Z is an integer from 1-3, each $R_8$ is, independently, H or $CH_3$, each $R_9$ is, independently, one of: H, hydroxyl (OH), carboxyl (COOH), amino ($NH_2$), or together with $R_{10}$, forms substituted or unsubstituted heterocyclic amine or azaspiroalkyl (or hetero-dualcycloalkyl), preferably 5-7 member heterocyclic amine or azaspiroalkyl, optionally substituted at one or more ring positions with C1-C2 alkyl, more preferably 5-6 member heterocyclic amine or 7 member azaspiroalkyl, optionally substituted at one or more ring positions with C1-C2 alkyl, substituted or unsubstituted pyrrolidine, piperidine, or piperazine, still more preferably, substituted or unsubstituted 3-N-pyrrolidine, 4-N-piperidine, or 4-N-piperazine, still more preferably unsubstituted 3-N-pyrrolidine or substituted 4-N-piperidine or 4-N-piperazine, substituted at C-1, N-4, or C-1 and N-4, still more preferably, 4-N-methylpiperidine, 4-N-ethylpiperidine, 4-N-1,4-methylpiperidine, or 4-N-methyl-1-piperazine, or substituted or unsubstituted azaspiroheptyl, preferably substituted or unsubstituted 2-azaspiroheptyl or azaspiro[3.3]heptyl, still more preferably substituted or unsubstituted 2-azaspiro[3.3]heptyl, still more preferably 2-methyl-2-azaspiro[3.3]heptyl, and each $R_{10}$ is, independently, one of:

amine, preferably tertiary amine or quaternary amine (trisubstituted ammonium or quaternary ammonium), more preferably 1-(N,N-dimethyl)amine, 1-(1-methyl-N,N-dimethyl)amine, or 1-(N,N,N-trimethyl)amine, optionally substituted heterocyclic amine, preferably 6 member heterocyclic amine, still more preferably 6 member heterocyclic amine, still more preferably piperazine, still more preferably, 4-N-piperazine, still more preferably 4-N-methylpiperazine or 4-N-methyl-1-piperazine, alkanolamine, preferably ethanolamine, N-ethanolamine or 1-aminoethanol, alkoxyalcohol, preferably alkoxy ethanol or ethoxy alcohol, polyol, preferably diol, more preferably ethanediol, carboxyl (COOH), amide, preferably substituted amide, more preferably substituted N-pentanamide, N-hexanamide, or 1-amide, more preferably 2,6-diamino-N-hexanamide, 2-amino-3-methyl-N-butanamide, or N-(1,3-dicarboyl)-2-amino-1-amide, or wherein the amide comprises:

—C(═O)NH—$R_{11}$, wherein $R_4$ is carboxylic acid, preferably dicarboxylic acid, more preferably pentanedioic acid, still more preferably, pentanedioic acid or pentanedioic acid, or —NHC(═O)—$R_{12}$, wherein $R_{12}$ is substituted alkyl, preferably 1-amino-2-methylpropane or 1,5-diaminopentane, or together with $R_9$, forms substituted or unsubstituted heterocyclic amine or azaspiroalkyl (or hetero-dual-cycloalkyl), preferably 5-7 member heterocyclic amine or azaspiroalkyl, optionally substituted at one or more ring positions with C1-C2 alkyl, more preferably 5-6 member heterocyclic amine or 7 member azaspiroalkyl, optionally substituted at one or more ring positions with C1-C2 alkyl, substituted or unsubstituted pyrrolidine, piperidine, or piperazine, still more preferably, substituted or unsubstituted 3-N-pyrrolidine, 4-N-piperidine, or 4-N-piperazine, still more preferably unsubstituted 3-N-pyrrolidine or substituted 4-N-piperidine or 4-N-piperazine, substituted at C-1, N-4, or C-1 and N-4, still more preferably, 4-N-methylpiperidine, 4-N-ethylpiperidine, 4-N-1,4-methylpiperidine, or 4-N-methyl-1-piperazine, or substituted or unsubstituted azaspiroheptyl, preferably substituted or unsubstituted 2-azaspiroheptyl or azaspiro[3.3]heptyl, still more preferably substituted or unsubstituted 2-azaspiro[3.3]heptyl, still more preferably 2-methyl-2-azaspiro[3.3]heptyl, In some embodiments, when $R_1$ is O, then $R_2$ is one of Formulas Ia-Ip:

Formula Ia

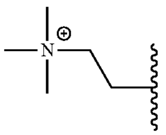

Formula Ib

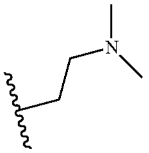

Formula Ic

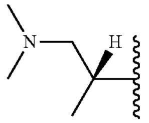

Formula Id

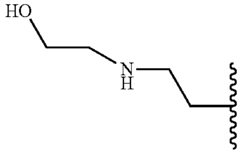

Formula Ie

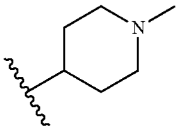

Formula If

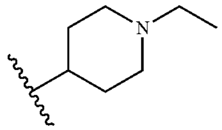

Formula Ig

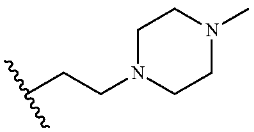

-continued

Formula Ih

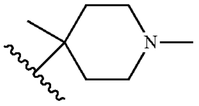

Formula Ii

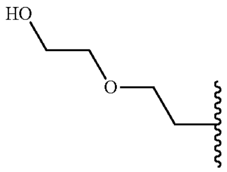

Formula Ij

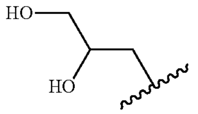

Formula Ik

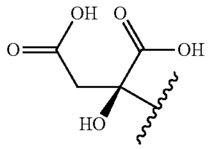

Formula Il

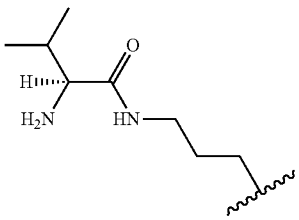

Formula Im

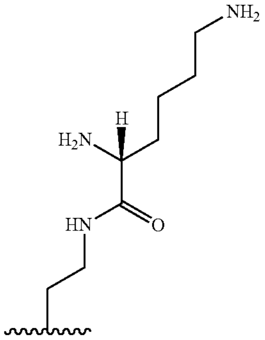

Formula In

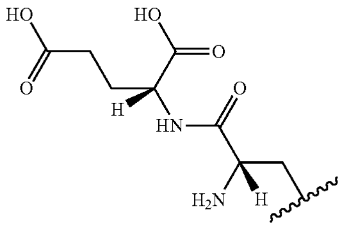

Formula Io

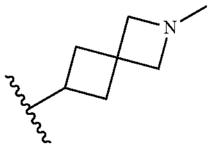

-continued

Formula Ip

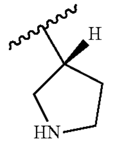

In some embodiments, when $R_1$ is O, then $R_2$ is $CR_{17}R_{18})_2$—$R_{19}$, wherein each $R_{17}$ is H and each $R_{18}$ is, independently, H or $CH_3$; and $R_{19}$ is $N(CH_3)_Y$, wherein Y is an integer from 2-3.

In some embodiments, when $R_1$ is O, then $R_2$ is $(CH_2)_2$—$R_{19}$, and $R_{19}$ is $N(CH_3)_3$.

In some embodiments, when $R_1$ is NH, then $R_2$ is one of: branched or unbranched C2-C10 substituted or unsubstituted alkyl, amine, amide, acetyl, aldehyde, alkoxy (ether), ester, carbonyl, carboxyl, carbamate, diol, triol, trisubstituted ammonium, optionally substituted at 1-5 positions and each substituent is one of branched or unbranched C1-C5 substituted or unsubstituted alkyl, amine, amide, acetyl, aldehyde, alkoxy (ether), hydroxy, ester, carbonyl, carboxyl, carbamate, diol, triol, trisubstituted ammonium.

In some embodiments, when $R_1$ is NH, then $R_2$ is one of: carboxylic acid or dicarboxylic acid, preferably pentanoic acid, butanedioic acid, or pentanedioic acid, still more preferably, 2-(6-amino)-pentanoic acid, 2-butanedioic acid or 2-butanedioic acid, or 2-pentanedioic acid or 2-pentanedioic acid, and amide, preferably substituted amide, more preferably substituted ethanamide, still more preferably substituted 2-ethanamide, still more preferably 2-(3-aminopropane)-N-2-butanedioic-2-ethanamide, 2-(3-aminopropane)-N-2-butanedioic-2-ethanamide, 2-(3-aminopropane)-N-2-pentanedioic-2-ethanamide, 2-(3-aminopropane)-N-2-pentanedioic-2-ethanamide, 2-(2-carboxyethyl)-N-(2-(3-aminopropane)-carboxymethyl)-2-ethanamide, 2-carboxymethyl-N-(2-(3-aminopropane)-carboxymethyl)-2-ethanamide, or 2-(hydroxymethyl)-N-2-pentanedioic-2-ethanamide.

In some embodiments, when $R_1$ is NH, then $R_2$ is one of: 2-butanedioic acid, 2-pentanedioic acid, or 2-(5-amino)-pentanoic acid, and 2-(3-aminopropane)-N-2-butanedioic-2-ethanamide, 2-(3-aminopropane)-N-2-butanedioic-2-ethanamide, 2-(3-aminopropane)-N-2-pentanedioic-2-ethanamide, 2-(3-aminopropane)-N-2-pentanedioic-2-ethanamide, 2-(2-carboxyethyl)-N-(2-(3-aminopropane)-carboxymethyl)-2-ethanamide, 2-carboxymethyl-N-(2-(3-aminopropane)-carboxymethyl)-2-ethanamide, or 2-(hydroxymethyl)-N-2-pentanedioic-2-ethanamide.

In some embodiments, when $R_1$ is NH, then $R_2$ is $(CR_{13}R_{14})_Z$—$R_{15}$, wherein each $R_{13}$ is H;

each $R_{14}$ is, independently, one of H, $CH_3$, carboxyl (COOH), ethanol ($CH_2OH$), preferably 2-ethanol, amine or alkylamine, preferably propylamine, carboxylic acid, preferably ethanoic acid or propanoic acid, Z is and integer from 1-3, and $R_{15}$ is one of carboxyl (—COOH), amino (—$NH_2$), or amide, preferably 1-amide, more preferably N-substituted-1-amide (or N-substituted carboxamide) (—CONH—$R_{16}$, where $R_{16}$ is substituted alkyl, preferably 1,3-dicarboxypropane, 1-(1-carboxy)butyric acid or butanedioic acid, 1-carboxy-2-pentanoic acid or pentanedioic acid, preferably 2-pentanedioic acid, or 2-(3-aminopropyl)ethanoic acid.

In some embodiments, when $R_1$ is NH, then $R_2$ is one of Formulas Iq-Ix:

Formula Iq

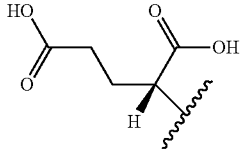

Formula Ir

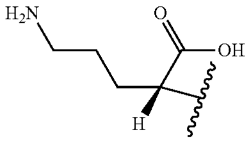

Formula Is

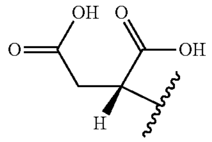

Formula It

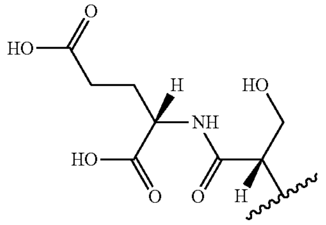

Formula Iu

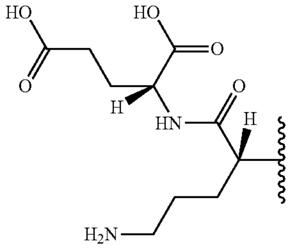

Formula Iv

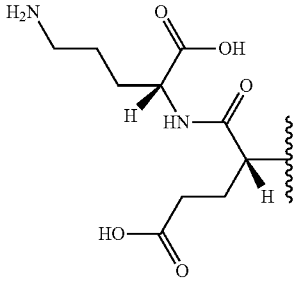

Formula Iw

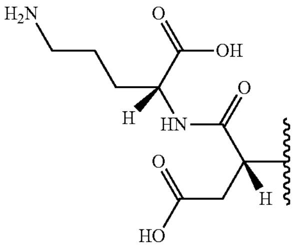

-continued

Formula Ix

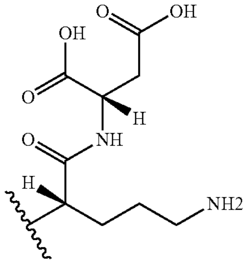

In some embodiments, the compound according to Formula I can be one of Compounds 1-24 of Table 1.

Furthermore, all compounds of the present disclosure which exist in free base or acid form can be converted to their pharmaceutically acceptable salts by treatment with the appropriate inorganic or organic base or acid by methods known to one skilled in the art. Salts of the compounds of the present disclosure can be converted to their free base or acid form by standard techniques.

Compositions, Medicaments, and Co-Administrators

Administration of the platinum-based chemotherapeutic agents of the present disclosure can be in accordance with known methods, protocols, doses, dosage regimes, concentrations, administration timeframes and time tables, and so forth, (e.g., depending on the type, stage, and/or grade of cancer, patient age, weight, health, etc.). Illustratively, the cisplatin or other platinum-based chemotherapeutic can be administered via IV infusion, as known in the art. For example, 20 mg/m2 of cisplatin or other platinum-based chemotherapeutic can be administered by slow IV infusion daily for 5 days per cycle (alone or in combination with other approved chemotherapeutic agents). Alternatively, 75 to 100 mg/m2 of cisplatin or other platinum-based chemotherapeutic can be administered by slow IV infusion once every 3 to 4 weeks on Day 1. Alternatively, 50 to 70 mg/m2 of cisplatin or other platinum-based chemotherapeutic can be administered by slow IV infusion once every 3 to 4 weeks; for heavily pretreated patients, an initial dose of 50 mg/m2 by slow IV infusion once every 4 weeks may be recommended. Thus, the platinum-based chemotherapeutic drug can be administered in an amount and/or manner sufficient to treat the cancer (e.g., to reduce the number of cancer cells).

Administration of the novel compounds of the present disclosure, or their pharmaceutically acceptable salts, in pure form or in an appropriate pharmaceutical composition or medicament, can be carried out via any of the accepted modes of administration of agents for serving similar utilities. The pharmaceutical compositions or medicaments of embodiments of the present disclosure can be prepared by combining a compound of the present disclosure with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions or medicaments include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions or medicaments of the present disclosure are formulated so as to allow the active ingredients contained therein to be bioavailable upon administration of the composition or medicament to a patient. Compositions or medicaments that will be administered to a subject or patient take the form of one or more dosage units, where for example, a tablet may be a single dosage unit, and a container of a compound of the present disclosure in aerosol form may hold a plurality of dosage units. Actual methods of preparing such dosage forms are known, or will be apparent, to those skilled in this art; for example, see e.g., Remington: The Science and Practice of Pharmacy, 20th Edition (Philadelphia College of Pharmacy and Science, 2000). The composition or medicament to be administered will, in any event, contain a therapeutically effective amount of a compound of the present disclosure, or a pharmaceutically acceptable salt thereof, for treatment of a disease or condition of interest in accordance with the teachings of this disclosure.

A pharmaceutical composition or medicament of some embodiments of the present disclosure may be in the form of a solid or liquid. In one aspect, the carrier(s) are particulate, so that the compositions or medicaments are, for example, in tablet or powder form. The carrier(s) may be liquid, with the compositions being, for example, an oral syrup, injectable liquid or an aerosol, which is useful in, for example, inhalation or inhalatory administration.

When intended for oral administration, the pharmaceutical composition or medicament is preferably in either solid or liquid form, where semi-solid, semi-liquid, suspension and gel forms are included within the forms considered herein as solid or liquid.

As a solid composition or medicament for oral administration, the pharmaceutical composition or medicament may be formulated into a powder, granule, compressed tablet, pill, capsule, chewing gum, wafer or the like form. Such a solid composition or medicament will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition or medicament is in the form of a capsule, for example, a gelatin capsule, it may contain, in addition to materials of the above type, a liquid carrier such as polyethylene glycol or oil.

The pharmaceutical composition or medicament may be in the form of a liquid, for example, an elixir, syrup, solution, emulsion or suspension. The liquid may be for oral administration or for delivery by injection, as two examples. When intended for oral administration, preferred composition or medicament contain, in addition to the present compounds, one or more of a sweetening agent, preservatives, dye/colorant and flavor enhancer. In a composition or medicament intended to be administered by injection, one or more of a surfactant, preservative, wetting agent, dispersing agent, suspending agent, buffer, stabilizer and isotonic agent may be included.

The liquid pharmaceutical compositions and medicaments of some embodiments of the present disclosure, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition or medicament is preferably sterile.

A liquid pharmaceutical composition or medicament of certain embodiments of the present disclosure intended for either parenteral or oral administration should contain an amount of a compound of the present disclosure such that a suitable dosage will be obtained.

In some embodiments, the pharmaceutical composition or medicament of the present disclosure may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition or medicament for topical administration. If intended for transdermal administration, the composition or medicament may include a transdermal patch or iontophoresis device.

The pharmaceutical composition or medicament of various embodiments of the present disclosure may be intended for rectal administration, in the form, for example, of a suppository, which will melt in the rectum and release the drug. The composition or medicament for rectal administration may contain an oleaginous base as a suitable nonirritating excipient. Such bases include, without limitation, lanolin, cocoa butter and polyethylene glycol.

Embodiments of the pharmaceutical composition or medicament of the present disclosure may include various materials, which modify the physical form of a solid or liquid dosage unit. For example, the composition or medicament may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition or medicament of some embodiments of the present disclosure in solid or liquid form may include an agent that binds to the compound of the present disclosure and thereby assists in the delivery of the compound. Suitable agents that may act in this capacity include a monoclonal or polyclonal antibody, a protein or a liposome.

The pharmaceutical composition or medicament of other embodiments of the present disclosure may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the present disclosure may be delivered in single phase, bi-phasic, or triphasic systems in order to deliver the active ingredient(s). Delivery of the aerosol includes the necessary container, activators, valves, subcontainers, and the like, which together may form a kit. One skilled in the art, without undue experimentation may determine preferred aerosols.

In some embodiments, the pharmaceutical compositions or medicaments of the present disclosure may be prepared by methodology well known in the pharmaceutical art. For example, a pharmaceutical composition or medicament intended to be administered by injection can be prepared by combining a compound of the present disclosure with sterile, distilled water so as to form a solution. A surfactant may be added to facilitate the formation of a homogeneous solution or suspension. Surfactants are compounds that non-covalently interact with the compound of the present disclosure so as to facilitate dissolution or homogeneous suspension of the compound in the aqueous delivery system.

The compounds of the present disclosure, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

In some embodiments, the compound of Formula I is provided in the pharmaceutical compositions or medicaments of the present disclosure in an amount sufficient to provide a dose of about 100 mg/kg (mg of compound per kg of subject body mass/weight), 90 mg/kg, 80 mg/kg, 75 mg/kg, 70 mg/kg, 60 mg/kg, 50 mg/kg, 40 mg/kg, 30 mg/kg, 25 mg/kg, 20 mg/kg, 15 mg/kg, 10 mg/kg, 5 mg/kg, 2.5 mg/kg, or 1 mg/kg, or between about 1-100 mg/kg, 2.5-90 mg/kg, 5-80 mg/kg, 10-75 mg/kg, 15-70 mg/kg, 20-60 mg/kg, 25-50 mg/kg, or any range therebetween.

In some embodiments, the concentration of the compound of Formula I provided in the pharmaceutical compositions or medicaments of the present disclosure is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001%, w/w, w/v or v/v, of the pharmaceutical composition or medicament.

In some embodiments, the concentration of the compound of Formula I provided in the pharmaceutical compositions or medicaments of the present disclosure is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001%, w/w, w/v, or v/v, of the pharmaceutical composition or medicament.

In some embodiments, the concentration of the compound of the Formula I provided in the pharmaceutical compositions or medicaments of the present disclosure is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v, of the pharmaceutical composition or medicament.

In some embodiments, the concentration of the compound of Formula I provided in the pharmaceutical compositions or medicaments of the present disclosure is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v, of the pharmaceutical composition or medicament.

In some embodiments, the amount the compound of Formula I provided in the pharmaceutical compositions or medicaments of the present disclosure is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g of the pharmaceutical composition or medicament.

In some embodiments, the amount of the compound of Formula I provided in the pharmaceutical compositions or medicaments of the present disclosure is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g of the pharmaceutical composition or medicament.

In some embodiments, the amount of the compound of Formula I provided in the pharmaceutical compositions or medicaments of the present disclosure is in the range of 0.0001-10 g, 0.0005-9 g, 0.001-8 g, 0.005-7 g, 0.01-6 g, 0.05-5 g, 0.1-4 g, 0.5-4 g, or 1-3 g of the pharmaceutical composition or medicament.

Compounds of the present disclosure, or pharmaceutically acceptable derivatives thereof, may also be administered simultaneously with, prior to, or after administration of one or more other therapeutic agents (e.g., platinum-based chemotherapeutics). Such combination therapy may include administration of a single pharmaceutical dosage formulation (or co-formulation) which contains a compound of the present disclosure and the one or more platinum-based chemotherapeutics. Combination therapy (or co-administration) may also or alternatively include separate administrations of the compound of the present disclosure and the one or more platinum-based chemotherapeutics (each in its own separate pharmaceutical dosage formulation). For example, a compound of the present disclosure and the platinum-based chemotherapeutic(s) can be administered to the patient at the same time (e.g., in the same or separate injections, infusions, or other administration form, such as oral dosage composition such as a tablet or capsule, or each agent administered in separate oral dosage formulations. Where separate dosage formulations are used, the compounds of the present disclosure and one or more additional active agents can be administered at essentially the same time, i.e., concurrently, or at separately staggered times, i.e., sequentially; combination therapy is understood to include all these regimens.

In some embodiments, the novel compound(s) of the present disclosure can be co-administered, as defined herein, with each dose of the platinum-based chemotherapeutic drug. In some embodiments, co-administration of the novel compound(s) of the present disclosure with the platinum-based chemotherapeutic drug can include daily or twice daily doses of the novel compound(s) of the present disclosure, for a prescribed period of time, following a dose (or each dose) of the platinum-based chemotherapeutic drug. For instance, the platinum-based chemotherapeutic drug may be administered once (daily) each 3 to 4 weeks, and the novel compound(s) of the present disclosure can be co-administered (e.g., once daily or twice daily) within 48 hours of the chemotherapy and (once daily or twice daily) thereafter for 1, 2, 3, 4, 5, 6, 7, 8, 9, 10, 11, 12, 13, 14, or more (subsequent and/or consecutive) days.

Chemical Synthesis

All chemicals, reagents and solvents were obtained from commercial vendors, such as Enamine, Sigma-Aldrich, and Fisher Scientific. Indicated reaction temperatures refer to those of the reaction bath, while room temperature (rt) is noted as 25° C. Analytical thin layer chromatography (TLC) was performed with glass backed silica plates (20×20 cm, pH=5, MF254). Visualization was accomplished using a 254 nm UV lamp. $^1$H spectra were recorded on a 400 MHz spectrometer using solutions of samples in DMSO-d6 or other commercially-available deuterated solvents, as noted. Chemical shifts are reported in ppm with tetramethylsilane as standard. Data are reported as follows: chemical shift, number of protons, multiplicity (s=singlet, d=doublet, dd=doublet of doublet, t=triplet, q=quartet, b=broad, m=multiplet). All novel compounds were characterized by $^1$H-NMR and mass spectroscopy (MS).

Example 1. 1-ethyl piperidin-4-yl 4-(phenylsulfanyl)butanoate

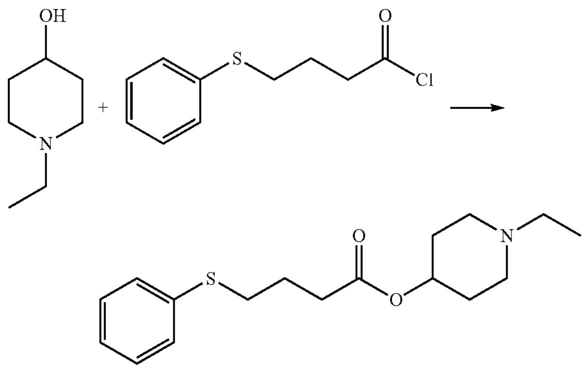

Compound 1

A solution of 1-ethyl-4-piperidinol (0.993 g, 7.68 mmol) and triethylamine (1.46 mL, 10.48 mmol) in dichloromethane (30 mL) was prepared in a round bottom flask under an inert atmosphere. The mixture was cooled to 0° C. and phenylthiobutanoyl chloride (1.500 g, 6.99 mmol) in dichloromethane (20 mL) was added dropwise. After stirring overnight at r.t., the mixture was worked up by addition of distilled water (20 mL). The organic layer was separated and the aqueous layer was extracted with dichloromethane (3×20 mL). The combined organic layers were dried (Na2SO4) and concentrated under reduced pressure. Purification of the crude product by HPLC afforded Compound 1 as a TFA salt (0.268 g, 9.1%). $^1$H NMR (400 MHz, d6-DMSO) δ 1.20 (t, 3H), 1.71 (m, 1H), 1.83 (m, 2H), 1.94 (m, 2H), 2.10 (m, 1H), 2.45 (m, 2H), 2.99 (q, 3H), 3.10 (m, 31H), 3.44 (dd, 2H), 4.88 (m, 1H), 7.19 (m, 1H), 7.33 (m, 4H), 9.57 (br s, 1H). m/z 308 [M+H]+.

Example 2. 1,4-dimethylpiperidin-4-yl 4-(phenylsulfanyl)butanoate

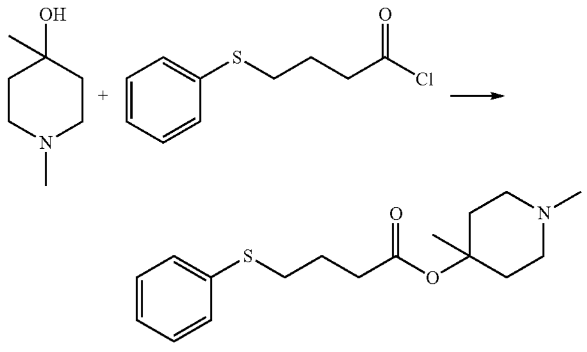

Compound 2

A solution of 1,4-dimethyl-4-piperidinol (0.993 g, 7.68 mmol), triethylamine (1.46 mL, 10.48 mmol) in dichloromethane (30 mL) was prepared in a round bottom flask under an inert atmosphere. The mixture was cooled to 0° C. and phenylthiobutanoyl chloride (1.500 g, 6.99 mmol) in dichloromethane (20 mL) was added dropwise. After stirring for overnight at r.t., the mixture was worked up by addition of distilled water (20 mL). The organic layer was separated and the aqueous layer was extracted with dichloromethane (3×20 mL). The combined organic layers were dried ($Na_2SO_4$) and concentrated under reduced pressure. Purification of the crude product by HPLC afforded Compound 2 as a TFA salt (0.612 g, 20.8%). $^1$H NMR (400 MHz, d6-DMSO) δ 1.38 (m, 3H), 1.69 (m, 2H), 1.78 (m, 2H), 2.31 (m, 2H), 2.39 (m, 2H), 2.65 (m, 3H), 2.87 (m, 4H), 3.21 (m, 2H), 7.15 (m, 11H), 7.26 (m, 4H). m/z 308 [M+H]+.

Example 3: 2-(dimcthylamino)ethyl 4-(phenylsulfanyl)butanoate

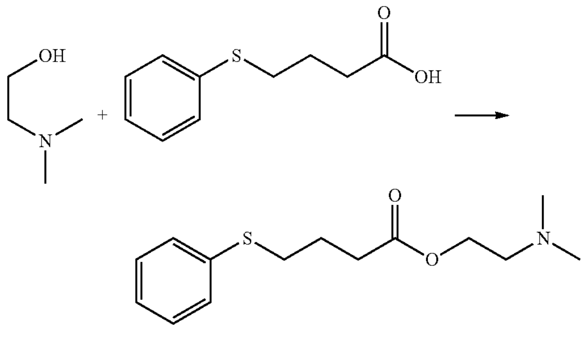

Phenylthiobutanoic acid (30 g, 152.8 mmol) and N,N-dimethylethanolamine (15 g, 168 mmol) were dissolved in $CH_2Cl_2$ (300 mL). The stirred solution was cooled with an ice-bath and 4-dimethylaminopyridine (1.86 g, 15.28 mmol) and N,N'-dicyclohexylcarbodiimide (31.52 g, 152.8 mmol) were sequentially added. The temperature was slowly raised to r.t. and the reaction mixture was stirred overnight. After the consumption of the starting material, water (300 mL) was added to the solution. The organic layer was separated, washed with water (2×200 mL), dried over $Na_2SO_4$, and evaporated under reduced pressure. Final product Compound 3 was purified by flash-chromatography (hexane: ethyl acetate:triethylamine) (10.1 g, 24.7%). $^1$H NMR (400 MHz, d6-DMSO) δ 7.34-7.28 (m, 4H), 7.21-7.15 (m, 1H), 4.08 (t, 2H), 3.02-2.95 (m, 2H), 2.47-2.42 (m, 4H), 2.13 (s, 6H), 1.80 (m, 2H). m/z 268 [M+H]+.

Example 4: N,N,N-trimethyl-2-{[4-(phenylsulfanyl)butanoyl]oxy}ethan-1-aminium chloride

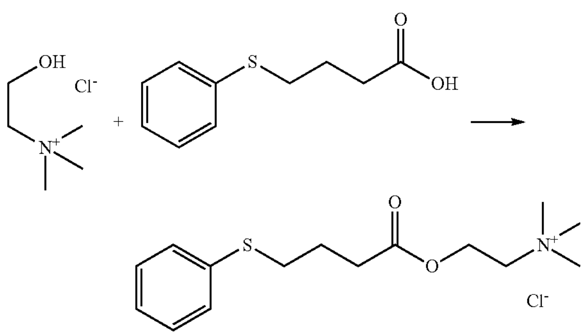

Phenylthiobutanoic acid (24 g, 122.28 mmol, 1 eq.) and choline chloride (18.78 g, 134.5 mmol, 1.1 eq.) were dissolved in $CH_2Cl_2$ (240 mL). The solution was cooled with ice-bath, and with stirring, 4-dimethylaminopyridine (1.494 g, 12.22 mmol, 0.1 eq.) and N,N'-dicyclohexylcarbodiimide (25.23 g, 122.28 mmol, 1 eq.) were sequentially added. The temperature was slowly raised to r.t. and the solution was stirred overnight. After the consumption of the starting material, water (250 mL) was added to the solution. The water layer was separated and washed with $CH_2Cl_2$ (200 mL) and water was evaporated. Final product Compound 22 was purified by flash-chromatography (acetonitrile:water) to obtain 10.3 g (29.8%). Chloride content: 0.048 g of final compound was dissolved in 30 ml of solution (2-propanol: water 1:2) and was titrated with 0.10058 n AgNO3. Equivalence point (1.55 ml) was fixed by the Eosin indicator. $^1$H NMR (400 MHz, d6-DMSO) δ 7.35-7.27 (m, 4H), 7.21-7.15 (m, 1H), 4.43 (m, 2H), 3.69-3.65 (m, 2H), 3.11 (s, 9H), 3.04-2.96 (m, 2H), 2.53-2.48 (m, 2H), 1.82-1.77 (m, 2H). m/z 282 [M+].

Example 5: Additional Illustrative Compounds

A listing of illustrative Compounds 1-24 are presented in FIG. 1. Compounds 4-21 and 23-24 were prepared and purified via similar methods to Compounds 1, 2, 3 and 22 above, with the appropriate alcohol or amine, or protected version, coupled to PTBA or the corresponding acid chloride and then deprotected, if needed. Compounds were characterized by $^1$H NMR, HPLC and MS.

Example 6: Determination of Kinetic Solubility

A 20 mM stock solution of the test compound in 100% DMSO dilutions were prepared to a theoretical concentration of 400 μM in duplicates in phosphate-buffered saline pH 7.4 (138 mM NaCl, 2.7 mM KCl, 10 mM K-phosphate) with 2% final DMSO. The experimental compound dilutions in PBS were further allowed to equilibrate at 25° C. on a thermostatic shaker for two hours and then filtered through HTS filter plates using a vacuum manifold. The filtrates of test compounds were diluted 2-fold with acetonitrile with 2% DMSO before measuring.

In parallel, compound dilutions in 50% acetonitrile/PBS were prepared to theoretical concentrations of 0 M (blank), 10 μM, 25 μM, 50 μM, 100 μM, and 200 μM with 2% final DMSO to generate calibration curves. Ondansetron was used as reference compound to control proper assay performance. 200 μl of each sample was transferred to 96-well plate and measured in 200-550 nm range with 5 nm step.

The concentrations of compounds in PBS filtrate were calculated using a dedicated Microsoft Excel calculation script. Proper absorbance wavelengths for calculations were selected for each compound manually based on absorbance maximums (absolute absorbance unit values for the minimum and maximum concentration points within 0-3 OD range). Each of the final datasets was additionally visually evaluated by the operator and goodness of fit ($R_2$) was calculated for each calibration curve. The effective range of this assay was approximately 2-400 μM and the compounds returning values close to the upper limit of the range may have higher actual solubility.

TABLE 2

Table 2. Kinetic Solubility of Example compounds 1-24

| Compound | Kinetic Solubility PBS pH = 7.4 (μM) |
|---|---|
| 1 | >400 |
| 2 | >400 |
| 3 | 381 |
| 4 | 387 |
| 5 | 396 |
| 6 | >400 |
| 7 | 385 |
| 8 | 383 |
| 9 | 383 |
| 10 | 379 |
| 11 | 391 |
| 12 | >400 |
| 13 | >400 |
| 14 | 387 |
| 15 | ≥400 |
| 16 | >400 |
| 17 | >400 |
| 18 | 362 |
| 19 | >400 |
| 20 | >400 |
| 21 | >400 |
| 22 | 398 |
| 23 | 399 |
| 24 | 390 |

Compounds (pro-drugs) of the present disclosure are designed to release the active carboxylic acid, PTBA, in vivo. Compounds of the present disclosure have been tested in vitro for plasma stability and in vivo to demonstrate loss of pro-drug over time and the appearance of PTBA.

Example 7: Plasma Stability Studies

Plasma stability studies were carried out in plasma from various species. For example, the stability of Compound 22 was evaluated in rat, dog, and human plasma at five time points over 120 minutes using HPLC-MS/MS.

All measurements were performed using Shimadzu HPLC system including vacuum degasser, gradient pumps, reverse phase column, column oven and autosampler. The HPLC system was coupled with tandem mass spectrometer API 3000 (PE Sciex). Both the positive and negative ion modes of the TurboIonSpray ion source were used. Acquisition and analysis of the data were performed using Analyst 1.5.2 software (PE Sciex). Incubations were carried out in 5 aliquots of 70 μL each (one for each time point), in duplicates. Test compounds (1 μM, final DMSO concentration 1%) were incubated at 37° C. with shaking at 100 rpm. Five time points over 120 minutes have been analyzed. The reactions were stopped by adding 420 μL of acetonitrile-water mixture (90:10) with subsequent plasma proteins sedimentation by centrifuging at 5500 rpm for 5 minutes. Supernatants were analyzed by the HPLC system coupled with tandem mass spectrometer. The percentage of the test compounds remaining after incubation in plasma and their half-lives ($T_{1/2}$) were calculated.

Figure 2:
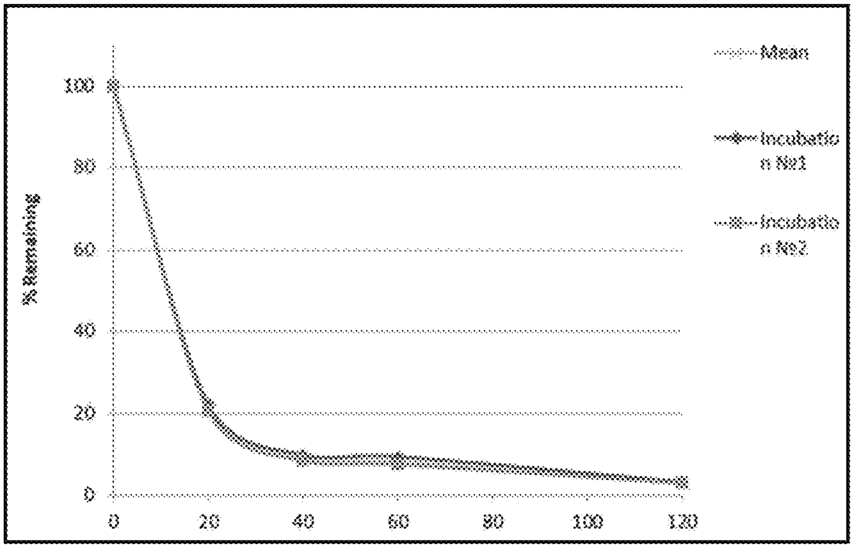
FIG. 2 illustrates stability of illustrative Compound 22 in Rat plasma.
Figure 3:
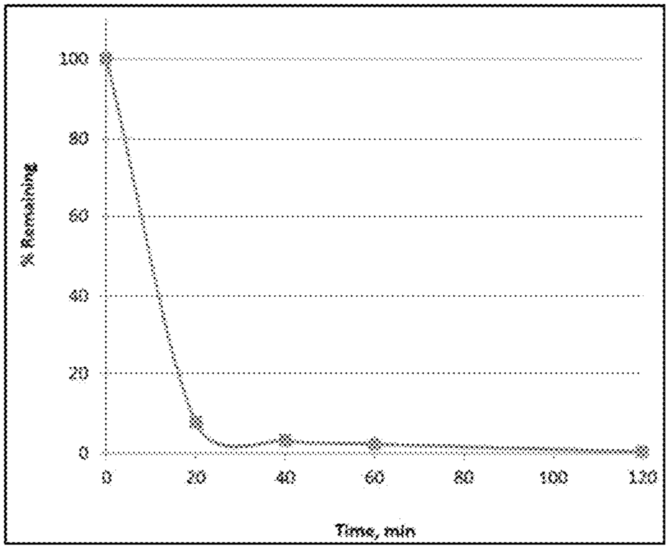
FIG. 3 illustrates stability of illustrative Compound 22 in Dog plasma.
Figure 4:
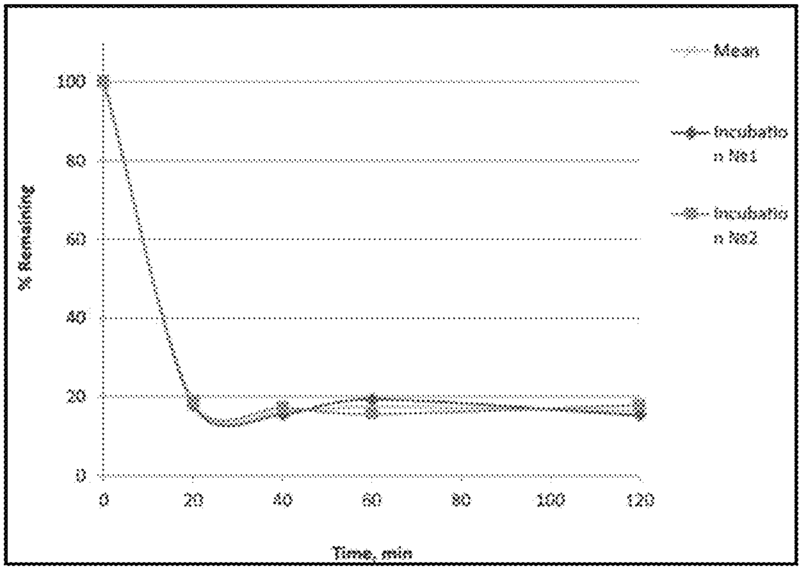
FIG. 4 illustrates stability of illustrative Compound 22 in Human plasma.

FIGS. 2-4 illustrate the plasma stability of illustrative Compound 22 over time in Rat, Dog, and Human, respectively.

Figure 5:
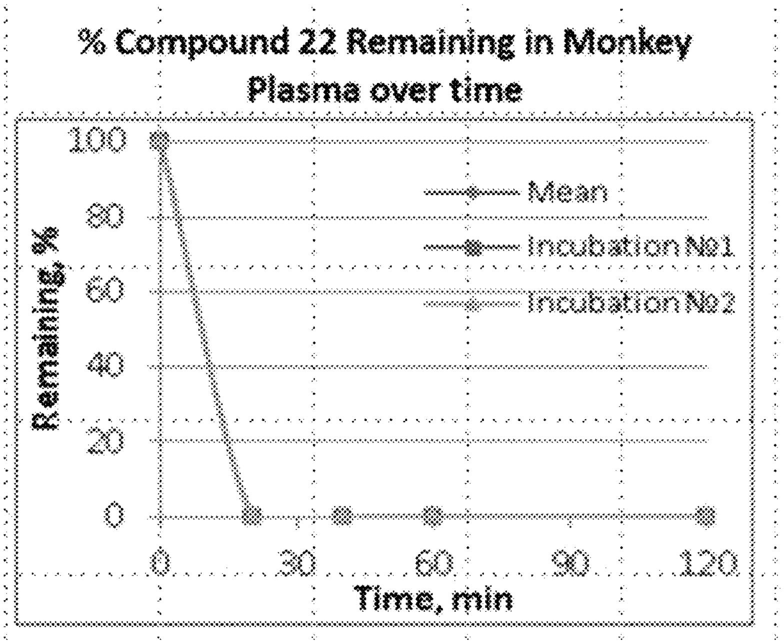
FIG. 5 illustrates the percentage of illustrative Compound 22 remaining in Monkey plasma over time.
Figure 6:
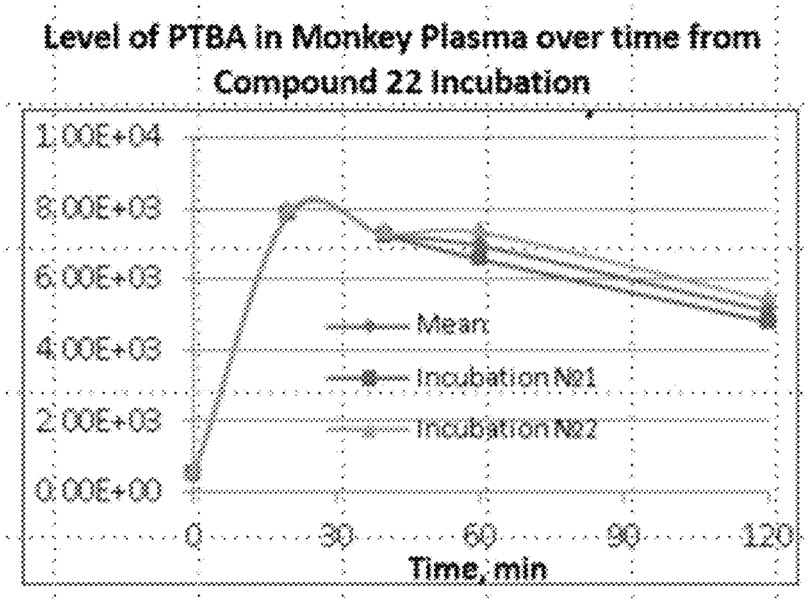
FIG. 6 illustrates PTBA levels in Monkey plasma over time following administration of Compound 22.

Further experiments measured the disappearance of pro-drug from plasma sample while evaluating the appearance of the active agent, PTBA (see FIGS. 5-6). Pro-drug was incubated in monkey plasma and the level of pro-drug was measured along with a semi-quantitative determination of one metabolite, PTBA, using HPLC-MS/MS. All measurements were performed using Shimadzu Prominence HPLC system including vacuum degasser, gradient pumps, reverse phase column, column oven and autosampler. The HPLC system was coupled with tandem mass spectrometer API 3000 (PE Sciex). Both the positive and negative ion modes of the TurbolonSpray ion source were used. Acquisition and analysis of the data were performed using Analyst 1.5.2 software (PE Sciex). Incubations were carried out in multiple aliquots of 70 μL each (one for each time point), in duplicates. Test compounds (1 M, final DMSO concentration 1%) were incubated at 37° C. with shaking at 100 rpm. 3-5 time points over 120 minutes were analyzed. The reactions were stopped by adding 420 μL of acetonitrile-water mixture (90:10; stop-solution) with subsequent plasma proteins sedimentation by centrifuging at 5500 rpm for 5 minutes. Supernatants were analyzed by the HPLC system coupled with tandem mass spectrometer. A "true zero timepoint" was established by adding the compound to a mixture of plasma with the stop-solution (no direct contact of the compound with plasma prior to stop solution), due to the rapid degradation of some pro-drugs in plasma. For example, Compound 22 was incubated in monkey plasma, and disappearance of Compound 22 and appearance of PTBA was evaluated.

FIG. 5 illustrates the percentage of illustrative Compound 22 remaining in Monkey plasma over time. FIG. 6 illustrates PTBA levels in Monkey plasma over time following administration of Compound 22.

Example 8: Rat Pharmacokinetic Studies

Compounds of the present disclosure were evaluated in rat PK studies to determine release of PTBA in vivo after i.v. injection (see FIG. 7).

Typically, the vehicle was Captisol-Saline-Water for injections (20%:40%:40%, v/v/v). To prepare the formulation, the compound was dissolved in the necessary volume of 20% Captisol solution (Captisol was previously dissolved in a mixture of Saline-Water for injections, 1:1, v/v), vortexed for 1 min and sonicated for 1 min at 40° C. The resulting solution was clear. The batch of working formulation was prepared 30 min prior to the in vivo study. Study design, animal selection, handling and treatment were all in accordance with the CRO's PK study protocols and Institutional Animal Care and Use Guidelines. Animal treatment and plasma samples preparation were conducted by the Animal Laboratory personnel at the CRO. Male Wistar rats were used in studies. All animals were fasted for 16 h before dosing. Typically, seven time points (pre-dose (0), 5, 15, 30, 60, 120, and 480 min) and intravenous (IV) route of administration were set for this pharmacokinetic study. The compound-treated group included 3 animals. Solution of Lidocaine (7 mg/kg) was administered subcutaneously five minutes prior to catheter placement in the left lateral tail vein. The catheter was flushed with 500-IU/ml heparin. The test compound formulation was injected into the right lateral vein. Blood collection was performed from the tail vein in tubes containing K3EDTA. Plasma samples were immediately prepared, flash-frozen and stored at −70° C. until subsequent analysis. Analyses of plasma samples were conducted by the Bioanalytical Laboratory personnel at the CRO. The concentrations of pro-drug test compounds and PTBA were determined using high performance liquid chromatography/tandem mass spectrometry (HPLC-MS/MS), a Shimadzu HPLC system consisted of 2 isocratic pumps LC-10ADvp, an autosampler SIL-20AC, a sub-controller FCV-14AH, and a degasser DGU-14A. Mass spectrometric analysis was performed using API 3000 (triple-quadrupole) instrument from AB Sciex (Canada) with an electro-spray (ESI) interface. The data acquisition and system control was performed using Analyst 1.5.2 software (AB Sciex, Canada).

Chromatographic Conditions for Pro-Drug Test Compounds:

- Column: Discovery HS C18 (50×2.1 mm, 5 μm)
- Mobile phase A: Acetonitrile:Water:Formic acid=50:950:1
- Mobile phase B: Acetonitrile:Formic acid=100:0.1
- Linear gradient: 0 min 12% B, 1.00 min 90% B, 1.15 min 90% B, 1.16 min 12% B, 2.7 min stop
- Elution rate: 400 L/min. A divert valve directed the flow to the detector from 1.3 to 1.8 min
- Column temperature: 30° C.
- MS/MS Detection:
- Scan type: Positive MRM, Ion source: Turbo spray, Ionization mode: ESI
- Nebulize gas: 15 L/min, Curtain gas: 8 L/min, Collision gas: 4 L/min
- Ionspray voltage: 5000 V, Temperature: 400° C.

Chromatographic Conditions for PTBA:

- Column: Hypersil BDS C8 (50×2.1 mm, 3 m)
- Mobile phase A: Acetonitrile:Water:Formic acid=50:950:1
- Mobile phase B: Acetonitrile:Formic acid=100:0.1
- Linear gradient: 0 min 17% B, 1.40 min 100% B, 1.41 min 17% B, 2.6 min stop
- Elution rate: 400 μL/min. A divert valve directed the flow to the detector from 1.45 to 1.95 min
- Column temperature: 30° C.

Figure 7A:
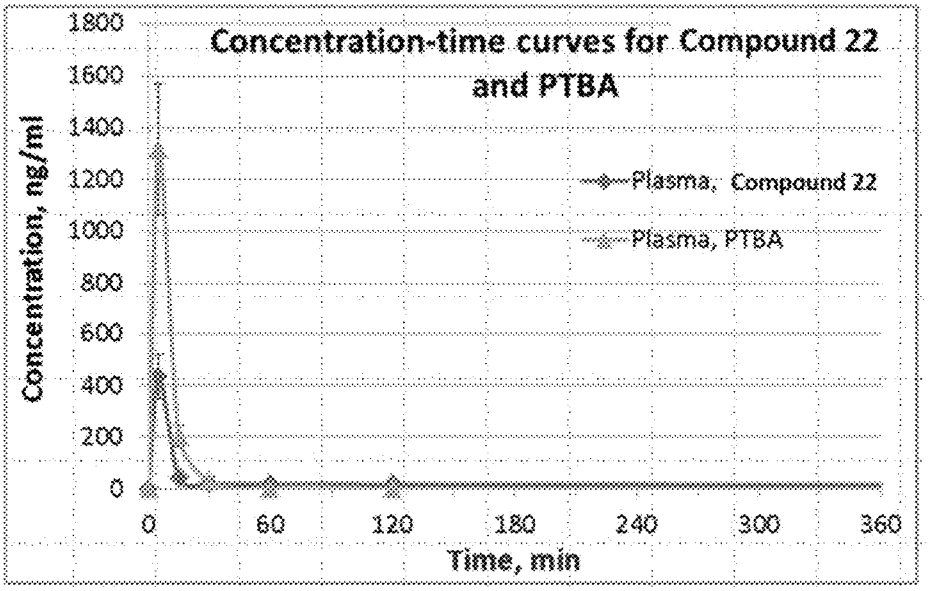
FIG. 7A illustrates plasma concentration of pro-drug (Compound 22) and PTBA over time in rats following i.v. administration of pro-drug (Compound 22).
Figure 7B:
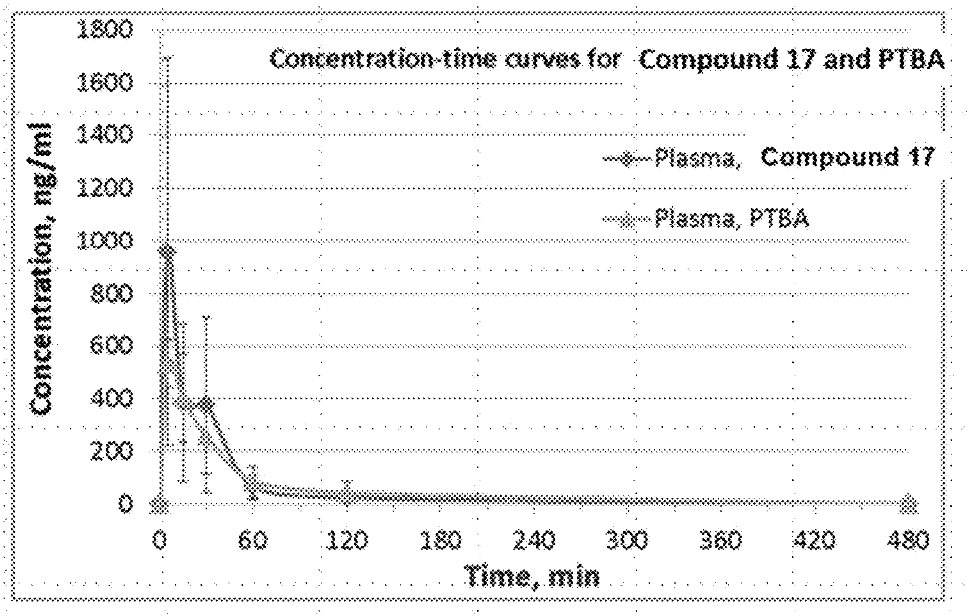
FIG. 7B illustrates plasma concentration of pro-drug (Compound 17) and PTBA over time in Rats.
Figure 7C:
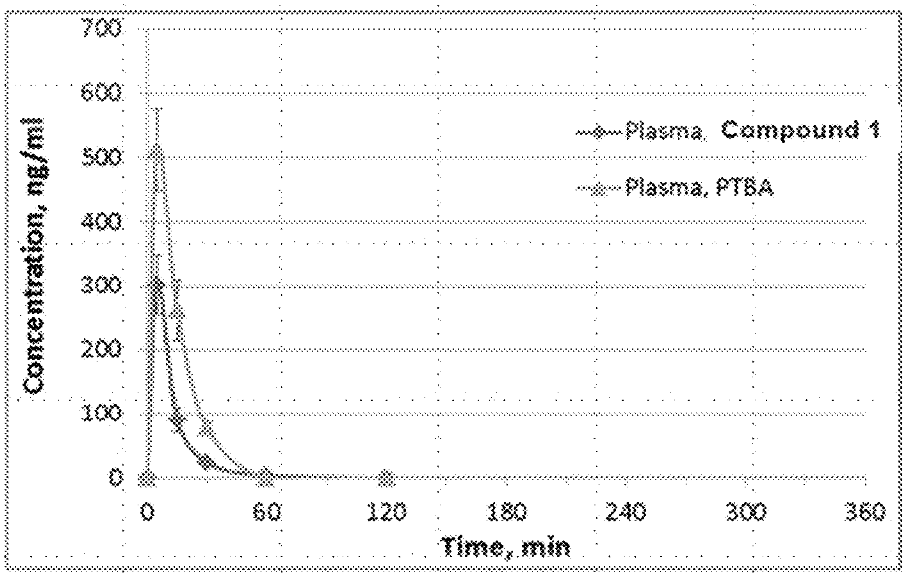
FIG. 7C illustrates plasma concentration of pro-drug (Compound 1) and PTBA over time in Rats.
Figure 7D:
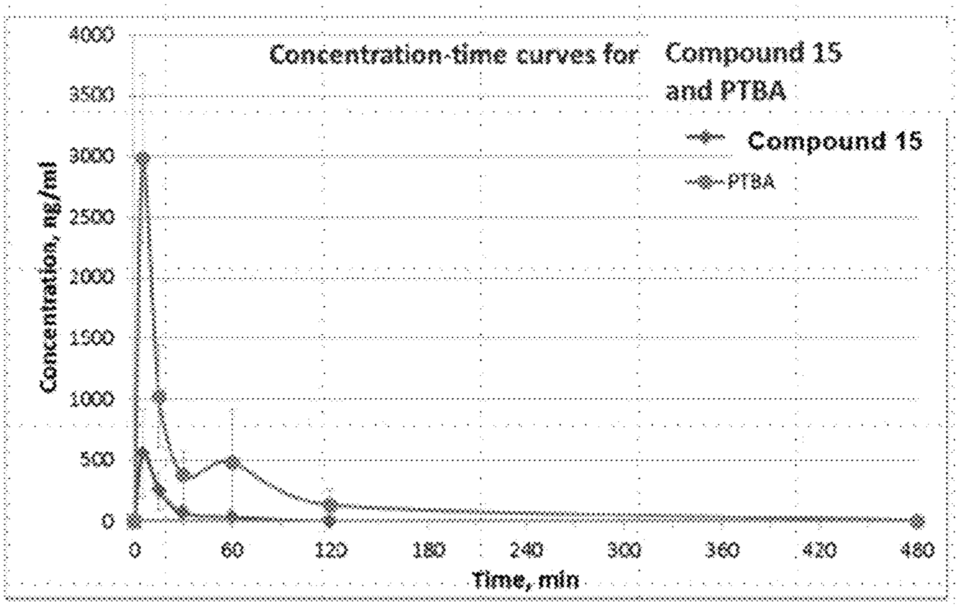
FIG. 7D illustrates plasma concentration of pro-drug (Compound 15) and PTBA over time in Rats.

MS/MS Detection:

- Scan type: Negative MRM, Ion source: Turbo spray, Ionization mode: ESI
- Nebulize gas: 15 L/min, Curtain gas: 8 L/min, Collision gas: 4 L/min
- Ionspray voltage: −4200 V, Temperature: 400° C.
- Illustrative Compound 22 was dosed at 2 mg/kg i.v to 3 rats. FIG. 7A shows the concentration time profile of the pro-drug (Compound 22) and PTBA.
- Illustrative Compound 17 was dosed at 2 mg/kg i.v to 3 rats. FIG. 7B shows the concentration time profile of the pro-drug (Compound 17) and PTBA.
- Illustrative Compound 1 was dosed at 2 mg/kg i.v to 3 rats. FIG. 7C shows the concentration time profile of the pro-drug (Compound 1) and PTBA.
- Illustrative Compound 15 was dosed at 6 mg/kg i.v to 5 rats. FIG. 7D shows the concentration time profile of the pro-drug (Compound 15) and PTBA.

Example 9: In Vivo Efficacy in a Murine AKI Model

The aim of the study was to investigate the efficacy of test compound(s) in a (mouse) model for acute kidney injury. Specifically, the study investigated the efficacy of test compound(s) in cisplatin-induced acute kidney injury (CI-AKI) mouse model. For example, the effect of daily repeated intraperitoneal (IP) administration of Compound 22 at doses of 50 mg/kg for 7 consecutive days in four different treatment regimens on development of pathology in mice in CI-AKI model was evaluated. Serum analysis for urea (BUN) was performed on the 5th day and 12th days after cisplatin administration. The mean body weight loss per group was calculated every day of the study as percentage loss of initial (day 0) weight for each individual animal.

Study design, animal selection, handling and treatment were all in accordance with the CRO's study protocols and Institutional Animal Care and Use Guidelines. Animal treatment and serum samples preparation were conducted by the Animal Laboratory personnel at the CRO. 100 female C57BL/6J mice 11-14 weeks old were randomized by body weight and divided into five groups, 20 animals each. Body weights ranged from 16.9 to 22.5 g with an average body weight across all groups 19.54 g (SD=1.04; CV=5.3%). Each mouse was treated with a single dose via IP route of administration with cisplatin at the dose of 11 mg/kg on the day 0 of the study. The mice in Group 2 and 4 were repeatedly treated with Compound 22 at the dose of 50 mg/kg with an interval of 24 h for seven consecutive days starting from Day 2 or Day 0 of the study, respectively. The mice in Groups 3 and 5 were repeatedly treated with compound 22 at the dose of 50 mg/kg twice a day (daily 9 AM and 6 PM injections) for seven consecutive days starting from the Day 2 or Day 0 of the study, respectively. The mice in Group 1 remained untreated after the cisplatin injection until the terminal sacrifice.

To induce acute kidney injury, cisplatin was administered without dilution as a factory-made 1 mg/ml solution for infusion at the injection volume of 11 ml/kg for the dose of 11 mg/kg. The formulation vehicle for compound 22 was Captisol—physiological saline—water for injections (20%:40%:40%, w/v/v). Only freshly prepared formulation was used for each dosing; each working formulation batch was prepared immediately prior to the administration. The working formulations were sterile filtered using 0.2 μm cellulose acetate syringe filters before injections. The dosing volume for the test compound was 5 ml/kg of body weight. The working formulations were administered as transparent clear solutions. Intraperitoneal (IP) route of administration was used in the study. Urea (BUN) was determined in the serum using a commercial kit according to the manufacturer's instructions. The principle of the method is the ability of urease to catalyze the transfer of H+ between urea and $H_2O$. The product of this reaction is $NH_4^+$ and $CO_3^{2-}$. The rate of absorbance change at λ=340 nm is proportional to the urea concentration. Reproducibility: CV=5.75%.

The significant gradual decrease of mean body weight was observed in all groups of mice within 1-4 days after cisplatin administration. The gradual recovery of mean body weight was observed in compound 22-treated mice in G2-G3 beginning from the fifth day of the study, and in G4-G5 beginning from the seventh day of the study. Mice in G1 had significantly weaker weight recovery overall. The mean level of urea was significantly less in compound 22 treated groups (G2-G5) compared to G1 on the 5th day after the cisplatin injection.

Figure 8:
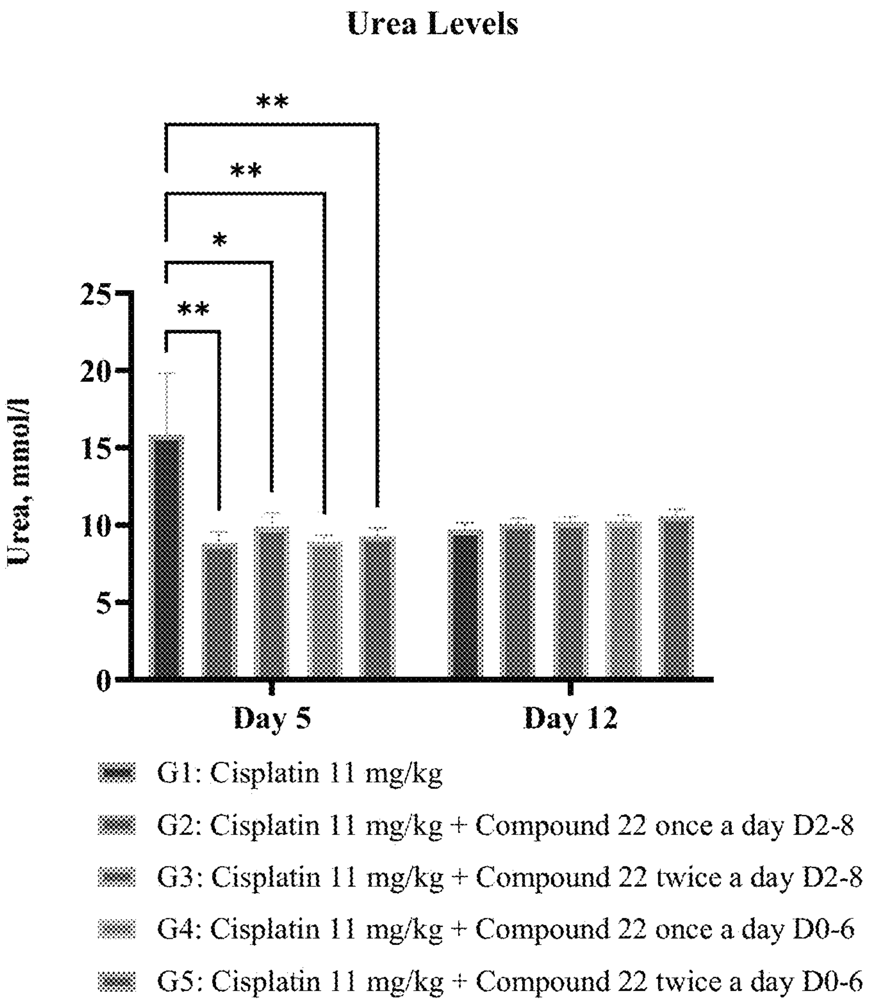
FIG. 8 illustrates urea levels in in cisplatin-induced AKI mice treated with illustrative Compound 22.

FIG. 8. Urea level (mean per group ±SE, %) in serum of C57Bl/6J female mice on the 5th and 12th day of the study. Cisplatin at a dose of 11 mg/kg was IP administered at Day 0 to all mice. The mice in G2, G3, G4 and G5 groups were repeatedly treated with Compound 22 once or twice a day on days 2-8 (D2-8) or days 0-6 (DO-6) of the study. Difference significance level compared to G1 (ANOVA): * p<0.05, ** p<0.01.

Figure 9A:
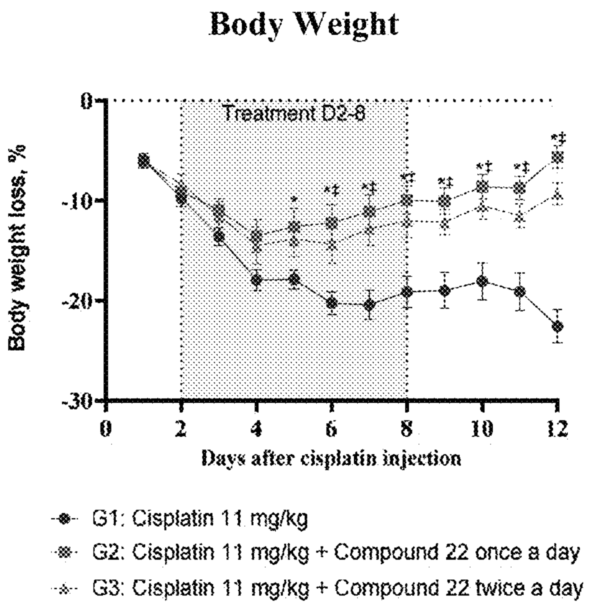
FIGS. 9A and 9B illustrate body weight in cisplatin-induced AKI mice treated with illustrative Compound 22 once or twice a day on days 2-8.
Figure 9B:
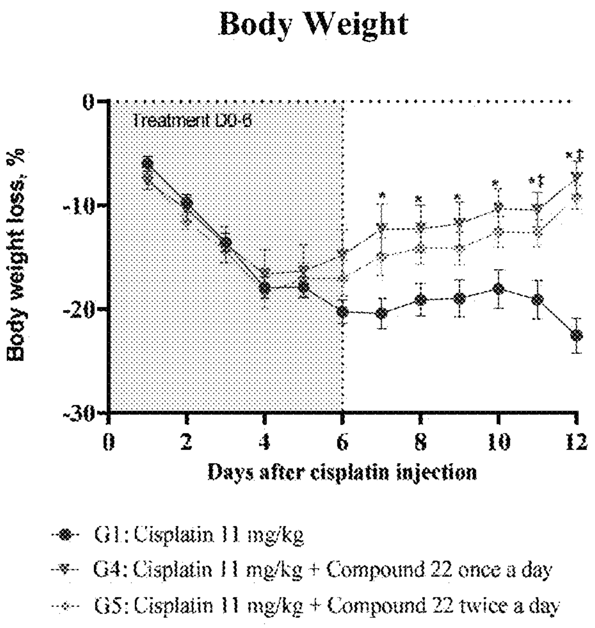

FIGS. 9A-9B. Body weight loss (mean per group±SE, %) of the mice survived during the study. Body weight loss was measured on different days compared to the initial weight on Day 0. Cisplatin at dose of 11 mg/kg was IP administered at Day 0 to all mice. The mice in G2, G3, G4 and G5 groups were repeatedly treated with Compound 22 once or twice a day on (FIG. 9A) days 2-8 (D2-8) of the study or (FIG. 9B) days 0-6 (DO-6) of the study. Statistically significant differences were determined by two-way ANOVA and Tukey post-hok analysis, denoted by * for G2 or G4, or t for G3 or G5 respectively, compared to G1.

Figure 10:
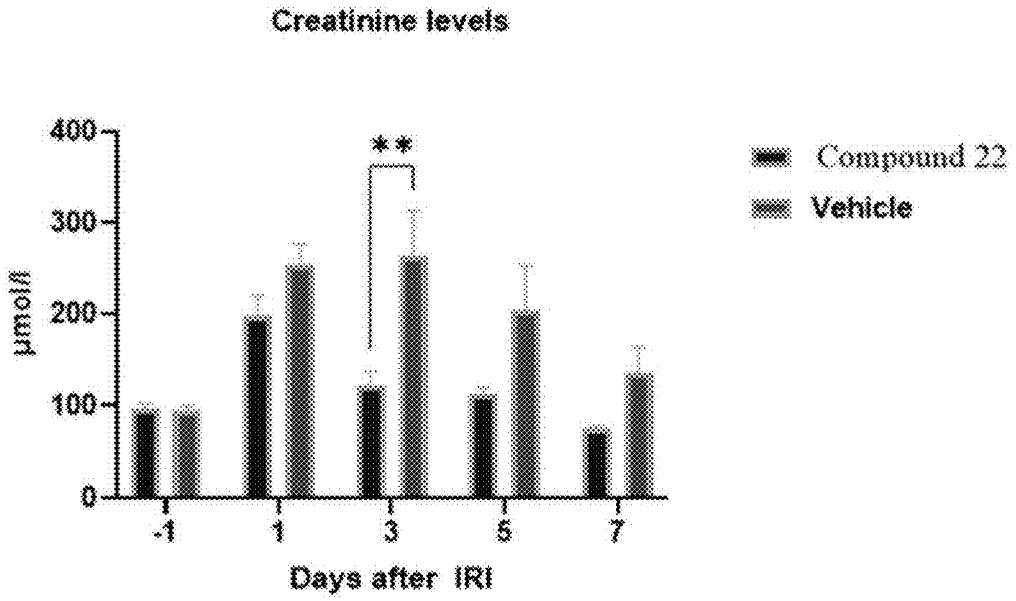
FIG. 10 illustrates creatinine levels in the serum of rats treated with illustrative compound 22.

FIG. 10 illustrates creatinine values in the serum of Sprague Dawley male rats following renal ischemia and repeated 7 days IV dosing with compound 22. Values are expressed as means±SEM of 8-14 rats per group. Significant differences were determined by two-way ANOVA, individual comparison was performed by Bonferroni's analysis, denoted by **.

Example 11: In Vivo Efficacy in a Murine AKI Model

The aim of the study was to investigate the efficacy of test compounds in the model of cisplatin induced acute kidney injury (CI-AKI) in mice. For example, the effect of daily repeated intraperitoneal (IP) administration of Compound 3 at doses of 50 mg/kg for 7 consecutive days on development of pathology in mice in CI-AKI model was evaluated. Serum analysis for urea (BUN) was performed on the 5th day and 9th days after cisplatin administration. The mean body weight loss per group was calculated every day of the study as percentage loss of initial (day 0) weight for each individual animal.

Study design, animal selection, handling and treatment were all in accordance with the CRO's study protocols and Institutional Animal Care and Use Guidelines. Animal treatment and serum samples preparation were conducted by the Animal Laboratory personnel at the CRO. 60 female C57BL/6J mice 9-12 weeks old were randomized by body weight and divided into 2 groups, 30 animals each. Body weights ranged from 13.9 to 22.0 g with an average body weight across all groups 17.75 g (SD=1.30; CV=7.3%). Each mouse was treated with a single dose via IP route of administration with cisplatin at the dose of 11 mg/kg on the day 0 of the study. The mice in Group 2 were repeatedly treated with Compound 3 at the dose of 50 mg/kg with an interval of 24 h for seven consecutive days starting from Day 2 of the study. The mice in Group 1 remained untreated after the cisplatin injection until the terminal sacrifice.

Cisplatin was administered without dilution as a factory-made 1 mg/ml solution for infusion at the injection volume of 11 ml/kg for the dose of 11 mg/kg. The formulation vehicle for compound 3 was Captisol—physiological saline—water for injections (20%:40%:40%, w/v/v). Only freshly prepared formulation was used for each dosing; each working formulation batch was prepared immediately prior to the administration. The working formulations were sterile filtered using 0.2 μm cellulose acetate syringe filters before injections. The dosing volume for the test compound was 5 ml/kg of body weight. The working formulations were administered as transparent clear solutions. Intraperitoneal (IP) route of administration was used in the study. Urea (BUN) was determined in the serum using a commercial kit according to the manufacturer's instructions. The principle of the method is the ability of urease to catalyze the transfer of $H^+$ between urea and $H_2O$. The product of this reaction is $NH_4^+$ and $CO_3^{2-}$. The rate of absorbance change at λ=340 nm is proportional to the urea concentration. Reproducibility: CV=5.75%. Creatinine was measured using Modified Jaffe's method, without deproteinization. In alkaline solution picrate reacts with creatinine to form a yellow-red 2,4,6-trinitrocyclohexadienate. The color intensity is proportional to the creatinine concentration. Reproducibility: CV=6.1%.

The significant gradual decrease of mean body weight was observed in all groups of mice within 1-5 days after cisplatin administration. The gradual recovery of mean body weight was observed in compound 3-treated mice in G2 beginning from the sixth day of the study. Mice in G1 had significantly weaker weight recovery overall. The mean level of urea and creatinine was significantly less in compound 3 treated group compared to G1 on the 5th day after the cisplatin injection.

Figure 11:
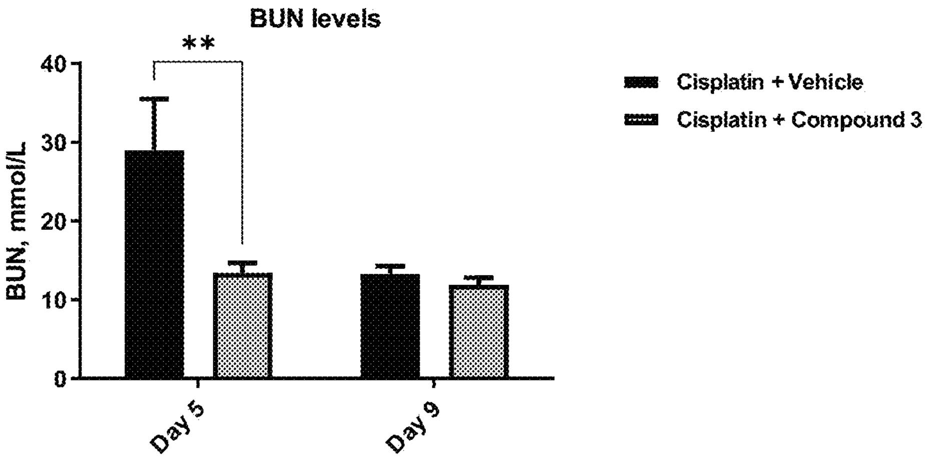
FIG. 11 illustrates urea levels in in cisplatin-induced AKI mice treated with illustrative Compound 3.

FIG. 11. Urea level (mean per group ±SE, %) in serum of C57Bl/6J female mice during the study. Cisplatin at a dose of 11 mg/kg was IP administered at Day 0 to all mice. The mice in G1 or G2 were repeatedly treated with Vehicle or Compound 3, respectively, with an interval of 24 h on days 2-9. Statistical significance was determined by ANOVA ($p<0.05$) followed by Bonferroni's multiple comparisons test. ** $p<0.01$.

Figure 12:
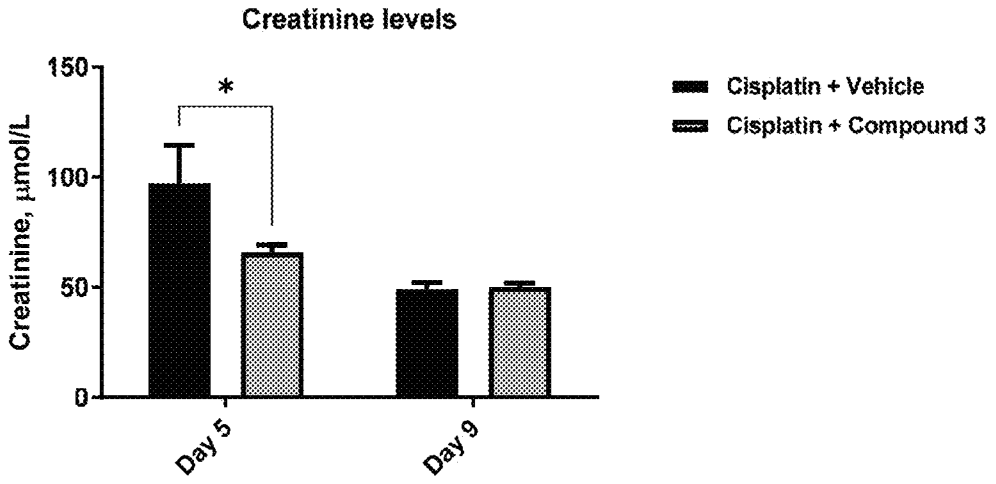
FIG. 12 illustrates creatinine levels in the serum of rats treated with illustrative compound 3.

FIG. 12. Creatinine level (mean per group ±SE, %) in serum of C57Bl/6J female mice during the study. Cisplatin at a dose of 11 mg/kg was IP administered at Day 0 to all mice. The mice in G1 or G2 were repeatedly treated with Vehicle or Compound 3, respectively, with an interval of 24 h on days 2-9. Statistical significance was determined by ANOVA ($p<0.05$) followed by Bonferroni's multiple comparisons test. * $p<0.05$.

Figure 13:
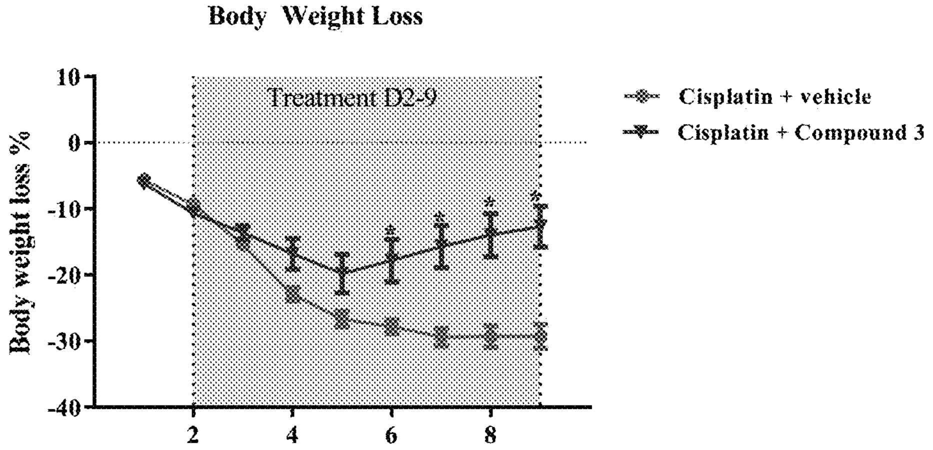
FIG. 13 illustrates body weight in cisplatin-induced AKI mice treated with illustrative Compound 3.

FIG. 13. Body weight loss (mean per group t SE, %) of mice in study. Body weight loss was measured on different days compared to the initial weight on Day 0. Cisplatin at a dose of 11 mg/kg was IP administered at Day 0 to all mice. The mice in G1 or G2 were repeatedly treated with Vehicle or Compound 3, respectively, with an interval of 24 h on days 2-9. Statistical significance was determined by ANOVA ($p<0.05$) followed by Bonferroni's multiple comparisons test. * $p<0.05$.

Example 12. Treatment of Cisplatin-Induced Acute Kidney Injury (AKI)

The goal of this study was to assess the effect of compound 22 at the doses of 50 mg/kg and 25 mg/kg on the development of cisplatin-induced acute kidney injury (AKI) in male Sprague Dawley rats. Compound 22 was administrated repeatedly seven consecutive days by 90 minutes infusion into a jugular vein using automatic pumps. Treatment was initiated simultaneously with the single intraperitoneal (IP) administration of cisplatin at the dose of 5 mg/kg. The experimental animal's mortality was recorded daily. Animals were observed for clinical signs daily during seven days dosing period and six days post-dosing period. Serum analysis for Creatinine and Urea were performed on day −4th (blank), 1st, 3rd, 6th, 9th, and 12th (terminal) day of the study.

Rat's jugular vein catheterization. Rat's jugular vein catheterization procedure was performed on −3rd day of the study. All experimental animals were anesthetized prior to surgical intervention by Telazol at the dose of 40 mg/kg body weight and Xylazine at the dose of 8 mg/kg body weight. The anesthetized rat was placed onto a heated surgical platform. The surgical area was shaved and gently scrubbed with a drop of iodine in 96% ethanol solution. The skin incision (2 cm) was made on the right of the midline of the neck at the level of the clavicle using a scalpel. Dissected jugular vein, separated from the salivary and lymphatic tissues, was visualized and isolated approximately 5 mm section of the vessel. The cranial end of the vessel was tied using 4-0 silk ligatures. By micro surgical scissors an incision was made to pass the catheter into the vein approximately 20 mm towards the heart. The caudal end of the jugular vein was tied to catheter's collar with silk ligatures aimed to secure the place of catheter. The free end of catheter was tunneled subcutaneously and connected to a transcutaneous button that features an external port with a cap at the nape of the animal's neck. During all the time of the surgery animals were observed for breathing patterns. To prevent dehydration after the surgery animals were injected with 2 ml physiological saline intraperitoneal. To prevent catheter occlusion and ensure its functioning flushing 0.10-0.20 ml amount of physiological saline with anticoagulant (Heparin, 500 IU/ml) was applied. First time catheter flushing was performed immediately after catheter was properly positioned in the jugular vein and fixed there. The procedure was repeated prior to infusion start. When a catheter was not in use, it was locked. The infusion was started three days after the catheter placement.

Fluid infusion. Programmable automatic syringe pumps system allowed for a fluid infusion of delivering determined volume at the selected infusion time. After the catheter flushing animals were connected to the tether and the swivel setup permitted free movement of the animal during the infusion. The duration of infusion was 90 minutes. The volume of infusion was 10 ml/kg; infusion rate was determined automatically according to time of infusion and volume of the administrated formulation. The infusions were performed from 10 am to 1 μm in a random order.

Drug formulation. Route and volume of administration. Cisplatin was administered without dilution as a factory-made 1 mg/ml solution for infusion at the injection volumes of 5 ml/kg which corresponded to the doses of 5 mg/kg. IP route was used for cisplatin administration in the study. Compound 22 was formulated in sterile conditions in physiological saline at the concentrations 5 mg/ml for the dose level 50 mg/kg and 2.5 mg/ml for the dose level 25 mg/kg and was administrated as true solution. All formulations were sterilized by filtration via Minisart RC 0.2 μm sterile syringe filter. Compound 22 infusion duration was 90 minutes. The administrated volume for all group was 10 ml/kg of the body weight.

Frequency and duration of the application. cisplatin was administered once on day 0 of the study, 30 min before first infusion. Compound 22 as well as vehicle was administrated 7 consecutive days (day 0-day 6) once per day.

Duration of the experimental period. Seven days of acclimatization, one day of catheterization procedure, three days recovery after the surgical intervention, one day of the cisplatin treatment, seven days of infusion treatment, six posttreatment days observation.

Clinical chemistry. Creatinine and Urea were determined in the serum using commercial kits according to the manufacturer's instructions. Creatinine. Modified Jaffe's method, without deproteinization. In alkaline solution picrate reacts with creatinine to form a yellow-red 2,4,6-trinitrocyclohexadienate. The color intensity is proportional to the creatinine concentration. Reproducibility: CV=4.7%. Urea (BUN). The principle of the method is the ability of urease to catalyze the transfer of H+ between urea and $H_2O$. The product of this reaction is $NH_4$ and $CO_3^{2-}$. The rate of absorbance change at $\lambda=340$ nm is proportional to the urea concentration. Reproducibility: CV=5.9%.

Samples collection and preparation. Samples for H&E staining were prepared as follows: one kidney (right) was placed immediately after euthanasia into 10% neutral buffered formalin at room temperature, with occasional stirring (2-3 times). After 3 days of formalin fixation, the samples were dehydrated using STP 120 Spin Tissue Processor and embedded in type 6 paraffin using Modular tissue embedding center EC 350.

Histopathology. Sample preparation. Paraffin-embedded blocks were cut using rotary microtome to obtain the slides of 4 μm thickness, which were deparaffinated for further hematoxylin and eosin (H&E) staining. The cuts were performed on three different deepness of kidney and heart, and three slides were taken from each location. The slides were exposed to hematoxylin solution for 1-2 minutes, differentiated in running tap water until the excess of the dye was removed and the nuclei became stained, then exposed to eosin solution, rinsed in distilled water, rapidly dehydrated and enclosed under a cover slip in Canadian balm. Hematoxylin stained cell nuclei, and eosin stained cell cytoplasm and the extracellular matrix. Other cells structures had different hues and combinations of colors.

Histopathological examination. H&E staining gave observation of the general layout and distribution of cells and provided the general overview of the tissues' structure. Three sections from different depths were analyzed for each animal.

Statistical Analysis. Student's t-test for independent samples, one-way ANOVA, or two-way ANOVA were performed for statistical comparisons according to Standard Operating Procedures and were applied to calculate the significance of differences. The differences were considered significant if $p<0.05$.

Figure 14:
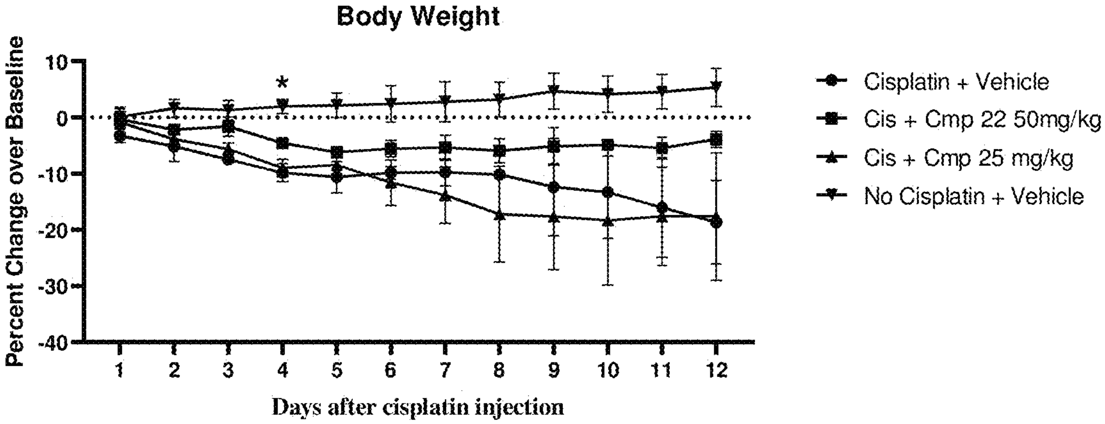
FIG. 14 illustrates body weight change over baseline in SD male rats with cisplatin-induced AKI.

Results:

Body Weight. Rats from the cisplatin, vehicle group exhibited significant decreasing of their body weight up to 18.6% on day 12 of the study compared with No Cisplatin, vehicle group (FIG. 14). Experimental animals, treated with compound 22 at the doses of 50 mg/kg demonstrated gradual body weight losses beginning from day 1, and survived animals from the group demonstrated gradual body weight gain in post-treatment period, resulting to −3.9% BWC. No statistical significance was revealed in comparison with the cisplatin, vehicle group. Experimental animals, treated with compound 22 at the doses of 25 mg/kg demonstrated gradual body weight losses beginning from day 2 during treatment and post-treatment period, resulting to −17.6% BWC. No statistical significance was revealed in comparison with the cisplatin, vehicle group. FIG. 14 illustrates body weight dynamics in SD male rats with cisplatin-induced AKI following seven repeated infusions with compound 22 at the doses of 50 mg/kg and 25 mg/kg. Values are expressed as means SEM of 2-6 rats per group. Statistical differences were calculated using two-way ANOVA. * —$p<0.05$ comparison with all other groups.

Figure 15:
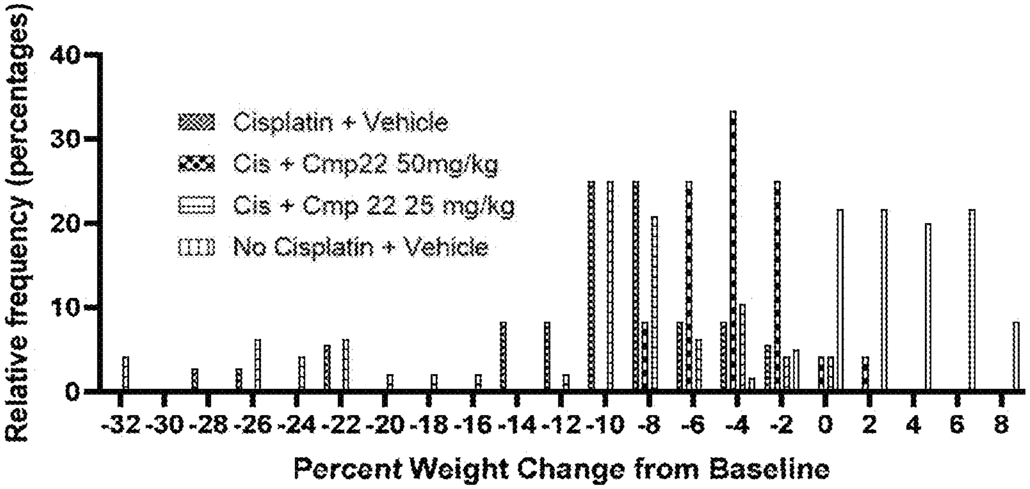
FIG. 15 illustrates a histogram of weight loss percentages from baseline in SD male rats with cisplatin-induced AKI.

Frequency distribution analysis was used to identify the severity of weight loss for individual animals at the end of the study period (FIG. 15). A greater number of cisplatin treated animals had significantly greater body weight loss compared to compound 22 treated animals. These data suggest treatment with compound 22 decreases the severity of weight loss in individual animals compared to cisplatin treatment. FIG. 15 illustrates a histogram of weight loss percentages from baseline in SD male rats with cisplatin-induced AKI following seven repeated infusions with compound 22 at the doses of 50 mg/kg and 25 mg/kg. Histogram was calculated for individual values for each group.

Figure 16:
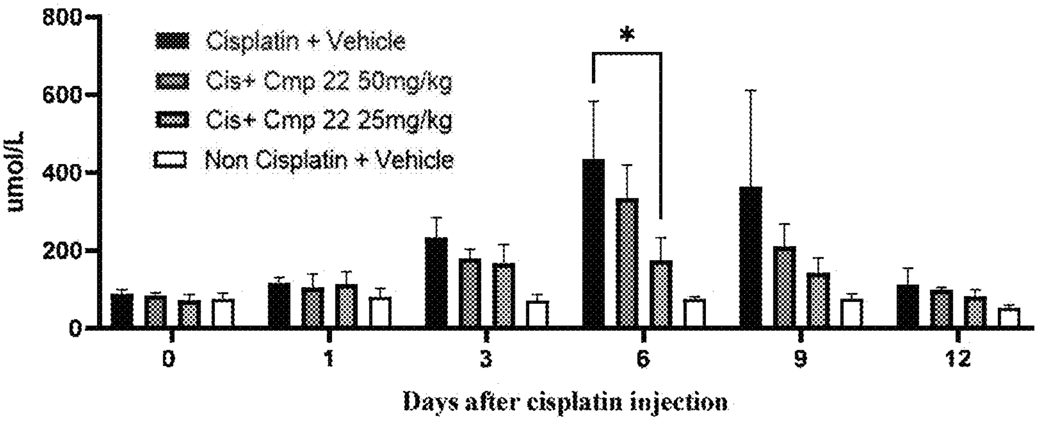
FIG. 16 illustrates creatinine values in the serum of in SD male rats with cisplatin-induced AKI.
Figure 17:
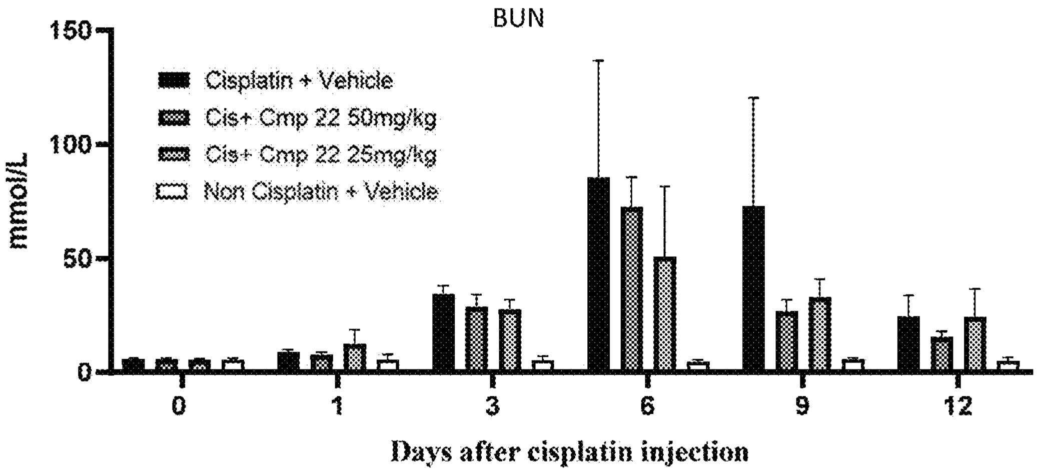
FIG. 17 illustrates urea values in the serum of in SD male rats with cisplatin-induced AKI.

Clinical Chemistry. Single cisplatin treatment with followed vehicle infusion lead to significant Creatinine (FIG. 16) and Urea (FIG. 17) level increasing in rats of cisplatin, vehicle group compared with No cisplatin, vehicle group. Both tested doses of compound 22 prevented cisplatin-induced AKI development by decreasing serum Creatinine and Urea levels during infusions and post-infusion period. The significant decrease of Creatinine values occurred on day 6 in group of rats treated with compound 22 at both test doses and on day 9 in rats treated with compound 22 at the doses of 50 mg/kg—all compared to value of the cisplatin, vehicle-treated group. The significant decrease of Urea values occurred on day 6 in rats treated with compound 22 at the dose of 25 mg/kg and on day 9 in animals treated with compound 22 at the dose of 50 mg/kg—all compared to value of the cisplatin, vehicle group. FIG. 16 illustrates creatinine values in the serum of in SD male rats with cisplatin-induced AKI following seven repeated infusions with compound 22 at the doses of 50 mg/kg and 25 mg/kg (2-6 rats per group) on −4th day, 1st day, 3rd day, 6th day, 9th, and 12th day of the study. Values are expressed as means±SEM of 2-6 rats per group. Statistical differences were calculated using a two-way ANOVA test at the level of $p<0.05$ (*) was indicated to groups treated with compound 22 compared to the cisplatin, Vehicle group. FIG. 17 illustrates urea values in the serum of in SD male rats with cisplatin-induced AKI following seven repeated infusions with compound 22 at the doses of 50 mg/kg and 25 mg/kg (2-6 rats per group) on −4th day, 1st day, 3rd day, 6th day, 9th, and 12th day of the study. Values are expressed as means±SEM of 2-6 rats per group. Statistical differences were calculated using a two-way ANOVA test at the level of $p<0.05$ (*) was indicated to groups treated with compound 22 compared to the cisplatin, Vehicle group.

Figure 18:
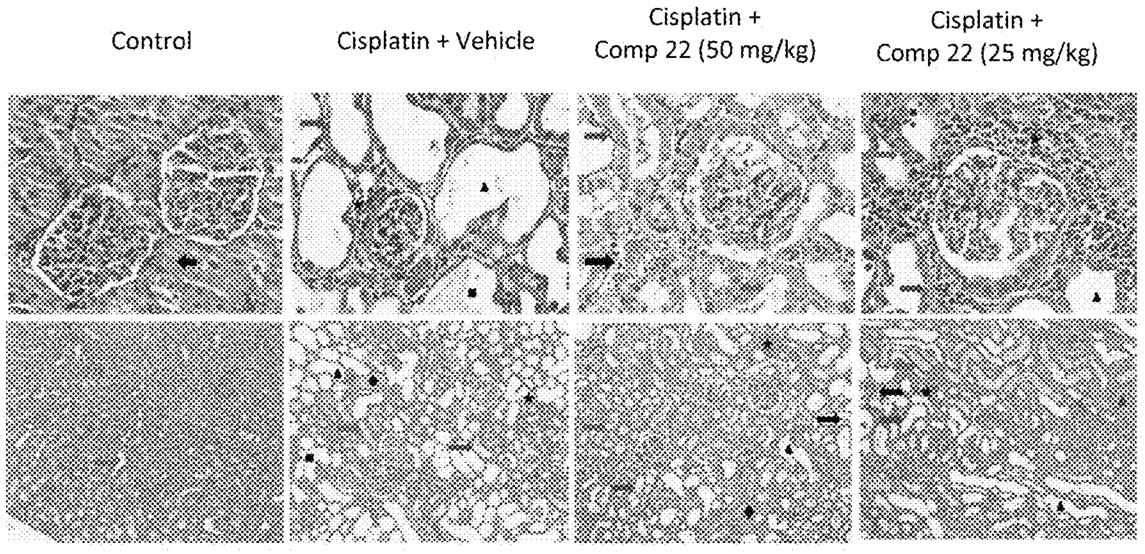
FIG. 18 illustrates microphotographs of kidneys of SD male rats with cisplatin-induced AKI.

Histopathology. Vehicle-treated animals with cisplatin injection had severe tubular epithelium flattening, severe loss of brush border, medium tubular epithelium loss, medium tubular atrophy, medium tubular dilation, mild loss of tubules, medium interstitial nephritis, mild glomerulonephritis, mild cast deposition, mild frequency of necrotic loci, mild connective tissue accumulation, mild tubular hyperplasia. FIG. 18 illustrates microphotographs of kidneys of SD male rats with cisplatin-induced AKI following seven repeated infusions with compound 22 at the doses of 50 mg/kg and 25 mg/kg at the terminal day of the study. Magnification ×400 (top) and 100× (bottom). Arrows indicate tubular epithelium flattening, arrows—loss of brush border, triangles—tubular dilation, triangle—tubular basophilia, asterisk—inflammatory infiltrate, diamond—connective tissue accumulation, arrows—blood vessel dilation, arrows—eosinophilic cast deposits, arrows—tubular hyperplasia, square—loss of tubules, circle—necrotic loci. Occurrences of tubular epithelium flattening, loss of brush border, tubular epithelium loss, tubular atrophy, tubular dilation, interstitial nephritis, glomerulonephritis, cast deposition, connective tissue accumulation, tubular hyperplasia, and total injury scores with and without tubular basophilia and hyperplasia were significantly higher compared to Vehicle-treated animals without cisplatin injection (FIG. 18), which could be evidence the kidney injury development. Compound 22-treated (50 mg/kg) animals with cisplatin injection demonstrated medium tubular epithelium flattening, severe loss of brush border, medium tubular epithelium loss, occasional tubular epithelium vacuolation, medium/mild tubular atrophy, medium tubular dilation, occasional loss of tubules, mild/medium interstitial nephritis, mild cast deposition, occasional necrotic loci, mild connective tissue accumulation, occasional tubular basophilia, occasional tubular hyperplasia. There was no significant difference in scores compared to Vehicle-treated animals with cisplatin injection, however, only occurrences of tubular epithelium flattening, loss of brush border, tubular epithelium loss, tubular dilation, and connective tissue accumulation were significantly higher compared to vehicle-treated animals without cisplatin injection (FIG. 18), which suggests evidence of less severe kidney injury development compared to that in Vehicle-treated animals with cisplatin injection.

Compound 22-treated (25 mg/kg) animals with cisplatin injection demonstrated medium/severe tubular epithelium flattening, severe loss of brush border, medium tubular epithelium loss, mild tubular atrophy, medium tubular dilation, mild loss of tubules, medium/severe interstitial nephritis, mild glomerulonephritis, medium cast deposition, medium-frequent necrotic loci, occasional hemorrhages, mild connective tissue accumulation, occasional tubular hyperplasia. There was no significant difference in scores compared to Vehicle-treated animals with cisplatin injection. If compared to Vehicle-treated animals without cisplatin injection, the same indices were significantly higher except tubular atrophy and tubular hyperplasia ones. However, it should be noted, that interstitial nephritis and cast deposition scores did not differ from vehicle-treated animals without cisplatin injection because of higher score variability across the group (FIG. 18). These data suggest less kidney injury detected with compound 22 treatment compared to cisplatin- and Vehicle-treated animals' tissues, but more pronounced one compared to tissue in compound 22-treated (50 mg/kg) animals.

Example 13. Cancer Treatment

Figure 19:
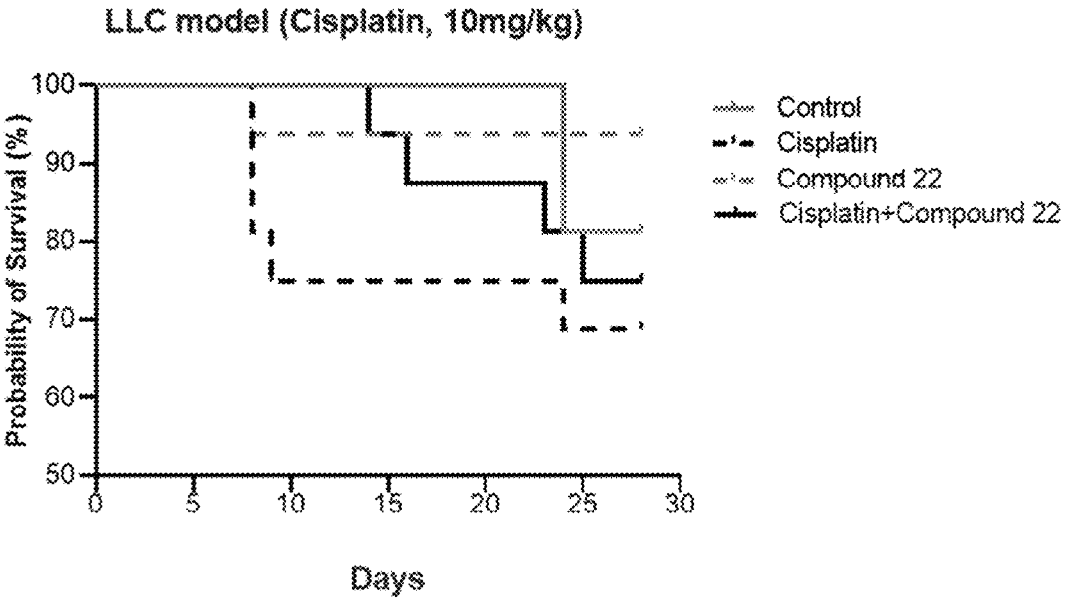
FIG. 19 illustrates the survival efficacy of Compound 22, cisplatin, and the combination of Compound 22+cisplatin in LLC animals.
Figure 20:
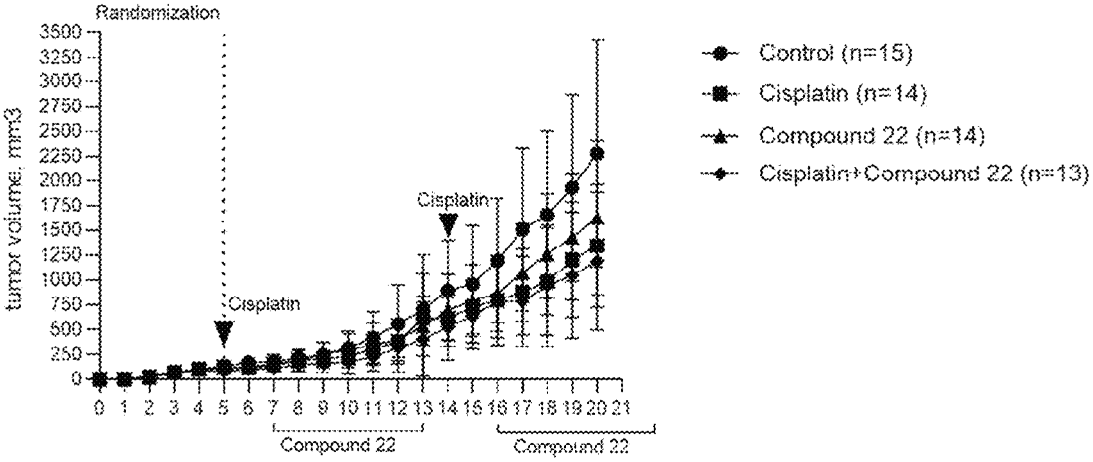
FIG. 20 illustrates the anti-tumor efficacy of Compound 22, cisplatin, and the combination of Compound 22+cisplatin in LLC animals.

Compositions, system, and/or kits of the present disclosure can be effective at treating cancer and/or tumors. See FIG. 19 and FIG. 20. For example, a treatment protocol comprising illustrative compound 22 and cisplatin, co-administered is effective as an anti-tumor treatment, in addition to compound 22 preventing/attenuating kidney damage (caused by the chemotherapeutic nephrotoxin), restoring kidney function, and/or increasing patient survival during chemotherapy. FIG. 19 illustrates the survival efficacy of Compound 22 (50 mg/kg), cisplatin (10 mg/kg), and the combination of Compound 22+cisplatin in LLC animals. The co-administration of compound 22 (an illustrative PTBA prodrug) increased the probability of survival in LLC animals at day 15 from ~75% (cisplatin alone) to ~95% (Compound 22+cisplatin co-administration). FIG. 20 illustrates the anti-tumor efficacy of Compound 22, cisplatin, and the combination of Compound 22+cisplatin in LLC animals. cisplatin was administered to LLC animals at day 5 and day 14 of a 21 day study. Compound 22 was co-administered (once daily) 48 hours after each dose of cisplatin, and for 6 additional, consecutive days thereafter. Co-administration of Compound 22 with cisplatin retained the antitumor efficacy observed in cisplatin-treated animals, demonstrating the suitability of co-administration.

Accordingly, novel PTBA prodrugs according to the present disclosure are effective anti-AKI agents suitable for co-administration with platinum-based chemotherapeutic nephrotoxins, in established cancer treatment protocols.

Conclusion

While the foregoing detailed description makes reference to specific exemplary embodiments, the present disclosure may be embodied in other specific forms without departing from its spirit or essential characteristics. Accordingly, the described embodiments are to be considered in all respects only as illustrative and not restrictive. For instance, various substitutions, alterations, and/or modifications of the inventive features described and/or illustrated herein, and additional applications of the principles described and/or illustrated herein, which would occur to one skilled in the relevant art and having possession of this disclosure, can be made to the described and/or illustrated embodiments without departing from the spirit and scope of the disclosure as defined by the appended claims. Such substitutions, alterations, and/or modifications are to be considered within the scope of this disclosure.

The scope of the invention is, therefore, indicated by the appended claims rather than by the foregoing description. The limitations recited in the claims are to be interpreted broadly based on the language employed in the claims and not limited to specific examples described in the foregoing detailed description, which examples are to be construed as non-exclusive and non-exhaustive. All changes which come within the meaning and range of equivalency of the claims are to be embraced within their scope.

It will also be appreciated that various features of certain embodiments can be compatible with, combined with, included in, and/or incorporated into other embodiments of the present disclosure. For instance, systems, methods, and/or products according to certain embodiments of the present disclosure may include, incorporate, or otherwise comprise features described in other embodiments disclosed and/or described herein. Thus, disclosure of certain features relative to a specific embodiment of the present disclosure should not be construed as limiting application or inclusion of said features to the specific embodiment.

In addition, unless a feature is described as being requiring in a particular embodiment, features described in the various embodiments can be optional and may not be included in other embodiments of the present disclosure. Moreover, unless a feature is described as requiring another feature in combination therewith, any feature herein may be combined with any other feature of a same or different embodiment disclosed herein. It will be appreciated that while features may be optional in certain embodiments, when features are included in such embodiments, they can be required to have a specific configuration as described in the present disclosure.

Likewise, any steps recited in any method or process described herein and/or recited in the claims can be executed in any suitable order and are not necessarily limited to the order described and/or recited, unless otherwise stated (explicitly or implicitly). Such steps can, however, also be required to be performed in a specific order or any suitable order in certain embodiments of the present disclosure.

Furthermore, various well-known aspects of illustrative systems, methods, products, and the like are not described herein in particular detail in order to avoid obscuring aspects of the example embodiments. Such aspects are, however, also contemplated herein.

We claim:

1. A pharmaceutical treatment system for administration to a cancer patient, the treatment system comprising:

a platinum-based chemotherapeutic drug in an amount sufficient to reduce the number of cancer cells in the patient; and a prodrug of 4-(phenylthio)butanoic acid (PTBA), according to Formula I:

Formula I

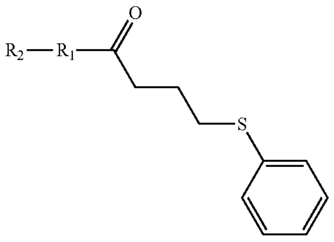

or a stereoisomer, tautomer or pharmaceutically acceptable salt thereof, in an amount sufficient to attenuate kidney injury induced by the platinum-based chemotherapeutic drug in the patient and/or improve kidney function in the patient, wherein:

$R_1$ is O; and $R_2$ is selected from the group consisting of 1-(N,N,N-trimethyl)ethanamine, 1-(N,N-dimethyl)ethanamine, and 1-(1-methyl-N,N-dimethyl)ethanamine.

2. The system of claim 1, wherein the platinum-based chemotherapeutic drug is selected from the group consisting of cisplatin, oxaliplatin, carboplatin, nedaplatin, phenanthriplatin, and picoplatin.

3. The system of claim 1, wherein $R_2$ is 1-(N,N,N-trimethyl)ethanamine.

4. The system of claim 1, wherein the platinum-based chemotherapeutic drug and the prodrug are each disposed in a pharmaceutically-acceptable carrier or excipient.

5. The system of claim 1, wherein the prodrug is administered in an amount sufficient to provide a dose of 1-100 mg/kg of subject body mass/weight.

6. A method, comprising administering the pharmaceutical treatment system of claim 1 to a cancer patient, wherein at least one dose of the prodrug is administered within 48 hours of administration of the platinum-based chemotherapeutic drug.

7. A method, comprising administering to a cancer patient:

a platinum-based chemotherapeutic drug in an amount sufficient to reduce the number of cancer cells in the patient; and a prodrug of 4-(phenylthio)butanoic acid (PTBA), according to Formula I:

Formula I

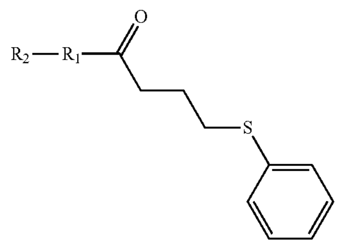

or a stereoisomer, tautomer or pharmaceutically acceptable salt thereof, in an amount sufficient to attenuate kidney injury induced by the platinum-based chemotherapeutic drug in the patient and/or improve kidney function in the patient, wherein:

$R_1$ is O; and $R_2$ is selected from the group consisting of 1-(N,N,N-trimethyl)ethanamine, 1-(N,N-dimethyl)ethanamine, and 1-(1-methyl-N,N-dimethyl)ethanamine.

8. The method of claim 7, wherein:

the platinum-based chemotherapeutic drug and the prodrug are each disposed in a pharmaceutically-acceptable carrier or excipient;

the prodrug is administered in an amount sufficient to provide a dose of 1-100 mg/kg of subject body mass/weight; and/or at least one dose of the prodrug is administered within 48 hours of administration of the platinum-based chemotherapeutic drug.

9. A pharmaceutical treatment system for administration to a cancer patient, the system comprising:

a platinum-based chemotherapeutic drug in an amount sufficient to reduce the number of cancer cells in the patient; and a prodrug of 4-(phenylthio)butanoic acid (PTBA), according to Formula I:

Formula I

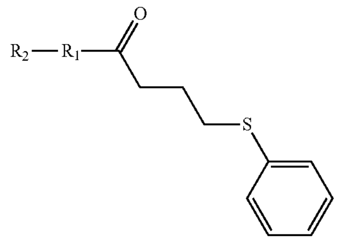

or a stereoisomer, tautomer or pharmaceutically acceptable salt thereof, in an amount sufficient to attenuate kidney injury induced by the platinum-based chemotherapeutic drug in the patient and/or improve kidney function in the patient, wherein:

$R_1$ is O or NH; and when $R_1$ is O, $R_2$ is selected from:

(a) 1-(N,N-dimethyl)ethanamine, 1-(1-methyl-N,N-dimethyl)ethanamine, or 1-(N,N,N-trimethyl)ethanamine, (b) 4-N-methylpiperidine, 4-N-ethylpiperidine, 4-(1,4-dimethyl)piperidine, 4-N-methyl-2-ethyl-1-N-piperazine, 3-pyrrolidine, or 2-methyl-2-azaspiro[3.3]heptane, (c) N-ethylethanolamine or 2-(ethylamino)ethanol, (d) 2-ethoxyethanol, 2,3-propanediol, (e) 2-butanedioic acid, (f) 2,6-diamino-N-ethyl-N-hexanamide, 2-amino-3-methyl-N-propyl-N-butanamide, or N-(1,3-dicarboxyl)-2-amino-propanamide, and when $R_1$ is NH, $R_2$ is selected from:

(a) 2-butanedioic acid, 2-pentanedioic acid, or 2-(5-amino)-pentanoic acid, and (b) 2-(3-aminopropane)-N-2-butanedioic-2-ethanamide, 2-(3-aminopropane)-N-2-butanedioic-2-ethanamide, 2-(3-aminopropane)-N-2-pentanedioic-2-ethanamide, 2-(3-aminopropane)-N-2-pentanedioic-2-ethanamide, 2-(2-carboxyethyl)-N-(2-(3-aminopropane)-carboxymethyl)-2-ethanamide, 2-carboxymethyl-N-(2-(3-aminopropane)-carboxymethyl)-2-ethanamide, or 2-(hydroxymethyl)-N-2-pentanedioic-2-ethanamide.

10. The compound, or prodrug, of claim 9, wherein $R_2$ is not H, alkyl, ethyl, propyl, isopropyl, or butyl, aryl, phenyl, benzyl, carboxyl (COOH), methanol, ethanol, propanol, or isopropanol.

11. The system of claim 9, wherein $R_1$ is O.

12. The system of claim 9, wherein $R_1$ is NH.

13. A method, comprising administering the pharmaceutical treatment system of claim 9 to a cancer patient.

* * * * *